(12) United States Patent
Yoshioka et al.

(10) Patent No.: US 8,163,939 B2
(45) Date of Patent: Apr. 24, 2012

(54) ASCORBIC ACID DERIVATIVE OR SALT THEREOF, PRODUCTION METHOD THEREOF, AND COSMETIC

(75) Inventors: Masato Yoshioka, Higashiosaka (JP); Norihisa Taira, Higashiosaka (JP); Akane Kamiyama, Higashiosaka (JP); Keiichi Uehara, Higashiosaka (JP); Naoya Hashimoto, Higashiosaka (JP)

(73) Assignee: Seikwa Kasei Company, Limited, Osaka (JP)

( * ) Notice: Subject to any disclaimer, the term of this patent is extended or adjusted under 35 U.S.C. 154(b) by 180 days.

(21) Appl. No.: 12/673,952

(22) PCT Filed: Aug. 21, 2008

(86) PCT No.: PCT/JP2008/064934
§ 371 (c)(1),
(2), (4) Date: Feb. 17, 2010

(87) PCT Pub. No.: WO2009/025328
PCT Pub. Date: Feb. 26, 2009

(65) Prior Publication Data
US 2011/0059034 A1   Mar. 10, 2011

(30) Foreign Application Priority Data

Aug. 22, 2007 (JP) ................................. 2007-216446
Aug. 22, 2007 (JP) ................................. 2007-216448

(51) Int. Cl.
*C07D 307/62* (2006.01)
*A61K 8/00* (2006.01)
(52) U.S. Cl. ........................................ 549/315; 424/62

(58) Field of Classification Search .................. 549/315; 424/62
See application file for complete search history.

(56) References Cited

FOREIGN PATENT DOCUMENTS

| JP | 4-149117 A | 5/1992 |
|---|---|---|
| JP | 2002-265459 A | 9/2002 |
| JP | 2003-119120 A | 4/2003 |
| JP | 2005-239645 A | 9/2005 |
| JP | 2006-1866 A | 1/2006 |
| JP | 2006-131567 A | 5/2006 |

OTHER PUBLICATIONS

Morisaki et al. STN Accession No. 1996:596965, Document No. 125:329207, Abstract of Morisaki et al. Chemical & Pharmaceutical Bulletin (1996), 44(9),1647-1655.*
Morisaki et al., "Design of Novel Hybrid Vitamin C Derivatives: Thermal Stability and Biological Activity", Chem. Pharm. Bull. 44(9), 1996, pp. 1647-1655.

* cited by examiner

*Primary Examiner* — Nizal Chandrakumar
(74) *Attorney, Agent, or Firm* — Birch, Stewart, Kolasch & Birch, LLP

(57) ABSTRACT

Disclosed is an ascorbic acid derivative or a salt thereof wherein at least one of hydrogen atoms in hydroxy groups at the 2-position and the 3-position of ascorbic acid is substituted by R—O—CH$_2$—CH(OH)—CH$_2$—, R—O—CH$_2$—CH(CH$_2$OH)—, R—CH(CH$_2$OH)—, R—CH(OH)—CH$_2$— (wherein R represents an alkyl group, an alkenyl group or a phenyl group), or a hydroxycyclohexyl group. Also disclosed is a method for producing an ascorbic acid derivative or a salt thereof, which is characterized by reacting ascorbic acid with an epoxy compound such as an alkyl glycidyl ether, an epoxy alkane or an alicyclic epoxy.

17 Claims, No Drawings

ASCORBIC ACID DERIVATIVE OR SALT THEREOF, PRODUCTION METHOD THEREOF, AND COSMETIC

TECHNICAL FIELD

The present invention relates to an ascorbic acid derivative or salt thereof used suitably as a raw material of a cosmetic, or the like. The present invention also relates to a method of producing the ascorbic acid derivative. Further, the present invention relates to a cosmetic obtained by compounding the ascorbic acid derivative or salt thereof.

BACKGROUND ART

Ascorbic acid is a safe and useful antioxidant, and is known as a compound having an excellent whitening effect. On the other hand, it is unstable against light, heat and oxidation, suitably utilization thereof in the cosmetic field is prevented. Then, various ascorbic acid derivatives or salts thereof are suggested as materials having improved stability over time in comparison with ascorbic acid, and it is suggested to compound them into a skin external agent for whitening (patent document 1, patent document 2) and to compound them into a cosmetic (patent document 3).

However, many of the above-described ascorbic acid derivatives and salts thereof have problems such as coloration and generation of odor over time and the like, and the stability over time thereof is still insufficient. Moreover, endurance of activity in a living body is short. Thus, there is a desire for improvement thereof.

As materials further improving stability over time, an ascorbic acid phosphate and ascorbic acid glucoside generating free ascorbic acid by the action of an enzyme and the like are suggested (patent document 4). However, the production of them is complicated and they are expensive. Then, an ascorbic acid derivative is desired which has excellent functions originally owned by ascorbic acid derivatives such as a whitening effect, collagen production promoting effect and the like, shows stability over time, and further, can be produced by an inexpensive and simple production method.

(Patent document 1) JP-A No. 62-221611
(Patent document 2) JP-A No. 2005-60239
(Patent document 3) JP-A No. 1-228978
(Patent document 4) Japanese Patent No. 2926412

SUMMARY OF THE INVENTION

Problem to be Solved by the Invention

An object of the present invention is to provide a novel ascorbic acid derivative or salt thereof having excellent functions originally owned by ascorbic acid such as a whitening effect, collagen production promoting effect and the like, and showing stability and little coloration, odor change, activity lowering and the like even in storage over a long period of time. Another object of the present invention is to provide a production method which is capable of producing this novel ascorbic acid derivative or salt thereof easily and cheaply. Further object of the present invention is to provide a cosmetic obtained by compounding this novel ascorbic acid derivative or salt thereof.

Means for Solving the Problem

The present inventors have intensively investigated in view of the above-described situations, and resultantly found that a novel ascorbic acid derivative or salt thereof of the following formula (I) has excellent functions such as a whitening effect, moisturizing effect, collagen production promoting effect and the like, as well as shows stability and little coloration, odor change, activity lowering and the like even in storage over a long period of time. The present inventors have further found that a novel ascorbic acid derivative of the following formula (I) can be easily produced by simply reacting ascorbic acid with a compound having an epoxide skeleton such as glycidol, alkyl glycidyl ether, epoxy alkane or the like. The present invention has been completed based on these findings.

The present invention provides an ascorbic acid derivative represented by the following general formula (I) or salt thereof (Claim 1).

(Chemical formula 1)

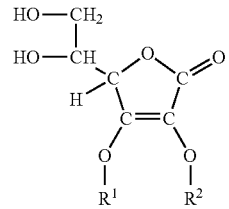

[wherein,
$R^1$ represents H, alkyl group having 1 to 22 carbon atoms, alkenyl group having 2 to 22 carbon atoms, benzyl group, $R^3$—O—$CH_2$—CH(OH)—$CH_2$—, $R^4$—O—$CH_2$—CH($CH_2$OH)—, $R^5$—CH($CH_2$OH)—, $R^6$—CH(OH)—$CH_2$— or hydroxycyclohexyl group,
$R^2$ represents H, alkyl group having 1 to 22 carbon atoms, alkenyl group having 2 to 22 carbon atoms, benzyl group, $R^7$—O—$CH_2$—CH(OH)—$CH_2$—, $R^8$—O—$CH_2$—CH($CH_2$OH)—, $R^9$—CH($CH_2$OH)—, $R^{10}$—CH(OH)—$CH_2$— or hydroxycyclohexyl group, here,
$R^3$ and $R^4$ represent H, alkyl group having 1 to 22 carbon atoms, alkenyl group having 2 to 22 carbon atoms or phenyl group,
$R^5$ and $R^6$ represent H, alkyl group having 1 to 20 carbon atoms, alkenyl group having 2 to 20 carbon atoms or phenyl group,
$R^7$ and $R^8$ represent H, alkyl group having 1 to 22 carbon atoms, alkenyl group having 2 to 22 carbon atoms or phenyl group,
$R^9$ and $R^{10}$ represent H, alkyl group having 1 to 20 carbon atoms, alkenyl group having 2 to 20 carbon atoms or phenyl group,
provided that when $R^1$ represents H, alkyl group having 1 to 22 carbon atoms, alkenyl group having 2 to 22 carbon atoms or benzyl group, $R^2$ does not represents any of H, alkyl group having 1 to 22 carbon atoms, alkenyl group having 2 to 22 carbon atoms and benzyl group.].

The present invention is an ascorbic acid derivative represented by the above-described formula (I). Further, when $R^1$ is H or $R^2$ is H in the above-described formula (I), ascorbic acid derivative salts obtained by substituting a hydrogen ion generated by dissociation of this H with a positive ion such as a metal ion, ammonium ion and the like are also included in the present invention.

As described later, an ascorbic acid derivative or salt thereof represented by the general formula (I) can be produced by a method having a process of reacting a compound having an epoxy ring (epoxy compound) selected from glycidol, specifically structured alkyl glycidyl ether, alkenyl glycidyl ether, phenyl glycidyl ether, ethylene oxide, epoxy alkane, epoxy alkene, styrene oxide and alicyclic epoxy to a hydroxyl group at 2-position and/or 3-position of ascorbic acid. In reacting ascorbic acid with glycidol, alkyl glycidyl ether, alkenyl glycidyl ether or phenyl glycidyl ether, a mixture of a compound in which $R^1$ is $R^3$—O—$CH_2$—CH(OH)—$CH_2$— and a compound in which $R^1$ is $R^4$—O—$CH_2$—CH($CH_2$OH)—, or a mixture of a compound in which $R^2$ is $R^7$—O—$CH_2$—CH(OH)—$CH_2$— and a compound in which $R^2$ is $R^8$—O—$CH_2$—CH($CH_2$OH)— are generated in some cases, and in reacting ascorbic acid with ethylene oxide, epoxy alkane, epoxy alkene or styrene oxide, a mixture of a compound in which $R^1$ is $R^5$—CH($CH_2$OH)— and a compound in which $R^1$ is $R^6$—CH(OH)—$CH_2$—, and a mixture of a compound in which $R^2$ is $R^9$—CH($CH_2$OH)— and a compound in which $R^2$ is $R^{10}$—CH(OH)—$CH_2$— are generated in some cases.

In the above-described reaction, an epoxy ring is ring-opened so as to generate a primary hydroxyl group or secondary hydroxyl group and a mixture of them is obtained. However, predominantly, the epoxy ring is ring-opened so as to generate a secondary hydroxyl group and is connected to a hydroxyl group of ascorbic acid. Therefore, a compound in which $R^1$ is $R^3$—O—$CH_2$—CH(OH)—$CH_2$— or $R^6$—CH(OH)—$CH_2$— is generated more easily than a compound in which $R^1$ is $R^4$—O—$CH_2$—CH($CH_2$OH)— or $R^5$—CH($CH_2$OH)—, and a compound in which $R^2$ is $R^7$—O—$CH_2$—CH(OH)—$CH_2$— or $R^{10}$—CH(OH)—$CH_2$— is generated more easily than a compound in which $R^2$ is $R^8$—O—$CH_2$—CH($CH_2$OH)— or $R^9$—CH($CH_2$OH)—. That is, a compound of the formula (I) in which $R^1$ is H, alkyl group having 1 to 22 carbon atoms, alkenyl group having 2 to 22 carbon atoms, benzyl group, $R^3$—O—$CH_2$—CH(OH)—$CH_2$—, $R^6$—CH(OH)—$CH_2$— or hydroxycyclohexyl group, and $R^2$ is H, alkyl group having 1 to 22 carbon atoms, alkenyl group having 2 to 22 carbon atoms, benzyl group, $R^7$—O—$CH_2$—CH(OH)—$CH_2$—, $R^{10}$—CH(OH)—$CH_2$— or hydroxycyclohexyl group is generated more easily, as the ascorbic acid derivative or salt thereof according to Claim 1.

The invention of Claim 2 is an ascorbic acid derivative or salt thereof according to Claim 1 which is characterized by that $R^1$ is an alkyl group having 1 to 22 carbon atoms, alkenyl group having 2 to 22 carbon atoms, benzyl group, $R^3$—O—$CH_2$—CH(OH)—$CH_2$—, $R^4$—O—$CH_2$—CH($CH_2$OH)—, $R^5$—CH($CH_2$OH)—, $R^6$—CH(OH)—$CH_2$— or hydroxycyclohexyl group, and $R^2$ is an alkyl group having 1 to 22 carbon atoms, alkenyl group having 2 to 22 carbon atoms, benzyl group, $R^7$—O—$CH_2$—CH(OH)—$CH_2$—, $R^8$—O—$CH_2$—CH($CH_2$OH)—, $R^9$—CH($CH_2$OH)—, $R^{10}$—CH(OH)—$CH_2$— or hydroxycyclohexyl group, in the above-described general formula (I). Here, $R^3$ to $R^{10}$ represent the same meanings as defined for the invention according to Claim 1.

The above-described ascorbic acid derivatives or salts thereof of the present invention are more excellent in stability over time by far than ascorbic acid. Among them, those in which $R^2$ is an alkyl group having 1 to 22 carbon atoms, alkenyl group having 2 to 22 carbon atoms, benzyl group, $R^7$—O—$CH_2$—CH(OH)—$CH_2$—, $R^8$—O—$CH_2$—CH($CH_2$OH)—, $R^9$—CH($CH_2$OH)—, $R^{10}$—CH(OH)—$CH_2$— or hydroxycyclohexyl group (namely, $R^2$ is not H) are preferable from the standpoint that they show more excellent stability over time than those in which $R^2$ is H and $R^1$ is an alkyl group having 1 to 22 carbon atoms, alkenyl group having 2 to 22 carbon atoms, benzyl group, $R^3$—O—$CH_2$—CH(OH)—$CH_2$—, $R^4$—O—$CH_2$—CH($CH_2$OH)—, $R^5$—CH($CH_2$OH)—, $R^6$—CH(OH)—$CH_2$— or hydroxycyclohexyl group. Further, those in which both $R^1$ and $R^2$ are substituted by the above-described groups are excellent particularly in stability over time and particularly preferable in this regard. Claim 2 corresponds to this particularly preferable embodiment.

Specific examples of the ascorbic acid derivative represented by the general formula (I) include compounds shown below, but the scope of the present invention should not be limited to those shown below.

In the following examples:

the glyceryl denotes $HOCH_2$—CH(OH)—$CH_2$— or $HOCH_2$—CH($CH_2$OH)—, the alkyl glyceryl group denotes R—O—$CH_2$—CH(OH)$CH_2$— or R—O—$CH_2$—CH($CH_2$OH)— (R represents an alkyl group), the alkyl group denotes a methyl group, ethyl group, propyl group, isopropyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, behenyl group or the like, the alkenyl group denotes a vinyl group, allyl group, butenyl group, isobutenyl group, crotyl group, octenyl group, decenyl group, dodecenyl group or the like, the hydroxyalkyl group denotes R—$CH_2$—CH(OH)— or R—CH(OH)—$CH_2$— (R represents an alkyl group), and includes, for example, a hydroxyethyl group, hydroxypropyl group, hydroxybutyl group, hydroxypentyl group, hydroxyhexyl group, hydroxyheptyl group, hydroxyoctyl group, hydroxynonyl group, hydroxydecyl group, hydroxyundecyl group, hydroxydodecyl group, hydroxytridecyl group, hydroxytetradecyl group, hydroxypentadecyl group, hydroxyhexadecyl group, hydroxyheptadecyl group, hydroxyoctadecyl group, hydroxynonadecyl group, hydroxyeicosyl group and hydroxybehenyl group.

(1) 3-O-glyceryl ascorbic acid 3-O-alkylglyceryl ascorbic acid, for example, 3-O-methylglyceryl ascorbic acid, 3-O-eicosylglyceryl ascorbic acid, 3-O-alkenylglyceryl ascorbic acid, for example, 3-O-allylglyceryl ascorbic acid, 3-O-crotylglyceryl ascorbic acid, 3-O-vinylglyceryl ascorbic acid, 3-O-isobutenylglyceryl ascorbic acid, 3-O-octenylglyceryl ascorbic acid, 3-O-decenylglyceryl ascorbic acid, 3-O-dodecenylglyceryl ascorbic acid and 3-O-phenylglyceryl ascorbic acid, (2) 2-O-glyceryl ascorbic acid 2-O-alkylglyceryl ascorbic acid, for example, 2-O-methylglyceryl ascorbic acid, 2-O-eicosylglyceryl ascorbic acid, 2-O-alkenylglyceryl ascorbic acid, for example, 2-O-allylglyceryl ascorbic acid, 2-O-dodecenylglyceryl ascorbic acid and 2-O-phenylglyceryl ascorbic acid, (3) 2,3-di-O-glyceryl ascorbic acid 2,3-di-O-alkylglyceryl ascorbic acid, 2,3-di-O-alkenylglyceryl ascorbic acid and 2,3-di-O-phenylglyceryl ascorbic acid, (4) 3-O-hydroxyalkyl ascorbic acid and 3-O-hydroxyphenylethyl ascorbic acid (5) 2-O-hydroxyalkyl ascorbic acid and 2-O-hydroxyphenylethyl ascorbic acid (6) 2,3-di-O-hydroxyalkyl ascorbic acid and 2,3-di-O-hydroxyphenylethyl ascorbic acid (7) 3-O-glyceryl-2-O-alkylglyceryl ascorbic acid, 3-O-glyceryl-2-O-alkenylglyceryl ascorbic acid and 3-O-glyceryl-2-O-phenylglyceryl ascorbic acid (8) 3-O-glyceryl-2-O-hydroxyalkyl ascorbic acid and 3-O-glyceryl-2-O-hydroxyphenyl ascorbic acid (9) 3-O-glyceryl-2-O-alkyl ascorbic acid and 3-O-glyceryl-2-O-alkenyl ascorbic acid
(10) 3-O-alkylglyceryl-2-O-alkylglyceryl ascorbic acid (here, 3-alkyl and 2-alkyl are different each other), 3-O-alkylglyceryl-2-O-alkenylglyceryl ascorbic acid and 3-O-alkylglyceryl-2-O-phenylglyceryl ascorbic acid
(11) 3-O-alkylglyceryl-2-O-hydroxyalkylglyceryl ascorbic acid, 3-O-alkenylglyceryl-2-O-hydroxyalkylglyceryl ascorbic acid, 3-O-alkylglyceryl-2-O-hydroxyalkenylglyceryl ascorbic acid, 3-O-alkenylglyceryl-2-O-hydroxyalkenylglyceryl ascorbic acid and 3-O-alkylglyceryl-2-O-phenylglyceryl ascorbic acid,
(12) 3-O-alkylglyceryl-2-O-alkyl ascorbic acid and 3-O-alkylglyceryl-2-O-alkenyl ascorbic acid,
(13) 3-O-hydroxyalkyl-2-O-alkyl ascorbic acid and 3-O-hydroxyalkyl-2-O-alkenyl ascorbic acid,
(14) 3-O-hydroxyalkyl-2-O-alkylglyceryl ascorbic acid and 3-O-hydroxyalkyl-2-O-alkenylglyceryl ascorbic acid,
(15) 3-O-hydroxyalkyl-2-O-hydroxyalkyl ascorbic acid and 3-O-hydroxyalkyl-2-O-hydroxyphenylethyl ascorbic acid,
(16) 3-O-hydroxycyclohexyl ascorbic acid, 2-O-hydroxycyclohexyl ascorbic acid, 3-O-glyceryl-2-O-benzyl ascorbic acid and 2-O-glyceryl-3-O-benzyl ascorbic acid.

The invention of Claim 3 is an ascorbic acid derivative or salt thereof according to Claim 1 which is characterized by that $R^1$ is H, or $R^3$—O—$CH_2$—CH(OH)—$CH_2$—, $R^4$—O—$CH_2$—CH($CH_2$OH)—, $R^5$—CH($CH_2$OH)—, $R^6$—CH(OH)—$CH_2$— or hydroxycyclohexyl group, and $R^2$ is H, or $R^7$—O—$CH_2$—CH(OH)—$CH_2$—, $R^8$—O—$CH_2$—CH($CH_2$OH)—, $R^9$—CH($CH_2$OH)—, $R^{10}$—CH(OH)—$CH_2$— or hydroxycyclohexyl group (here, at least one of $R^1$ and $R^2$ is not H), in the above-described general formula (I). Here, $R^3$, $R^4$, $R^5$ and $R^6$ represent the same meanings as defined for the invention according to Claim 1. The ascorbic acid derivative or salt thereof according to this embodiment can be produced easily by a production method of the present invention described later. When $R^1$ or $R^2$ is H, it can be converted into a salt. By converting into a salt, applicability to a cosmetic is enhanced in some cases, for example, by improvement of stability in a cosmetic.

The ascorbic acid derivative of Claim 3 can be obtained by reacting ascorbic acid with an epoxy compound selected from glycidol, specifically structured alkyl glycidyl ether, alkenyl glycidyl ether, phenyl glycidyl ether, ethylene oxide, epoxy alkane, epoxy alkene, styrene oxide and alicyclic epoxy, thereby position-selective etherification only hydroxyl groups at 2-position and/or 3-position among four hydroxyl groups situated at 2-, 3-, 5- and 6-positions of ascorbic acid, as described later.

Particularly, an ascorbic acid derivative of Claim 3 in which $R^1$ is H, $R^3$—O—$CH_2$—CH(OH)—$CH_2$— or $R^4$—O—$CH_2$—CH($CH_2$OH)—, and $R^2$ is H, $R^7$—O—$CH_2$—CH(OH)—$CH_2$— or $R^8$—O—$CH_2$—CH($CH_2$OH)— (here, at least one of $R^1$ and $R^2$ is not H), in the formula (I) can be obtained by reacting ascorbic acid with glycidol, specifically structured alkyl glycidyl ether, alkenyl glycidyl ether or phenyl glycidyl ether.

An ascorbic acid derivative or salt thereof of Claim 3 in which $R^1$ is H, $R^5$—CH($CH_2$OH)— or $R^6$—CH(OH)—$CH_2$— and $R^2$ is H, $R^9$—CH($CH_2$OH)— or $R^{10}$—CH(OH)—$CH_2$— (here, at least one of $R^1$ and $R^2$ is not H), in the formula (I) can be obtained by reacting ascorbic acid with ethylene oxide, specifically structured epoxy alkane, 1,2-epoxycyclohexane or styrene oxide.

In an ascorbic acid derivative of the above-described formula (I) in which $R^1$ or $R^2$ is H, a hydrogen ion generated by dissociation of H can be substituted by a positive ion such as a metal ion, ammonium ion and the like to form a salt, and this salt is also included in the scope of the present invention. This salt includes inorganic salts and organic salts. Inorganic salts include salts of an alkali metal such as sodium and potassium, salts of an alkaline earth metal such as calcium and magnesium, ammonium salt and the like. Organic salts include a diethanolamine salt, triethanolamine salt, basic amino acid salt and the like. Formation of the salt can be carried out by the same method as for known salt formation method such as neutralization of an aqueous solution of an ascorbic acid derivative in which $R^1$ or $R^2$ is H with a basic substance.

The ascorbic acid derivative or salt thereof of the present invention has excellent functions originally owned by ascorbic acid such as a whitening effect, collagen production promoting effect and the like, has a moisturizing effect, and shows good stability and little coloration, odor change, activity lowering and the like even in storage over a long period of time. Particularly, ascorbic acid derivatives (A) to (E) listed below show a better whitening effect and thus are eligible.

(A) An ascorbic acid derivative according to Claim 1, that is, an ascorbic acid derivative represented by the formula (I) in which one of $R^1$ or $R^2$ is HO—$CH_2$—CH(OH)—$CH_2$— and the other of $R^1$ or $R^2$ is an alkyl group having 4 to 16 carbon atoms (Claim 4). Among compounds of Claim 4, compounds in which the other of $R^1$ or $R^2$ is an alkyl group having 6 to 12 carbon atoms show a further excellent whitening effect. Especially, compounds in which $R^{11}$ is HO—$CH_2$—CH(OH)—$CH_2$— and $R^2$ is an alkyl group having 6 to 12 carbon atoms show a particularly excellent whitening effect.

(B) An ascorbic acid derivative according to Claim 1, that is, an ascorbic acid derivative represented by the formula (I) in which one of $R^1$ or $R^2$ is $R^a$—O—$CH_2$—CH(OH)—$CH_2$— ($R^a$ represents an alkyl group having 2 to 20 carbon atoms) and the other of $R^1$ or $R^2$ is an alkyl group having 2 to 20 carbon atoms (Claim 5). Among compounds of Claim 5, compounds in which $R^a$ is a butyl group and the other of $R^1$ or $R^2$ is an alkyl group having 4 to 8 carbon atoms and compounds in which $R^a$ is an alkyl group having 12 to 16 carbon atoms and the other of $R^1$ or $R^2$ is an alkyl group having 1 to 8 carbon atoms show a further excellent whitening effect. Especially, compounds in which $R^1$ is $CH_3(CH_2)_3$—$CH_2$—CH(OH)—$CH_2$— and $R^2$ is an alkyl group having 4 to 8 carbon atoms and compounds in which $R^1$ is $R^a$—O—$CH_2$—CH(OH)—$CH_2$— ($R^a$ represents an alkyl group having 12 to 16 carbon atoms) and $R^2$ is an alkyl group having 1 to 8 carbon atoms show a particularly excellent whitening effect.

(C) An ascorbic acid derivative according to Claim 1, that is, an ascorbic acid derivative represented by the formula (I) in which one of $R^1$ or $R^2$ is $R^b$—CH($CH_2$OH)— ($R^b$ represents an alkyl group having 6 to 20 carbon atoms) and the other of $R^1$ or $R^2$ is an alkyl group having 4 to 6 carbon atoms or $R^c$—CH($CH_2$OH)— ($R^c$ represents an alkyl group having 4 to 6 carbon atoms)(Claim 6). Among compounds of Claim 6, compounds in which $R^b$ is an alkyl group having 8 to 12 carbon atoms show a further excellent whitening effect. Especially, compounds in which $R^1$ is $R^b$—CH($CH_2$OH)— ($R^b$ represents an alkyl group having 8 to 12 carbon atoms) show a particularly excellent whitening effect.

(D) An ascorbic acid derivative according to Claim 1, that is, an ascorbic acid derivative represented by the formula (I) in which one of $R^1$ or $R^2$ is $R^e$—O—$CH_2$—CH(OH)—$CH_2$— ($R^e$ represents a phenyl group)(Claim 7). Among compounds of Claim 7, compounds in which $R^1$ is $R^e$—O—$CH_2$—CH(OH)—$CH_2$— and $R^2$ is a benzyl group or $R^f$—O—$CH_2$—CH(OH)—$CH_2$— ($R^f$ represents a phenyl group) show a particularly excellent whitening effect.

(E) An ascorbic acid derivative according to Claim 1, that is, an ascorbic acid derivative represented by the formula (I) in which one of $R^1$ or $R^2$ is HO—$CH_2$—CH(OH)—$CH_2$— and the other of $R^1$ or $R^2$ is $R^d$—O—$CH_2$—CH(OH)—$CH_2$— ($R^d$ represents an alkyl group having 10 to 16 carbon atoms)(Claim 8). Among compounds of Claim 8, compounds in which $R^1$ is HO—$CH_2$—CH(OH)—$CH_2$— and $R^2$ is $R^d$—O—$CH_2$—CH(OH)—$CH_2$— show a particularly excellent whitening effect.

Moreover, an ascorbic acid derivative or salt thereof of the present invention in which $R^1$ is $R^3$—O—$CH_2$—CH(OH)—$CH_2$—, $R^4$—O—$CH_2$—CH($CH_2OH$)—, $R^5$—CH($CH_2OH$)— or $R^6$—CH(OH)—$CH_2$—, and/or, $R^2$ is $R^7$—O—$CH_2$—CH(OH)—$CH_2$—, $R^8$—O—$CH_2$—CH($CH_2OH$)—, $R^9$—CH($CH_2OH$)— or $R^{10}$—CH(OH)—$CH_2$—, and $R^3$, $R^4$, $R^5$, $R^6$, $R^7$, $R^8$, $R^9$ or $R^{10}$ is a long chain alkyl group or long chain alkenyl group, particularly, that having 8 or more carbon atoms, in the formula (I), has a characteristic that it can produce an emulsion even if a surfactant of polyoxyethylene type, such as polyoxyethylene alkylether, is not used, and also has a characteristic that it is advantageous in producing an agent.

An ascorbic acid derivative or salt thereof of the present invention in which $R^1$ is $R^3$—O—$CH_2$—CH(OH)—$CH_2$—, $R^4$—O—$CH_2$—CH($CH_2OH$)—, $R^5$—CH($CH_2OH$)— or $R^6$—CH(OH)—$CH_2$—, and $R^3$, $R^4$, $R^5$, $R^6$ and $R^2$ represent H, alkyl or alkenyl, and the total number of carbon atoms of $R^3$, $R^4$, $R^5$, $R^6$ and $R^2$ is 4 or less, in the formula (I), an ascorbic acid derivative or salt thereof of the present invention in which $R^2$ is $R^7$—O—$CH_2$—CH(OH)—$CH_2$—, $R^8$—O—$CH_2$—CH($CH_2OH$)—, $R^9$—CH($CH_2OH$)— or $R^{10}$—CH(OH)—$CH_2$—, and $R^7$, $R^8$, $R^9$, $R^{10}$ and $R^1$ represent H, alkyl or alkenyl, and the total number of carbon atoms of $R^7$, $R^8$, $R^9$, $R^{10}$ and $R^1$ is 4 or less, in the formula (I), and an ascorbic acid derivative or salt thereof of the present invention in which $R^1$ is $R^3$—O—$CH_2$—CH(OH)—$CH_2$—, $R^4$—O—$CH_2$—CH($CH_2OH$)—, $R^5$—CH($CH_2OH$)— or $R^6$—CH(OH)—$CH_2$—, $R^2$ is $R^7$—O—$CH_2$—CH(OH)—$CH_2$—, $R^8$—O—$CH_2$—CH($CH_2OH$)—, $R^9$—CH($CH_2OH$)— or $R^{10}$—CH(OH)—$CH_2$—, and $R^3$, $R^4$, $R^5$, $R^6$, $R^7$, $R^8$, $R^9$ and $R^{10}$ represent H, alkyl or alkenyl and the total number of carbon atoms of $R^3$, $R^4$, $R^5$, $R^6$, $R^7$, $R^8$, $R^9$ and $R^{10}$ is 4 or less, in the formula (I) (Claim 9) give a particularly excellent moisturizing effect. Thus, from this standpoint, they are used suitably as a component of a cosmetic. That is, as the method for improving the moisturizing property of a cosmetic, a method of compounding the said ascorbic acid derivative or salt thereof into components of a cosmetic is mentioned.

This moisturizing effect is larger when it is compounded in an amount of 1 to 20% by weight (based on the total weight of cosmetic or the like) into a cosmetic or the like. Particularly, when it is compounded in an amount of 5 to 20% by weight, an excellent moisturizing effect is manifested (Claim 14).

Further, the ascorbic acid derivative of the present invention has a character that it has a collagen production promoting effect which is equivalent to or higher than the effect of ascorbic acid. Further, this collagen production promoting effect increases over time. Since the collagen production promoting effect of ascorbic acid and known ascorbic acid derivatives lowers over time, the ascorbic acid derivative of the present invention is particularly excellent in the point of durability of the collagen production promoting effect.

An ascorbic acid derivative or salt thereof in which 2-position and 3-position are position-selectively etherified such as an ascorbic acid derivative represented by the above-described formula (I) or the like can be produced by a method of reacting ascorbic acid with an epoxy compound selected from glycidol, alkyl glycidyl ether, alkenyl glycidyl ether, phenyl glycidyl ether, ethylene oxide, epoxy alkane, epoxy alkene, styrene oxide and alicyclic epoxy, thereby position-selectively etherifying only hydroxyl groups at 2-position and/or 3-position among four hydroxyl groups situated at 2-, 3-, 5- and 6-positions of ascorbic acid. The method of position-selective etherification is not particularly restricted, and for example, there is mentioned a method in which hydroxyl groups at 5-position and 6-position are protected by a protective group, then, an etherifying reaction is conducted. As the reaction of protecting hydroxyl groups at 5-position and 6-position with a protective group, there are mentioned, for example, methods described in paragraph 0017 and paragraph 0029 of JP-A No. 8-81462. They include a method in which ascorbic acid is reacted at room temperature in the presence of acetone, in the presence of a catalytic amount of anhydrous hydrogen chloride or acetyl chloride, to give 5,6-O-isopropylidene-L-ascorbic acid.

As a result of investigation, however, the present inventors have found that when ascorbic acid is reacted with an epoxy compound selected from glycidol, alkyl glycidyl ether, alkenyl glycidyl ether, phenyl glycidyl ether, ethylene oxide, epoxy alkane, epoxy alkene, styrene oxide and alicyclic epoxy, an addition reaction first occurs selectively to 2-position or 3-position to obtain a 2-position or 3-position adduct even in the case of no protection of hydroxyl groups at 5-position and 6-position with a protective group. Further, the present inventors have also found that by reacting the thus obtained 2-position or 3-position adduct further with an epoxy compound selected from glycidol, alkyl glycidyl ether, alkenyl glycidyl ether, phenyl glycidyl ether, ethylene oxide, epoxy alkane, epoxy alkene, styrene oxide and alicyclic epoxy, remaining hydroxyl groups at 2-position or 3-position can be etherified, thereby obtaining a compound in which only both 2-position and 3-position are position-selectively etherified. Here, the epoxy compound used for etherification of 2-position and the epoxy compound used for etherification of 3-position may be identical or different from each other. According to this reaction, a process of protecting hydroxyl groups at 5-position and 6-position with a protective group is not necessary. Thereby, the number of processes decreases to give a simple reaction. Therefore, this method is preferable as the production method of an ascorbic acid derivative or salt thereof in which 2-position and 3-position are position-selectively etherified, such as an ascorbic acid derivative of the above-described formula (I) or the like.

Then, in the present invention, Claim 10 provides this preferable production method, that is, a production method of an ascorbic acid derivative or salt thereof which is characterized by having a process of reacting ascorbic acid with an epoxy compound selected from glycidol, alkyl glycidyl ether, alkenyl glycidyl ether, phenyl glycidyl ether, ethylene oxide, epoxy alkane, epoxy alkene, styrene oxide and alicyclic epoxy without protecting hydroxyl groups at 5-position and 6-position of ascorbic acid.

The above-described epoxy compound can be selected from a group consisting of compounds represented by the following formula (II), compounds represented by the following formula (III), and 1,2-epoxycyclohexane. In the case of use of these specific epoxy compounds, position-selective etherification is more remarkable. The present invention provides this production method as Claim 11.

(Chemical formula 2)

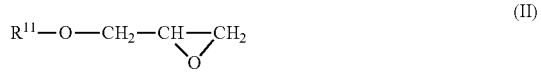
(II)

[wherein, $R^{11}$ represents H, alkyl group having 1 to 22 carbon atoms, alkenyl group having 2 to 22 carbon atoms or phenyl group.].

(Chemical formula 3)

(III)

[wherein, $R^{12}$ represents H, alkyl group having 1 to 20 carbon atoms, alkenyl group having 2 to 20 carbon atoms or phenyl group.].

According to a method of using this specifically structured epoxy compound, the above-described effect is more excellent, a reaction of forming a protective group, and the like are not necessary, and only 2-position or 3-position can be position-selectively etherified in only one reaction, thus, the above-described ascorbic acid derivative or salt thereof of the present invention can be produced with high production efficiency.

Examples of the compound represented by the formula (II) include glycidol, methyl glycidyl ether, ethyl glycidyl ether, propyl glycidyl ether, isopropyl glycidyl ether, butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, heptadecyl glycidyl ether, octadecyl glycidyl ether, nonadecyl glycidyl ether, vinyl glycidyl ether, allyl glycidyl ether, butenyl glycidyl ether, isobutenyl glycidyl ether, crotyl glycidyl ether, octenyl glycidyl ether, decenyl glycidyl ether, dodecenyl glycidyl ether and phenyl glycidyl ether.

Examples of the epoxy alkane represented by the formula (III) include ethylene oxide, methyl oxirane, ethyl oxirane, propyl oxirane, isopropyl oxirane, butyl oxirane, pentyl oxirane, hexyl oxirane, heptyl oxirane, octyl oxirane, nonyl oxirane, decyl oxirane, undecyl oxirane, dodecyl oxirane, tridecyl oxirane, tetradecyl oxirane, pentadecyl oxirane, hexadecyl oxirane, heptadecyl oxirane, octadecyl oxirane and nonadecyl oxirane. Examples of the epoxy alkene represented by the formula (III) include isopropylene oxirane butene oxirane, pentene oxirane, hexene oxirane, heptene oxirane, octene oxirane, nonene oxirane, decene oxirane, undecene oxirane, dodecene oxirane, tridecene oxirane, tetradecene oxirane, pentadecene oxirane, hexadecene oxirane, heptadecene oxirane, octadecene oxirane and nonadecene oxirane.

As the alkyl glycidyl ether, commercially available products may be used, and it can be obtained also by reacting alcohols with epihalo(chloro)hydrin.

In ascorbic acid used in the method of producing an ascorbic acid derivative or salt thereof of the present invention, the steric structure of carbon at 4-position and 5-position may be either S-configuration or R-configuration. Further, the epoxy compound such as glycidol, alkyl glycidyl ether, alkenyl glycidyl ether, epoxy alkane, epoxy alkene or the like may be an S-body, R-body or a mixture thereof.

The ascorbic acid derivative or salt thereof of the formula (I) can be produced also by a method in which 3-halo-1,2-propanediol such as 3-chloro-1,2-propanediol is used instead of glycidol and reacted with ascorbic acid, thereby etherifying only 2-position and/or 3-position of ascorbic acid. In this case, it is necessary to further add a basic substance to the reaction system for de-halogenation.

The reaction constituting the invention of Claim 10 or Claim 11 can be carried out in a solvent. The solvent is not particularly restricted and examples of the solvent include water, lower alcohols such as methanol, ethanol and isopropanol, dimethyl sulfoxide (DMSO), N,N-dimethylformamide (DMF), dioxane, tetrahydrofuran (THF) and mixtures thereof. Here, in the case of use of a compound of the formula (II) in which $R^{11}$ represents H, alkyl group having 1 to 8 carbon atoms or alkenyl group having 2 to 8 carbon atoms or a compound of the formula (III) in which $R^{12}$ represents H, alkyl group having 1 to 8 carbon atoms or alkenyl group having 2 to 8 carbon atoms, as the above-described epoxy compound, an aqueous solvent is preferable from the standpoint of reduction of load on environments, low cost and safety (Claim 12). Example of the aqueous solvent include water as well as a mixed solvent mainly composed of water and containing a solvent compatible with water.

Although the reaction temperature is not particularly restricted, preferably it is 30 to 100° C., and 40 to 90° C. is more preferable. The pH of the reaction solvent is not particularly restricted. Under acidic condition, particularly pH 2 to 6, is preferable in the case of production of the above-described ascorbic acid derivative or salt thereof in which 2-position of the ascorbic acid structure is H. Under alkaline condition, particularly pH 8 to 11, is preferable in the case of production of the above-described ascorbic acid derivative or salt thereof in which 3-position of the ascorbic acid structure is H.

Since ascorbic acids are easily oxidized, it is preferable to substitute the atmosphere in the reaction system with an inert gas such as argon, nitrogen or helium. By carrying out the reaction under an inert gas atmosphere, coloration, odor change and the like can be lowered. As the catalyst, alkali catalysts such as sodium hydrogen carbonate, and acid catalysts such as sulfuric acid can be used. It is also possible to use a phase transfer catalyst such as tetrabutyl ammonium bromide. In conducting the reaction, a catalyst may be dissolved in a small amount of water before addition, for sufficient mixing thereof. Though the method of mixing raw materials such as ascorbic acid and epoxy compounds is not particularly restricted, it is also possible to drop the epoxy compound into the reaction system.

Though the use amount of the epoxy compound with respect to ascorbic acid is not particularly restricted, it is preferably 0.5 to 5 mol with respect to 1 mol of ascorbic acid. When the use amount of the epoxy compound with respect to ascorbic acid is smaller, the position-selectivity of the addition reaction, that is, selective addition to 2-position or 3-position is more remarkable. In the case of addition to only one of 2-position or 3-position, it is preferably in the range of about 0.5 to 1.5 mol.

A compound in which an epoxy compound is added to both 2-position and 3-position can be obtained, for example, by a method in which an epoxy compound is added to only one of the positions of the ascorbic acid under the above-described condition (about 0.5 to 1.5 mol) to obtain an adduct of addition, then, purification is performed to separate the adduct by a method described later and the like, followed by reacting this adduct with about 0.5 to 1.5 mol of epoxy compound. By changing the epoxy compound to be used in the reaction before purification and the reaction after purification, a compound in which different epoxy compounds are added to both 2-position and 3-position can be obtained.

An ascorbic acid derivative or salt thereof of the general formula (I) in which $R^1$ or $R^2$ is an alkyl group having 1 to 22 carbon atoms, alkenyl group having 2 to 22 carbon atoms or benzyl group can be obtained by performing the reaction of Claim 11 at a use amount of an epoxy compound with respect to ascorbic acid in the range of about 0.5 to 1.5 mol thereby obtaining an ascorbic acid derivative in which only one of $R^1$ or $R^2$ is etherified, then, alkylating, alkenylating or benzylating remaining hydroxyl groups among hydroxyl groups at 2-position or 3-position. The alkylation, alkenylation or benzylation can be carried out by known methods, for example, a reaction with a halogenated alkyl, halogenated alkenyl, halogenated benzyl and the like. In the case of a halogenated allyl, halogenated crotyl, halogenated benzyl and the like, the reaction can be carried out in an aqueous solvent.

The ascorbic acid derivative or salt thereof produced as described above can be purified by means such as column chromatography using silica gel, column chromatography using a resin such as an ion exchange resin, treatment with activated carbon, extraction, distillation, crystallization and the like.

The ascorbic acid derivative or salt thereof of the present invention is suitably used as a component of a skin external agent and various cosmetics such as a hair cosmetic. Claim 13 provides a cosmetic obtained by compounding an ascorbic acid derivative or salt thereof according to any one of Claims 1 to 9.

As described above, the ascorbic acid derivative or salt thereof of the present invention has excellent effects originally owned by ascorbic acid such as a whitening effect and collagen production promoting effect. In addition, the ascorbic acid derivative or salt thereof of the present invention has a moisturizing effect, and shows stability and little coloration, odor change, activity lowering and the like even in storage over a long period of time. Thus, by allowing this ascorbic acid derivative or salt thereof to be contained as a component, a skin external agent and various cosmetics such as a hair cosmetic having an excellent whitening effect, collagen production promoting effect, moisturizing effect and the like and excellent also in stability over time can be obtained. Further, it can also be utilized as a food additive, a feed or the like.

In the case of use of an ascorbic acid derivative or salt thereof of the present invention as a moisturizing agent, the compounding amount in various cosmetics is preferably 1 to 20% by weight as described above. In the case of other applications, the range of the compounding amount thereof varies depending on the application of a cosmetic. Though the amount is not particularly restricted, usually, it is preferably in the range of 0.01 to 20% by weight. When less than 0.01% by weight, the effects of the ascorbic acid derivative or salt thereof of the present invention such as a whitening action cannot be manifested sufficiently, in many cases. In contrast, when over 20% by weight, an effect corresponding to the compounding amount cannot be obtained in many cases. Further, there may be a risks of decomposition of the agent.

In the cosmetic of the present invention, components usually used for cosmetic, for example, oily raw materials, surfactants, polymer compounds, ultraviolet absorbers, medicines, sequestering agents, antioxidants and the like can be appropriately compounded, in addition to the essential components. Though the ascorbic acid derivative or salt thereof of the present invention acts also as a moisturizing agent, other moisturizing agents can be appropriately compounded into the cosmetic of the present invention.

Examples of the oily raw materials include oils and fats such as olive oil, camellia oil, macadamia nut oil, tea oil, castor oil and tri(caprone/capryl) glyceryl, waxes such as jojoba oil, carnauba wax, candelilla wax, lanolin and bees wax, hydrocarbons such as liquid paraffin, paraffin, vaseline, ceresin, microcrystalline wax and squalane, fatty acids such as lauric acid, myristic acid, palmitic acid, stearic acid, behenic acid and isostearic acid, higher alcohols such as cetyl alcohol, stearyl alcohol and isostearyl alcohol, esters such as isopropyl myristate, 2-octyldodecyl myristate, cetyl 2-ethylhexanoate, diisostearyl malate and tri-2-ethylhexanoin, and silicones such as methyl polysiloxane, methyphenyl polysiloxane and decamethyl cyclopenta siloxane.

Examples of the surfactants include anionic surfactants such as higher fatty acid soaps, polyoxyethylene alkyl ether sulfate, acyl-N-methyl taurate, N-acyl amino acid salts and alkyl phosphates, cationic surfactants such as alkyl trimethyl ammonium chloride and dialkyl dimethyl ammonium chloride, ampholytic surfactants such as alkyl dimethyl aminoacetic acid betaine, alkyl amide aminoacetic acid betaine and 2-alkyl-N-carboxy-N-hydroxy imidazolynium betaine, and nonionic surfactants such as polyoxyethylene alkyl ether, polyethylene glycol fatty acid ester, poly-hydric alcohol fatty acid ester and polyether-modified silicone.

Examples of the other moisturizing agents include glycerin, propylene glycol, maltitol, sorbitol, 1,3-butylene glycol, sodium lactate, polyethylene glycol, sodium pyrrolidone carboxylate and sodium hyaluronate.

Examples of the polymer compounds include carboxy vinyl polymer, carboxy methylcellulose sodium, xanthan gum, polyvinyl alcohol and dimethylpolysiloxane polymer.

Examples of the antioxidants include vitamin E, tannin and BHT (butylhydroxytoluene).

The form of the cosmetic of the present invention is arbitrary, and any of a solution system, solubilization system, emulsion system, gel system, powder dispersion system, water-oil two-layer system and the like are possible. According to the intended cosmetic product, an ascorbic acid derivative or salt thereof of the above-described general formula and the above-described optional compounding components can be compounded.

EFFECT OF THE INVENTION

The ascorbic acid derivative or salt thereof of the above-described general formula (I) of the present invention has excellent effects originally owned by ascorbic acid such as a whitening effect and collagen production promoting effect, has a moisturizing effect, has excellent stability, and shows little coloration, odor change, activity lowering and the like even in storage over a long period of time. Thus, by compounding this compound into a skin external agent and a cosmetic such as a hair cosmetic, a cosmetic which is excellent in whitening effect, moisturizing effect and the like and also excellent in stability in storage over a long period of time can be obtained. The cosmetic of the present invention is excellent in whitening effect, moisturizing effect and the like and also excellent in stability in storage over a long period of time, and suitably used as a whitening cosmetic, moisturizing cosmetic or the like.

According to the production method of the present invention, an ascorbic acid derivative or salt thereof of the above-described general formula (I) can be produced by simply reacting ascorbic acid and an epoxy compound without forming a protective group, and thus, the ascorbic acid derivative or salt thereof of the present invention can be produced easily and cheaply.

EMBODIMENTS FOR CARRYING OUT THE INVENTION

Next, specific embodiments for carrying out the present invention will be explained concretely by examples. The scope of the present invention is not limited to the examples.

EXAMPLE 1

Synthesis of 3-O-glyceryl ascorbic acid

Under an argon atmosphere, L-ascorbic acid (300 g) and sodium hydrogen carbonate (42.9 g) were added to water and the resultant mixture was stirred at room temperature for 30 minutes, then, glycidol (126 g) was added thereto. Thereafter, the mixture was heated up to 50° C. and stirred for 5 hours. Thereto, methanol was added and filtration was performed. The filtrate was concentrated under reduced pressure, and 457 g of the resultant residue was subjected to silica gel column chromatography. Elution was performed with chloroform/methanol/water(volume ratio:65/35/5), and concentration was performed under reduced pressure to obtain 3-O-glyceryl ascorbic acid (296 g).

On the resultant product, high resolution mass analysis, infrared absorption spectrum, $^1$H-NMR and $^{13}$C-NMR measurements were carried out, and based on the measurement results, this product was confirmed to be 3-O-glyceryl ascorbic acid of the following structural formula.

Also in examples shown later, high resolution mass analysis, infrared absorption spectrum, $^1$H-NMR and $^{13}$C-NMR measurements were carried out on the resultant products, and based on the measurement results, the product was confirmed to be an ascorbic acid derivative represented by the structural formula or compound name shown in each example. The measurement results of high resolution mass analysis, infrared absorption spectrum, $^1$H-NMR and $^{13}$C-NMR measurements on the product obtained in the examples shown later are shown in Tables 1 to 8.

(Chemical formula 4)

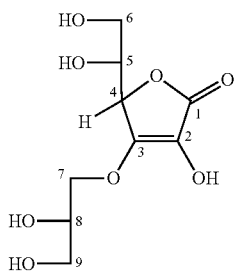

In this structural formula, carbon atoms, and hydrogen atoms connected to the carbon atoms are abbreviated. For example, in this formula, carbons exist at 1- to 4-positions, $CH_2$ groups exist at 6-, 7- and 9-positions, and CH groups exist at 5- and 8-positions. Also in the following structural formulae, carbon atoms and hydrogen atoms are abbreviated like in this formula.

EXAMPLE 2

Synthesis of Sodium 3-O-glyceryl ascorbate

One gram of 3-O-glyceryl ascorbic acid obtained according to the same manner as in Example 1 was dissolved in water, and 336 mg of sodium hydrogen carbonate was added thereto. The mixture was stirred for 30 minutes, then, concentrated under reduced pressure to obtain 1.07 g of sodium 3-O-glyceryl ascorbate.

(Chemical formula 5)

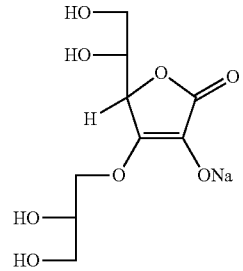

EXAMPLE 3

Synthesis of 2-O-glyceryl ascorbic acid

Under an argon atmosphere, L-ascorbic acid (10.0 g) and sodium hydrogen carbonate (9.54 g) were added to water and the resultant mixture was stirred at room temperature for 30 minutes, then, glycidol (8.41 g) was added thereto. Thereafter, the mixture was heated up to 60° C. and stirred for 5 hours. Thereto, methanol was added and filtration was performed. The filtrate was concentrated under reduced pressure, and 19.0 g of the resultant residue was subjected to silica gel column chromatography. Elution was performed with chloroform/methanol/water(volume ratio:6/4/1), and concentration was performed under reduced pressure to obtain 2-O-glyceryl ascorbic acid (1.21 g).

(Chemical formula 6)

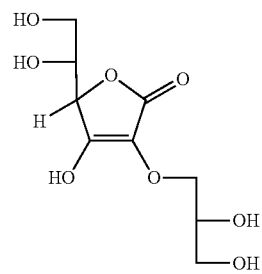

EXAMPLE 4

Synthesis of 2,3-di-O-glyceryl ascorbic acid

Under an argon atmosphere, L-ascorbic acid (100 g) and sodium hydrogen carbonate (14.4 g) were added to water and the resultant mixture was stirred at room temperature for 30 minutes, then, glycidol (42.0 g) was added thereto. Thereafter, the mixture was heated up to 50° C. and stirred for 5 hours.

Then, glycidol (57.5 g) was added and the resultant mixture was heated up to 80° C. followed by being stirred for 4 hours. Thereafter, the mixture was concentrated under reduced pressure, and 232 g of the resultant residue was subjected to alumina column chromatography. Elution was performed with chloroform/methanol/water(volume ratio:6/4/1), and concentration was performed under reduced pressure to obtain 2,3-di-O-glyceryl ascorbic acid (23.0 g).

(Chemical formula 7)

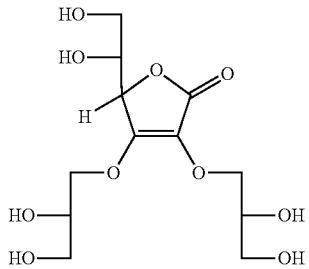

EXAMPLE 5

Synthesis of 3-O-(1',3'-dihydroxy-2'-propyl) ascorbic acid

Under an argon atmosphere, ascorbic acid (1.00 g) and sodium hydrogen carbonate (0.14 g) were added to water and the resultant mixture was stirred at room temperature for 30 minutes, then, glycidol (0.42 g) was added thereto. Thereafter, the mixture was heated up to 50° C. and stirred for 5 hours. After the reaction, water was added and the mixture was subjected to silica gel column chromatography. Elution was performed with chloroform/methanol/water(volume ratio: 65/35/5), and concentration was performed under reduced pressure to obtain 0.99 g of crude product. The resultant crude product was isolated by HPLC using a column: COSMOSIL 5C18-MS-II Waters (20 mm×250 mm) with 100% water at a flow rate of 9.9 ml/min, thereby separating and purifying a peak (8 minutes, 52 mg) of 3-O-(1',3'-dihydroxy-2'-propyl) ascorbic acid.

(Chemical formula 8)

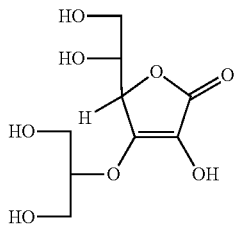

EXAMPLE 6

Synthesis of 3-O-butylglyceryl ascorbic acid

Under an argon atmosphere, L-ascorbic acid (100 g) and sodium hydrogen carbonate (14.3 g) were added to water and the mixture was stirred at room temperature for 30 minutes, then, butylglycidylether (73.8 g) was added thereto. The resultant mixture was heated up to 80° C. and stirred for 12 hours. Then, extraction with n-butanol was performed. The extracted liquid was dried over anhydrous sodium sulfate, then, concentrated under reduced pressure. Thereafter, 96.8 g of the resultant residue was subjected to silica gel column chromatography. Elution was performed with chloroform/methanol/water(volume ratio:20/3/0.3), and concentration was performed under reduced pressure to obtain 3-O-butylglyceryl ascorbic acid (74.2 g).

(Chemical formula 9)

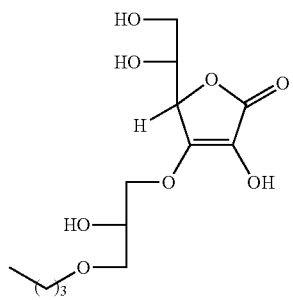

EXAMPLE 7

Synthesis of 3-O-ethylglyceryl ascorbic acid

Under an argon atmosphere, L-ascorbic acid (50.0 g) was stirred in DMF (150 mL), and ethyl glycidyl ether (34.7 g) was added, then, the mixture was heated up to 80° C. and stirred for 18 hours. Thereafter, concentration was performed under reduced pressure, and 102 g of the resultant residue was subjected to silica gel column chromatography. Elution was performed with chloroform/methanol/water(volume ratio: 10/3/0.5), and concentration was performed under reduced pressure to obtain 3-O-ethylglyceryl ascorbic acid (39.6 g).

(Chemical formula 10)

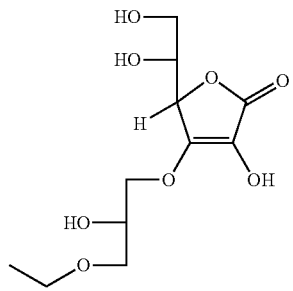

EXAMPLE 8

Synthesis of 3-O-octylglyceryl ascorbic acid

Under an argon atmosphere, sodium hydrogen carbonate (14.3 g) and 200 ml of DMSO were added to L-ascorbic acid (100 g), and further, octyl glycidyl ether (127 g) was added thereto. The mixture was heated up to 80° C. and stirred for 24 hours, then, extracted with ethyl acetate. The extracted liquid was dried over anhydrous sodium sulfate, then, concentrated under reduced pressure. Thereafter, 150 g of the resultant residue was subjected to silica gel column chromatography.

Elution was performed with chloroform/methanol/water(volume ratio:30/3/0.3), and concentration was performed under reduced pressure to obtain 3-O-octylglyceryl ascorbic acid (36 g).

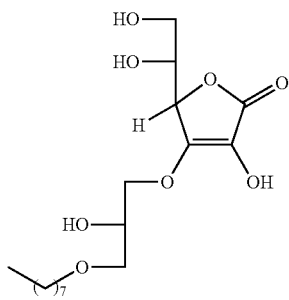

(Chemical formula 11)

EXAMPLE 9

Synthesis of 3-O-hexadecylglyceryl ascorbic acid

The same procedure as in Example 8 was carried out, except for using cetyl glycidyl ether in place of octyl glycidyl ether to obtain 3-O-hexadecylglyceryl ascorbic acid (7.31 g). (Amount of residue subjected to silica gel column chromatography was 107.2 g.)

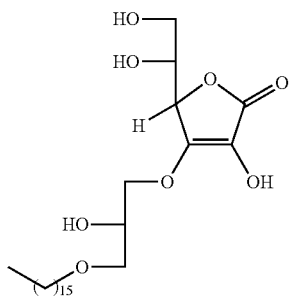

(Chemical formula 12)

EXAMPLE 10

Synthesis of 3-O-(2-hydroxyhexyl) ascorbic acid

Under an argon atmosphere, 30 ml of DMF was added to L-ascorbic acid (5.00 g), and further, 1,2-epoxyhexane (3.45 g) was added thereto. The mixture was heated up to 80° C. and stirred for 24 hours, then, extracted with ethyl acetate. The extracted liquid was dried over anhydrous sodium sulfate, then, concentrated under reduced pressure. Thereafter, 7.56 g of the resultant residue was subjected to silica gel column chromatography. Elution was performed with chloroform/methanol/water(volume ratio:20/3/0.3), and concentration was performed under reduced pressure to obtain 3-O-(2-hydroxyhexyl) ascorbic acid (1.93 g).

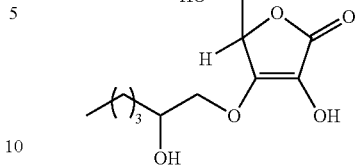

(Chemical formula 13)

EXAMPLE 11

Synthesis of 3-O-(2-hydroxycyclohexyl) ascorbic acid

Under an argon atmosphere, 4 ml of 1,1,1,3,3,3-hexafluoro isopropanol and 12 ml of acetonitrile were added to L-ascorbic acid (1.00 g), and further, 1,2-epoxycyclohexane (1.42 g) was added. The mixture was heated up to 70° C. and stirred for 36 hours, then, concentrated under reduced pressure, and 3.65 g of the resultant residue was subjected to silica gel column chromatography. Thereafter, it was eluted with chloroform/methanol/water(volume ratio:20/3/0.3) to obtain two elution fractions (first eluted fraction: 244 mg, later eluted fraction: 217 mg). Based on the measurement results of high resolution mass analysis, infrared absorption spectrum, $^{1}$H-NMR, $^{13}$C-NMR and specific optical rotation on the resultant elution fractions, it was confirmed that these are two 3-O-(2-hydroxycyclohexyl) ascorbic acids which are in mutual stereoisomerism and both of them are represented by the following structural formula.

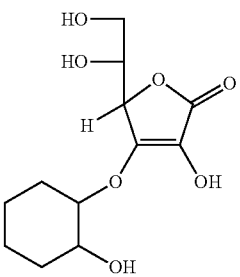

(Chemical formula 14)

Specific optical rotation $[\alpha]D^{24}$
First eluted isomer +2.90 (c=2.06 in MeOH)
Later eluted isomer +25.4 (c=2.06 in MeOH)

EXAMPLE 12

Synthesis of 3-O-(2-hydroxy-1-phenylethyl)ascorbic acid

Under an argon atmosphere, 4 ml of 1,1,1,3,3,3-hexafluoro isopropanol and 10 ml of acetonitrile were added to L-ascorbic acid (1.00 g), and further, styrene oxide (1.37 g) was added. The mixture was heated up to 70° C. and stirred for 48 hours, then, concentrated under reduced pressure, and 2.73 g of the resultant residue was subjected to silica gel column chromatography. Thereafter, it was eluted with chloroform/methanol/water(volume ratio:20/3/0.3) to obtain two elution fractions (first eluted fraction: 225 mg, later eluted fraction: 228 mg). Based on the measurement results of high resolution mass analysis, infrared absorption spectrum, $^1$H-NMR, $^{13}$C-NMR and specific optical rotation on the resultant elution fractions, it was confirmed that these are two 3-O-(2-hydroxy-1-phenylethyl) ascorbic acids which are in mutual stereoisomerism and both of them are represented by the following structural formula.

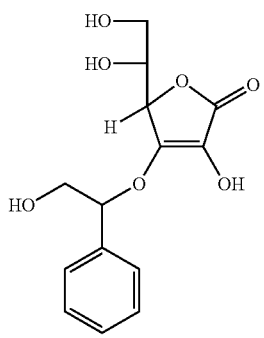

(Chemical formula 15)

Specific Optical Rotation $[\alpha]_D^{24}$
 First eluted isomer −26.8 (c=2.06 in MeOH)
 Later eluted isomer +36.7 (c=1.96 in MeOH)

EXAMPLE 13

Synthesis of 2-O-ethylglyceryl ascorbic acid

Under an argon atmosphere, L-ascorbic acid (5.00 g) and sodium hydrogen carbonate (6.02 g) were added to water and the resultant mixture was stirred at room temperature for 30 minutes, then, ethykglycidylether (8.69 g) was added thereto. Thereafter, the mixture was heated up to 80° C. and stirred for 24 hours. Thereto, methanol was added and filtration was performed. The filtrate was concentrated under reduced pressure, and 4.17 g of the resultant residue was subjected to silica gel column chromatography. Elution was performed with chloroform/methanol/water(volume ratio:65/35/5), and concentration was performed under reduced pressure to obtain 2-O-ethylglyceryl ascorbic acid (2.17 g).

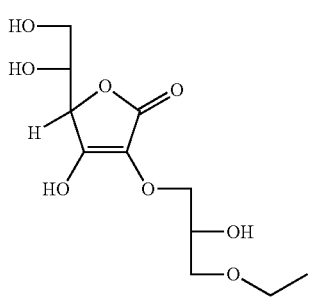

(Chemical formula 16)

EXAMPLE 14

Synthesis of 3-O-glyceryl-2-O-octyl ascorbic acid

Under an argon atmosphere, 3-O-glyceryl ascorbic acid (54.1 g) obtained in Example 1 was stirred in DMSO (200 mL), and further, sodium hydrogen carbonate (18.5 g) was added and the mixture was stirred at room temperature for 30 minutes. Thereafter, octyl bromide (63.7 g) was added and the mixture was heated up to 100° C. and stirred for 3 hours, followed by extraction with ethyl acetate. Then, the extracted liquid was dried over anhydrous sodium sulfate, and concentrated under reduced pressure, and 131 g of the resultant residue was subjected to silica gel column chromatography. Elution was performed with chloroform/methanol/water(volume ratio:10/3/0.4), and concentration was performed under reduced pressure to obtain 3-O-glyceryl-2-O-octyl ascorbic acid (48.0 g).

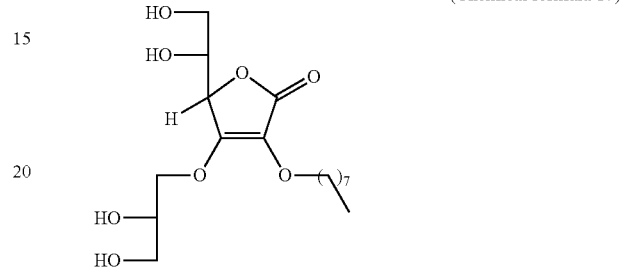

(Chemical formula 17)

EXAMPLE 15

Synthesis of 3-O-glyceryl-2-O-hexadecyl ascorbic acid

Under an argon atmosphere, 3-O-glyceryl ascorbic acid (5.10 g) obtained in Example 1 was stirred in DMSO (20 mL), and further, sodium hydrogen carbonate (1.71 g) was added and the mixture was stirred at room temperature for 30 minutes. Thereafter, hexadecyl bromide (9.42 g) was added and the mixture was heated up to 100° C. and stirred for 3 hours, followed by extraction with ethyl acetate. Then, the extracted liquid was dried over anhydrous sodium sulfate, and concentrated under reduced pressure, and 13.6 g of the resultant residue was subjected to silica gel column chromatography. Elution was performed with chloroform/methanol/water(volume ratio:20/3/0.4), and concentration was performed under reduced pressure to obtain 3-O-glyceryl-2-O-hexadecyl ascorbic acid (4.09 g).

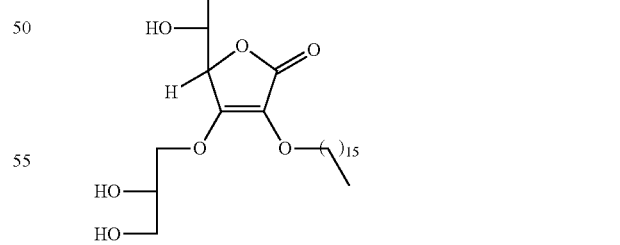

(Chemical formula 18)

EXAMPLE 16

Synthesis of 3-O-glyceryl-2-O-allyl ascorbic acid

Under an argon atmosphere, water and sodium hydrogen carbonate (1.42 g) were added to 3-O-glyceryl ascorbic acid (1.42 g) obtained in Example 1, and the mixture was stirred at room temperature for 30 minutes. To the mixture, allyl bromide (2.45 g) was added, and the resultant mixture was heated up to 60° C. and stirred for 2 hours. Thereafter, the mixture was concentrated under reduced pressure, then, dissolved in methanol. Then, the resultant solution was dried over anhydrous sodium sulfate, and concentrated under reduced pressure, and 6.70 g of the resultant residue was subjected to silica gel column chromatography. Elution was performed with chloroform/methanol/water(volume ratio:10/3/0.4), and concentration was performed under reduced pressure to obtain to obtain 3-O-glyceryl-2-O-allyl ascorbic acid (2.51 g).

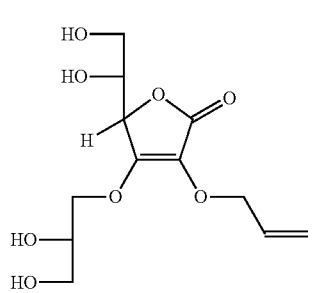

(Chemical formula 19)

EXAMPLE 17

Synthesis of 3-O-glyceryl-2-O-benzyl ascorbic acid

Under an argon atmosphere, water and sodium hydrogen carbonate (1.42 g) were added to 3-O-glyceryl ascorbic acid (1.42 g) obtained in Example 1, and the mixture was stirred at room temperature for 30 minutes. To the mixture, benzyl bromide (2.61 g) was added, and the resultant mixture was heated up to 50° C. and stirred for 2 hours. Thereafter, the mixture was concentrated under reduced pressure, then, dissolved in methanol. Then, the resultant solution was dried over anhydrous sodium sulfate, and concentrated under reduced pressure, and 6.13 g of the resultant residue was subjected to silica gel column chromatography. Elution was performed with chloroform/methanol/water(volume ratio: 10/3/0.4), and concentration was performed under reduced pressure to obtain to obtain 3-O-glyceryl-2-O-benzyl ascorbic acid (2.47 g).

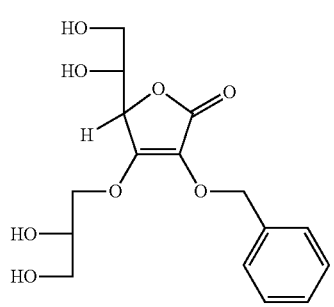

(Chemical formula 20)

EXAMPLE 18

Synthesis of 3-O-ethylglyceryl-2-O-butyl ascorbic acid

Under an argon atmosphere, 3-O-ethylglyceryl ascorbic acid (3.03 g) obtained in Example 7 was stirred in DMSO (10 mL), and further, sodium hydrogen carbonate (0.92 g) and benzyl bromide (1.79 g) were added. The mixture was heated up to 100° C. and stirred for 5 hours, followed by extraction with ethyl acetate. Then, the extracted liquid was dried over anhydrous sodium sulfate, and concentrated under reduced pressure, and 2.16 g of the resultant residue was subjected to silica gel column chromatography. Elution was performed with chloroform/methanol/water(volume ratio:20/3/0.3), and concentration was performed under reduced pressure to obtain 3-O-ethylglyceryl-2-O-butyl ascorbic acid (0.89 g).

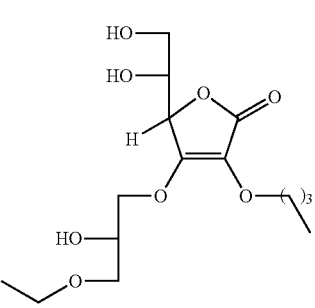

(Chemical formula 21)

EXAMPLE 19

Synthesis of 3-O-butylglyceryl-2-O-butyl ascorbic acid

Under an argon atmosphere, 3-O-butylglyceryl ascorbic acid (3.06 g) obtained in Example 6 was stirred in DMSO (10 mL), and further, sodium hydrogen carbonate (0.84 g) was added. To the mixture, benzyl bromide (2.06 g) was added and the mixture was heated up to 100° C. and stirred for 3 hours, followed by extraction with ethyl acetate. Then, the extracted liquid was dried over anhydrous sodium sulfate, and concentrated under reduced pressure, and 3.52 g of the resultant residue was subjected to silica gel column chromatography. Elution was performed with chloroform/methanol/water (volume ratio:50/3/0.3), and concentration was performed under reduced pressure to obtain 3-O-butylglyceryl-2-O-butyl ascorbic acid (0.95 g).

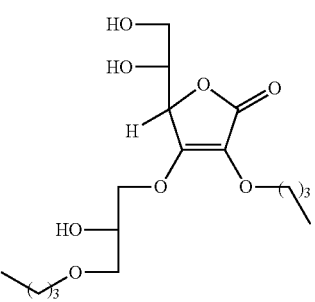

(Chemical formula 22)

EXAMPLE 20

Synthesis of 3-O-octylglyceryl-2-O-hexadecyl ascorbic acid

Under an argon atmosphere, 3-O-octylglyceryl ascorbic acid (5.17 g) obtained in Example 8 was stirred in DMSO (10 mL), and further, sodium hydrogen carbonate (1.20 g) and hexadecyl bromide (5.22 g) were added. The mixture was heated up to 100° C. and stirred for 3 hours, followed by extraction with ethyl acetate. Then, the extracted liquid was dried over anhydrous sodium sulfate, and concentrated under reduced pressure, and 9.06 g of the resultant residue was subjected to silica gel column chromatography. Elution was performed with chloroform/methanol/water(volume ratio: 50/3 10.3), and concentration was performed under reduced pressure to obtain 3-O-octylglyceryl-2-O-hexadecyl ascorbic acid (3.41 g).

(Chemical formula 23)

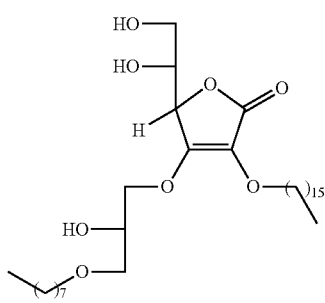

EXAMPLE 21

Synthesis of 3-O-butylglyceryl-2-O-allyl ascorbic acid

Under an argon atmosphere, water and sodium hydrogen carbonate (0.98 g) were added to 3-O-butylglyceryl ascorbic acid (3.56 g) obtained in Example 6, and the mixture was stirred at room temperature for 30 minutes. To the mixture, allyl bromide (1.68 g) was added, and the resultant mixture was heated up to 60° C. and stirred for 5 hours, followed by extraction with ethyl acetate. Then, the extracted liquid was dried over anhydrous sodium sulfate, and concentrated under reduced pressure, and 3.53 g of the resultant residue was subjected to silica gel column chromatography. Elution was performed with chloroform/methanol/water(volume ratio: 30/3/0.3), and concentration was performed under reduced pressure to obtain to obtain 3-O-butylglyceryl-2-O-allyl ascorbic acid (3.00 g).

(Chemical formula 24)

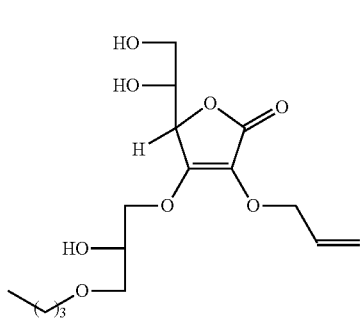

EXAMPLE 22

Synthesis of 3-O-glyceryl-2-O-butylglyceryl ascorbic acid

Under an argon atmosphere, 3-O-glyceryl ascorbic acid (5.27 g) obtained in Example 1 was stirred in DMSO (10 mL), and further, sodium hydrogen carbonate (0.53 g) was added. Thereafter, butyl glycidyl ether (4.10 g) was added and the mixture was heated up to 80° C. and stirred for 18 hours, followed by extraction with ethyl acetate. Then, the extracted liquid was dried over anhydrous sodium sulfate, and concentrated under reduced pressure, and 3.47 g of the resultant residue was subjected to silica gel column chromatography. Elution was performed with chloroform/methanol/water(volume ratio:20/3/0.4), and concentration was performed under reduced pressure to obtain 3-O-glyceryl-2-O-butylglyceryl ascorbic acid (0.62 g).

(Chemical formula 25)

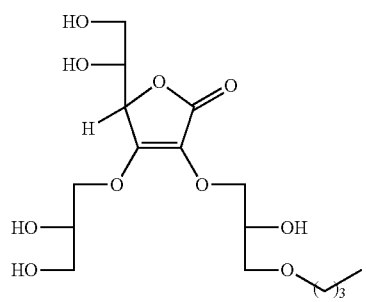

EXAMPLE 23

Synthesis of 3-O-butylglyceryl-2-O-glyceryl ascorbic acid

Under an argon atmosphere, 3-O-butylglyceryl ascorbic acid (4.98 g) obtained in Example 6 was stirred in DMSO(10 mL), and further, sodium hydrogen carbonate (0.33 g) was added. Thereafter, glycidol (1.46 g) was added and the mixture was heated up to 80° C. and stirred for 18 hours, followed by extraction with n-butnol. The extracted liquid was dried over anhydrous sodium sulfate, and concentrated under reduced pressure, and 6.23 g of the resultant residue was subjected to silica gel column chromatography. Elution was performed with chloroform/methanol/water(volume ratio: 20/3/0.4), and concentration was performed under reduced pressure to obtain 3-O-butylglyceryl-2-O-glyceryl ascorbic acid (1.23 g).

(Chemical formula 26)

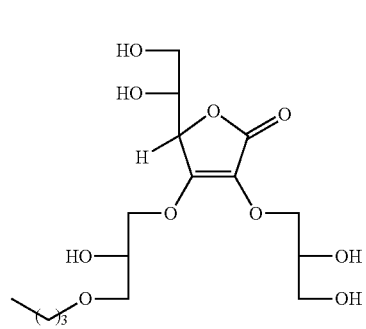

EXAMPLE 24

Synthesis of 3-O-butylglyceryl-2-O-hexadecylglyceryl ascorbic acid

Under an argon atmosphere, 3-O-butylglyceryl ascorbic acid (5.31 g) obtained in Example 6 was stirred in DMSO(10 mL), and further, sodium hydrogen carbonate (0.44 g) was added. Thereafter, hexadecylglycidyl ether (4.82 g) was added and the mixture was heated up to 80° C. and stirred for 18 hours, followed by extraction with ethylacetate. The extracted liquid was dried over anhydrous sodium sulfate, and concentrated under reduced pressure, and 6.81 g of the resultant residue was subjected to silica gel column chromatography. Elution was performed with chloroform/methanol/water (volume ratio:50/3/0.3), and concentration was performed under reduced pressure to obtain 3-O-butylglyceryl-2-O-hexadecylglyceryl ascorbic acid (1.23 g).

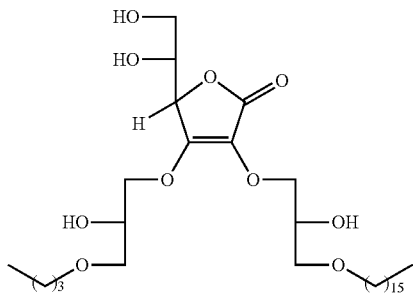

(Chemical formula 27)

EXAMPLE 25

Synthesis of 3-O-dodecylglyceryl ascorbic acid

Under an argon atmosphere, L-ascorbic acid (100 g) was stirred in DMF (200 mL), and dodecyl glycidyl ether (166 g) was added. Then, the mixture was heated up to 80° C. and stirred for 24 hours, followed by extraction with ethyl acetate. The extracted liquid was dried over anhydrous sodium sulfate, then, concentrated under reduced pressure. Thereafter, 182 g of the resultant residue was subjected to silica gel column chromatography. Elution was performed with chloroform/methanol/water(volume ratio:30/3/0.3), and concentration was performed under reduced pressure to obtain 3-O-dodecylglyceryl ascorbic acid (45.6 g).

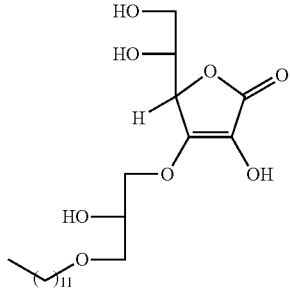

(Chemical formula 28)

EXAMPLE 26

Synthesis of 3-O-dodecylglyceryl-2-O-octylglyceryl ascorbic acid

Under an argon atmosphere, 3-O-dodecylglyceryl ascorbic acid (1.00 g) obtained in Example 25 was stirred in DMSO(2 mL), and further, sodium hydrogen carbonate (0.06 g) was added. Thereafter, glycidyl octyl ether (0.53 g) was added and the mixture was heated up to 100° C. and stirred for 22 hours, followed by extraction with ethyl acetate. The extracted liquid was dried over anhydrous sodium sulfate, then, concentrated under reduced pressure. Thereafter, 1.33 g of the resultant residue was subjected to silica gel column chromatography. Elution was performed with chloroform/methanol/water(volume ratio:50/3/0.3), and concentration was performed under reduced pressure to obtain 3-O-dodecylglyceryl-2-O-octylglyceryl ascorbic acid (0.17 g).

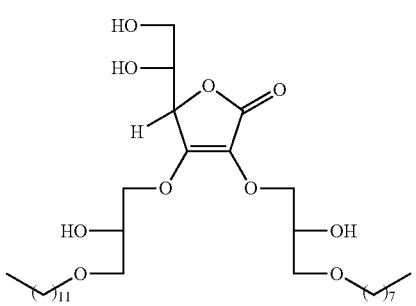

(Chemical formula 29)

EXAMPLE 27

Synthesis of 3-O-(2-O-hydroxydecyl) ascorbic acid

Under an argon atmosphere, L-ascorbic acid (14.2 g) was stirred in DMF (20 mL), and 1,2-epoxydecane (15.1 g) was added. Then, the mixture was heated up to 80° C. and stirred for 24 hours, followed by extraction with ethyl acetate. The extracted liquid was dried over anhydrous sodium sulfate, then, concentrated under reduced pressure. Thereafter, 26.6 g of the resultant residue was subjected to silica gel column chromatography. Elution was performed with chloroform/methanol/water(volume ratio:20/3/0.3), and concentration was performed under reduced pressure to obtain 3-O-(2-O-hydroxydecyl) ascorbic acid (7.01 g).

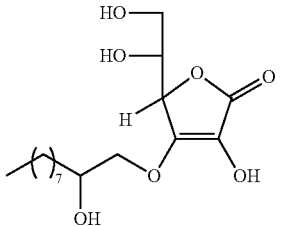

(Chemical formula 30)

EXAMPLE 28

Synthesis of 3-O-(2-hydroxydecyl)-2-O-butylglyceryl ascorbic acid

Under an argon atmosphere, 3-O-(2-β-hydroxydecyl) ascorbic acid (1.03 g) obtained in Example 27 was stirred in DMSO(10 mL), and further, sodium hydrogen carbonate (0.08 g) was added. Thereafter, butyl glycidyl ether (0.97 g) was added and the mixture was heated up to 100° C. and stirred for 8 hours, followed by extraction with ethyl acetate. The extracted liquid was dried over anhydrous sodium sulfate, then, concentrated under reduced pressure. Thereafter, 1.12 g of the resultant residue was subjected to silica gel column chromatography. Elution was performed with chloroform/methanol/water(volume ratio:30/3/0.3), and concentration was performed under reduced pressure to obtain 3-O-(2-hydroxydecyl)-2-O-butylglyceryl ascorbic acid (0.27 g).

(Chemical formula 31)

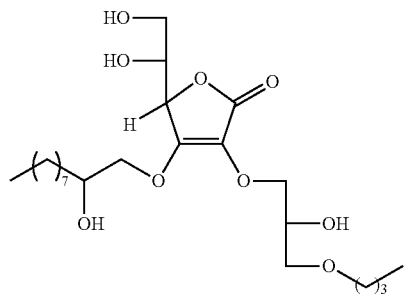

EXAMPLE 29

Synthesis of 3-O-glyceryl-2-O-(2-hydroxydecyl) ascorbic acid

Under an argon atmosphere, 3-O-glyceryl ascorbic acid (5.00 g) obtained in Example 1 was stirred in DMSO(8 mL), and further, sodium hydrogen carbonate (0.50 g) was added. Thereafter, 1,2-epoxydecane (3.75 g) was added and the mixture was heated up to 100° C. and stirred for 10 hours, followed by extraction with ethyl acetate. The extracted liquid was dried over anhydrous sodium sulfate, then, concentrated under reduced pressure. Thereafter, 3.40 g of the resultant residue was subjected to silica gel column chromatography. Elution was performed with chloroform/methanol/water(volume ratio:20/3/0.3), and concentration was performed under reduced pressure to obtain 3-O-glyceryl-2-O-(2-O-hydroxydecyl) ascorbic acid (0.41 g).

(Chemical formula 32)

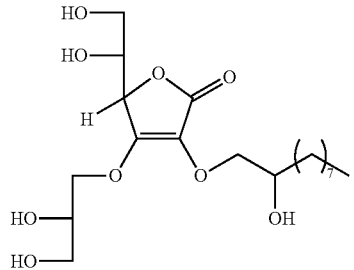

The measurement results of high resolution mass analysis of the products obtained in Examples 1 to 29 are shown in Table 1.

TABLE 1

| Example No. | Method* | Theoretical value | Measured value |
|---|---|---|---|
| 1 | F+ | 251.0767 | 251.0773 |
| 3 | C+ | 251.0767 | 251.0774 |
| 4 | E+ | 324.1056 | 324.1061 |
| 5 | E+ | 250.0688 | 250.0690 |
| 6 | F+ | 307.1393 | 307.1395 |
| 7 | F+ | 279.1080 | 279.1079 |
| 8 | F+ | 363.2018 | 363.2025 |
| 9 | F+ | 475.3270 | 475.3264 |
| 10 | E+ | 276.1209 | 276.1202 |
| 11: first eluted fraction | F+ | 275.1131 | 275.1148 |
| 11: later eluted fraction | F+ | 275.1131 | 275.1154 |
| 12: first eluted fraction | F+ | 297.0974 | 297.0985 |
| 12: later eluted fraction | F+ | 297.0974 | 297.1000 |
| 13 | E+ | 278.1001 | 278.0994 |
| 14 | E+ | 362.1940 | 362.1931 |
| 15 | E+ | 474.3192 | 474.3190 |
| 16 | E+ | 290.1001 | 290.0997 |
| 17 | E+ | 340.1158 | 340.1151 |
| 18 | E+ | 334.1627 | 334.1626 |
| 19 | E+ | 362.1940 | 362.1947 |
| 20 | E+ | 586.4444 | 586.4446 |
| 21 | E+ | 346.1627 | 346.1622 |
| 22 | E+ | 380.1682 | 380.1686 |
| 23 | E+ | 380.1682 | 380.1688 |
| 26 | E+ | 604.4186 | 604.4179 |
| 28 | E+ | 462.2828 | 462.2824 |
| 29 | E+ | 406.2202 | 406.2207 |

*Method: E+ represents EI-MS positive, F+ represents FAB-MS positive and C+ represents CI-MS positive, in the table 1. These are applicable also in the following tables showing the measurement results of high resolution mass analysis. Theoretical value and Measured value of C+ show "actual molecular weight + 1(i.e. +molecular weight of +H)", the values of F+ in examples other than Example 93 show "actual molecular weight + 1(i.e.+molecular weight of +H)", and the values of F+ in Example 93 show "actual molecular weight + 23(i.e. +molecular weight of + Na)".

The results of measurement of infrared absorption spectrum of the products obtained in Examples 1 to 29 are shown in Table 2.

TABLE 2

| Example No. | Condition* | Measured value(Wavenumber $cm^{-1}$) |
|---|---|---|
| 1 | TlBr | 3275, 1759, 1693 |
| 3 | ATR | 3221, 1732, 1645 |
| 4 | TlBr | 3368, 1749, 1672 |
| 5 | TlBr | 3329, 1755, 1688 |
| 6 | TlBr | 3308, 2961, 2936, 2874, 1747, 1699 |
| 7 | TlBr | 3227, 1761, 1695 |
| 8 | $As_2Se_3$ | 3406, 2928, 2856, 1747, 1697 |
| 9 | KBr | 3423, 2918, 2851, 1749, 1668 |
| 10 | KBr | 3464, 2934, 1761, 1674 |
| 11: first eluted fraction | KBr | 3350, 2939, 2864, 1755, 1690 |
| 11: later eluted fraction | KBr | 3136, 2943, 2864, 1751, 1686 |
| 12: first eluted fraction | KBr | 3339, 1751 |
| 12: later eluted fraction | TlBr | 3396, 1754 |
| 13 | ATR | 3225, 1740, 1643 |
| 14 | KBr | 3368, 2855, 1751, 1676 |
| 15 | KBr | 3422, 2918, 2851, 1749, 1676 |
| 16 | TlBr | 3310, 1749, 1672 |
| 17 | TlBr | 3369, 1751, 1674 |
| 18 | TlBr | 3401, 2957, 2878, 1763, 1674 |
| 19 | TlBr | 3368, 2961, 2936, 2874, 1751, 1676 |
| 20 | TlBr | 3306, 2920, 2853, 1655 |
| 21 | ATR | 3396, 2936, 2874, 1757, 1676 |

TABLE 2-continued

| Example No. | Condition* | Measured value(Wavenumber cm$^{-1}$) |
|---|---|---|
| 22 | TlBr | 3369, 2936, 2874, 1753, 1676 |
| 23 | TlBr | 3391, 2934, 2874, 1749, 1674 |
| 24 | TlBr | 3402, 2926, 2855, 1755, 1676 |
| 26 | TlBr | 3395, 2926, 2855, 1751, 1676 |
| 28 | TlBr | 3365, 2930, 2858, 1749, 1672 |
| 29 | TlBr | 3352, 2928, 2856, 1751, 1674 |

*Condition: TlBr and $As_2Se_3$ represent a liquid membrane technique using TlBr and $As_2Se_3$ respectively, and KBr and ATR represent a KBr method and an ATR method respectively. These are applicable also in the following tables showing the results of measurement of infrared absorption spectrum.

The results of measurement of $^1$H-NMR of the products obtained in Examples 1 to 29 are shown in Tables 3-5.

TABLE 3

| Example No. | Condition | Chemical shift δ (ppm) |
|---|---|---|
| 1 | 600 MHz, CD$_3$OD | 3.59 (2H, m), 3.66 (2H, m), 3.89 (1H, m), 3.92 (1H, m), 4.45/4.49 (1H, dd), 4.59/4.62 (1H, dd), 4.82 (1H, d) |
| 2 | 600 MHz, CD$_3$OD | 3.60 (2H, m), 3.66 (2H, m), 3.82 (1H, m), 3.84 (1H, m), 4.43/4.50/4.57 (dd/m/dd, 2H), 4.70 (1H, d) |
| 3 | 400 MHz, CD$_3$OD | 3.61 (2H, m), 3.67 (2H, m), 3.90 (1H, m), 3.92 (1H, dt-like), 3.92 (1H, m), 4.07/4.09 (1H, dd), 4.86 (1H, d) |
| 4 | 400 MHz, CD$_3$OD | 3.58 (2H, m), 3.61 (2H, m), 3.65 (2H, m), 3.88 (1H, m), 3.91 (1H, m), 3.93 (1H, m), 3.99 (1H, m), 4.16 (1H, m), 4.53 (1H, m), 4.65 (1H, dd), 4.88 (1H, m) |
| 5 | 500 MHz, CD$_3$OD | 3.67 (m), 3.75 (dd), 3.78 (dd), 3.81 (dd), 3.84 (dd), 4.84 (d), 4.99 (m) |
| 6 | 500 MHz, CD$_3$OD | 0.93 (m), 1.38 (m), 1.56 (m), 3.49 (m), 3.50 (m), 3.66 (m), 3.88 (m), 4.03 (m), 4.44 (dd), 4.46 (dd), 4.59 (dd), 4.62 (dd), 4.81 (d) |
| 7 | 500 MHz, CD$_3$OD | 1.19 (m), 3.51 (m), 3.54 (m), 3.65 (m), 3.88 (m), 4.03 (m), 4.44 (dd), 4.46 (dd), 4.58 (dd), 4.61 (dd), 4.81 (d) |
| 8 | 500 MHz, CD$_3$OD | 0.89 (t), 1.29 (brs), 1.57 (m), 3.46 (m), 3.51 (m), 3.66 (m), 3.88 (m), 4.03 (m), 4.44 (dd), 4.46 (dd), 4.59 (dd), 4.62 (dd), 4.81 (d) |
| 9 | 600 MHz, CD$_3$OD | 0.89 (t), 1.28 (brs), 1.57 (m), 3.47 (m), 3.51 (m), 3.65 (m), 3.88 (m), 4.03 (m), 4.44 (dd), 4.46 (dd), 4.59 (dd), 4.62 (dd), 4.81 (d) |
| 10 | 600 MHz, CD$_3$OD | 0.93 (m), 1.36 (m), 1.48 (m), 3.65 (m), 3.88 (m), 4.27 (dd), 4.31 (dd), 4.51 (dd), 4.53 (dd), 4.81 (d) |
| 11: first eluted | 500 MHz, CD$_3$OD | 1.29 (m), 1.33 (m), 1.37 (m), 1.70 (m), 2.00 (m), 2.23 (m), 3.56 (m), 3.66 (m), 3.93 (dt), 4.76 (d), 4.85 (ddd) |
| 11: later eluted | 600 MHz, CD$_3$OD | 1.28 (m), 1.31 (m), 1.39 (m), 1.73 (m), 2.00 (m), 2.23 (m), 3.57 (m), 3.65 (m), 3.84 (dt), 4.83 (d), 4.60 (ddd) |

TABLE 4

| Example No. | Condition | Chemical shift δ (ppm) |
|---|---|---|
| 12: first eluted | 600 MHz, CD$_3$OD | 3.68 (m), 3.78 (dd), 3.85 (dd), 4.02 (dt), 4.77 (d), 6.04 (dd), 7.32 (m), 7.36 (m), 7.41 (m) |
| 12: later eluted | 600 MHz, CD$_3$OD | 3.65 (d), 3.80 (dd), 3.84 (dd), 3.93 (dt), 4.91 (d), 5.95 (dd), 7.29 (m), 7.35 (m), 7.42 (m) |
| 13 | 400 MHz, CD$_3$OD | 1.18 (3H, t), 3.50 (4H, m), 3.66 (2H, brd), 3.92 (2H, m), 3.97 (1H, m), 4.07/4.08 (1H, dd), 4.83 (1H, d) |
| 14 | 600 MHz, CD$_3$OD | 0.90 (3H, t), 1.32 (8H, m), 1.42 (2H, m), 1.70 (2H, m), 3.60 (2H, brd), 3.65 (2H, m), 3.89 (1H, m), 3.91 (1H, m), 4.02 (1H, m), 4.47/4.48 (1H, dd), 4.57/4.59 (1H, dd), 4.86 (1H, d) |
| 15 | 600 MHz, CD$_3$OD | 0.89 (3H, t), 1.28 (24H, brs), 1.41 (2H, m), 1.70 (2H, m), 3.60 (2H, brd), 3.66 (2H, m), 3.90 (1H, m), 3.91 (1H, m), 4.02 (1H, m), 4.47/4.48 (1H, dd), 4.57/4.59 (1H, dd), 4.86 (1H, brs) |
| 16 | 500 MHz, CD$_3$OD | 3.59 (2H, brd), 3.65 (2H, m), 3.90 (2H, m), 4.47/4.48 (1H, dd), 4.58/4.59 (1H, dd), 4.87 (1H, d), 5.25 (1H, m), 5.35 (1H, m), 6.04 (1H, m) |
| 17 | 500 MHz, CD$_3$OD | 3.49 (2H, m), 3.65 (2H, m), 3.81 (1H, m), 3.88 (1H, m), 4.47/4.28 (1H, dd), 4.36/4.37 (1H, dd), 4.85 (1H, brs), 5.05 (2H, m), 7.35 (3H, m), 7.43 (2H, m) |
| 18 | 600 MHz, CD$_3$OD | 0.96 (3H, m), 1.18 (3H, m), 1.45 (2H, m), 1.68 (2H, m), 3.53 (4H, m), 3.65 (2H, m), 3.90 (1H, m), 4.02 (4H, m), 4.46 (1H, dd), 4.58/4.59 (1H, dd), 4.86 (1H, d) |

TABLE 4-continued

| Example No. | Condition | Chemical shift δ (ppm) |
|---|---|---|
| 19 | 500 MHz, CD$_3$OD | 0.93 (3H, t), 0.96 (3H, t), 1.39 (2H, m), 1.45 (2H, m), 1.56 (2H, m), 1.68 (2H, m), 3.49 (4H, m), 3.65 (2H, m), 3.89 (1H, dt-like), 4.02 (3H, m), 4.455/4.462 (1H, dd), 4.584/4.591 (1H, dd), 4.86 (1H, brs) |
| 20 | 600 MHz, DMSO-d$_6$, 40° C. | 0.90 (6H, m), 1.24 (34H, brs), 1.34 (2H, m), 1.48 (2H, m), 1.60 (2H, m), 3.38 (4H, m), 3.46 (2H, m), 3.72 (1H, m), 3.87 (1H, m), 3.94 (2H, m), 4.25/4.31 (1H, dd), 4.42/4.45 (1H, dd), 4.82 (1H, d) |

TABLE 5

| Example No. | Condition | Chemical shift δ (ppm) |
|---|---|---|
| 21 | 500 MHz, CD$_3$OD | 0.93 (3H, t), 1.39 (2H, m), 1.55 (2H, m), 3.48 (4H, m), 3.65 (2H, m), 3.89 (1H, m), 4.01 (1H, m), 4.457/4.464 (1H, dd), 4.54 (2H, m), 4.586/594 (1H, dd), 4.87 (1H, d), 5.25 (1H, m), 5.35 (1H, m), 6.04 (1H, m) |
| 22 | 500 MHz, CD$_3$OD | 0.92 (3H, t), 1.38 (2H, m), 1.55 (2H, m), 3.47 (4H, m), 3.60 (2H, m), 3.65 (2H, m), 3.91 (3H, m), 3.99 (1H, m), 4.17 (1H, m), 4.53 (1H, m), 4.65 (1H, m), 4.87 (brs) |
| 23 | 600 MHz, CD$_3$OD | 0.92 (3H, m), 1.38 (2H, m), 1.56 (2H, m), 3.49 (4H, m), 3.58 (2H, m), 3.67 (2H, m), 3.90 (2H, m), 4.01 (1H, m), 4.01 (1H, m), 4.17 (1H, m), 4.52 (1H, m), 4.64 (1H, m), 4.88 (1H, m) |
| 24 | 600 MHz, d$_6$-DMSO, 40° C. | 0.85 (3H, t), 0.87 (3H, t), 1.24 (26H, brs), 1.31 (2H, m), 1.47 (4H, m), 3.38 (6H, m), 3.40 (2H, m), 3.56 (2H, m), 3.72 (1H, m), 3.86 (2H, m), 3.86 (1H, m), 3.98 (2H, m), 4.34 (1H, m), 4.46 (1H, m), 4.82 (1H, brd) |
| 26 | 600 MHz, d$_6$-DMSO, 40° C. | 0.85 (6H, t), 1.24 (28H, brs), 1.48 (4H, m), 3.37 (8H, m), 3.55 (2H, m), 3.72 (1H, m), 3.86 (3H, m), 3.96 (1H, m), 4.34 (1H, m), 4.46 (1H, m), 4.81 (1H, m) |
| 28 | 500 MHz, CD$_3$OD | 0.90 (3H, t), 0.92 (3H, t), 1.32 (12H, m), 1.39 (2H, m), 1.48 (2H, m), 1.55 (2H, m), 3.47 (4H, m), 3.66 (2H, m), 3.86 (1H, m), 3.91 (1H, m), 4.00 (2H, m), 4.16 (1H, m), 4.38 (1H, m), 4.55 (1H, m), 4.87 (1H, brs) |
| 29 | 700 MHz, CD$_3$OD | 0.89 (3H, t), 1.31 (12H, brs), 1.47 (2H, m), 3.60 (2H, m), 3.66 (2H, m), 3.82 (1H, m), 3.86 (2H, m), 3.91 (1H, m), 4.00 (1H, m), 4.53 (1H, m), 4.65 (1H, m), 4.87 (1H, d) |

The results of measurement of $^{13}$C-NMR of the products obtained in Examples 1 to 29 are shown in Tables 6-8.

TABLE 6

| Example No. | Condition | Chemical shift δ (ppm) |
|---|---|---|
| 1 | 150 MHz, CD$_3$OD | 63.4, 63.7, 70.56, 70.61, 71.79, 71.89, 73.4, 73.6, 76.9, 121.17, 121.24, 151.84, 151.88, 173.04, 173.07 |
| 2 | 150 MHz, CD$_3$OD | 63.7, 63.8, 71.29, 71.32, 72.1, 72.2, 72.3, 73.4, 76.67, 76.70, 129.0, 129.1, 147.7, 147.9, 177.7 |
| 3 | 100 MHz, CD$_3$OD | 63.3, 63.7, 70.4, 72.0, 74.6, 76.8, 122.2, 161.6, 172.9 |
| 4 | 100 MHz, CD$_3$OD | 63.22, 63.60, 63.63, 63.95, 63.98, 64.44, 70.57, 70.60, 71.68, 71.94, 71.98, 73.87, 74.27, 74.33, 5.06, 76.83, 123.02, 159.48, 172.29 |
| 5 | 125 MHz, CD$_3$OD | 62.3, 62.4, 63.3, 70.6, 77.1, 83.3, 120.9, 151.2, 172.9 |
| 6 | 125 MHz, CD$_3$OD | 14.2, 20.3, 32.8, 63.36, 63.39, 70.2, 70.4, 70.56, 70.61, 72.4, 72.5, 72.6, 73.8, 73.9, 76.8, 121.1, 121.2, 151.7, 151.8, 172.9, 173.0 |
| 7 | 125 MHz, CD$_3$OD | 15.4, 63.36, 63.40, 67.9, 70.2, 70.4, 70.5, 70.6, 72.31, 72.35, 73.8, 73.9, 76.8, 121.1, 121.2, 151.7, 151.8, 172.9, 173.0 |
| 8 | 125 MHz, CD$_3$OD | 14.1, 27.2, 23.7, 30.4, 30.6, 30.7, 33.0, 63.36, 63.39, 70.2, 70.4, 70.56, 70.60, 72.5, 72.6, 72.7, 73.8, 73.9, 76.8, 121.1, 121.2, 151.7, 151.8, 172.89, 172.93 |
| 9 | 150 MHz, CD$_3$OD | 14.4, 23.7, 27.2, 30.7, 33.0, 30.5, 30.75, 30.78, 63.36, 63.40, 70.2, 70.4, 70.56, 70.62, 72.5, 72.6, 72.7, 73.8, 73.9, 76.8, 121.1, 121.2, 151.7, 151.8, 172.90, 172.93 |
| 10 | 150 MHz, CD$_3$OD | 14.3, 23.68, 23.70, 26.68, 28.75, 33.70, 33.74, 63.36, 63.40, 70.6, 70.7, 70.9, 71.1, 76.3, 76.4, 76.8, 120.9, 121.0, 151.8, 151.9, 172.96, 173.02 |

TABLE 6-continued

| Example No. | Condition | Chemical shift δ (ppm) |
|---|---|---|
| 11: first eluted | 125 MHz, CD₃OD | 24.82, 24.84, 32.0, 34.2, 63.2, 70.6, 74.2, 77.2, 85.2, 120.3, 152.5, 173.1 |
| 11: later eluted | 150 MHz, CD₃OD | 24.76, 24.84, 32.0, 34.1, 63.6, 70.7, 73.7, 76.8, 85.5, 120.1, 152.1, 173.3 |

TABLE 7

| Example No. | Condition | Chemical shift δ (ppm) |
|---|---|---|
| 12: first eluted | 150 MHz, CD₃OD | 63.3, 67.0, 70.5, 77.2, 84.5, 121.4, 127.7, 128.9, 129.5, 139.2, 150.6, 172.8 |
| 12: later eluted | 150 MHz, CD₃OD | 63.6, 67.0, 70.6, 76.7, 84.7, 121.0, 127.7, 129.3, 129.4, 139.2, 151.4, 172.9 |
| 13 | 100 MHz, CD₃OD | 15.37, 63.36, 67.87, 70.58, 70.63, 72.47, 72.49, 74.98, 75.05, 76.97, 122.09, 122.13, 162.53, 162.56, 173.03, 173.05 |
| 14 | 150 MHz, CD₃OD | 14.4, 23.7, 26.9, 30.37, 30.44, 30.8, 33.0, 63.2, 63.56, 63.59, 70.5, 70.6, 71.5, 71.6, 74.01, 74.04, 74.1, 76.7, 123.27, 123.30, 159.2, 159.3, 172.2 |
| 15 | 150 MHz, CD₃OD | 14.4, 23.7, 27.0, 30.76, 30.47, 30.50, 30.71, 30.76, 30.80, 33.1, 63.2, 63.56, 63.59, 70.5, 70.6, 71.5, 71.6, 74.0, 74.1, 76.7, 123.27, 123.31, 159.23, 159.25, 172.2 |
| 16 | 125 MHz, CD₃OD | 63.19, 63.51, 63.55, 70.49, 70.52, 71.50, 71.57, 74.14, 74.16, 74.18, 74.22, 76.79, 119.36, 122.51, 122.55, 134.50, 159.67, 159.71, 172.10 |
| 17 | 175 MHz, CD₃OD | 63.21, 63.51, 63.54, 70.54, 70.57, 71.42, 71.49, 74.12, 74.20, 75.25, 75.28, 76.80, 76.82, 122.27, 122.31, 129.60, 129.95, 130.11, 137.61, 159.90, 159.94, 172.17 |
| 18 | 150 MHz, CD₃OD | 14.14, 15.33, 15.41, 20.09, 32.90, 63.22, 63.24, 67.95, 68.07, 70.01, 70.09, 70.51, 70.56, 72.31, 73.68, 74.51, 74.58, 76.67, 76.70, 123.25, 123.28, 159.22, 159.26, 172.21 |
| 19 | 125 MHz, CD₃OD | 14.17, 14.25, 20.11, 20.34, 32.85, 32.91, 63.20, 70.00, 70.11, 72.43, 72.51, 72.56, 73.68, 74.56, 74.60, 76.65, 74.60, 123.22, 123.25, 159.24, 159.29, 172.21 |
| 20 | 150 MHz, d₆-DMSO, 40° C. | 13.95, 22.13, 25.40, 25.42, 25.63, 25.71, 28.74, 28.78, 28.87, 28.97, 29.09, 29.20, 29.28, 29.30, 31.34, 61.72, 68.04, 68.09, 68.81, 70.88, 71.48, 71.52, 72.14, 73.24, 73.43, 74.55, 121.29, 157.71, 157.85, 169.42 |

TABLE 8

| Example No. | Condition | Chemical shift δ (ppm) |
|---|---|---|
| 21 | 125 MHz, CD₃OD | 14.24, 20.33, 32.83, 63.19, 70.00, 70.10, 70.50, 70.54, 72.42, 72.45, 72.50, 74.14, 74.63, 74.65, 76.77, 76.79, 119.25, 122.50, 122.54, 134.52, 159.67, 159.72, 172.08 |
| 22 | 125 MHz, CD₃OD | 14.26, 20.32, 32.86, 63.18, 63.56, 63.59, 63.64, 70.38, 70.42, 70.54, 70.57, 71.62, 71.65, 71.68, 71.72, 72.38, 72.89, 74.23, 74.31, 74.40, 74.49, 75.27, 75.30, 75.32, 75.39, 76.77, 76.79, 122.93, 122.98, 123.01, 123.08, 159.33, 159.39, 172.12 |
| 23 | 150 MHz, CD₃OD | 14.21, 14.24, 20.26, 20.30, 32.73, 32.80, 63.19, 63.22, 63.96, 63.99, 70.05, 70.14, 70.21, 70.23, 70.55, 70.58, 71.91, 71.96, 72.45, 74.46, 74.55, 74.62, 74.75, 75.01, 75.04, 76.81, 76.88, 122.94, 122.99, 159.46, 159.50, 159.69, 172.28 |
| 24 | 150 MHz, d₆-DMSO, 40° C. | 13.81, 13.97, 18.87, 22.15, 22.69, 25.69, 28.76, 28.98, 29.09, 29.28, 29.09, 31.36, 61.68, 61.72, 68.13, 68.18, 68.21, 68.27, 68.31, 68.34, 68.38, 68.85, 68.87, 70.34, 70.53, 70.63, 70.80, 71.37, 71.43, 71.47, 71.80, 71.87, 73.20, 73.38, 73.44, 73.91, 73.97, 74.64, 74.78, 121.28, 121.34, 121.41, 157.64, 157.68, 157.71, 157.89, 169.24, 169.31, 169.36, 169.41 |
| 26 | 150 MHz, d₆-DMSO, 40° C. | 13.95, 22.14, 25.70, 28.77, 28.89, 28.96, 29.01, 29.08, 29.12, 29.29, 31.33, 31.36, 61.72, 68.10, 68.18, 68.30, 68.33, 68.84, 68.84, 68.86, 70.80, 70.87, 71.36, 71.43, 71.86, 71.88, 73.21, 73.24, 73.36, 73.39, 73.89, 73.93, 73.96, 74.62, 121.28, 121.33, 121.41, 157.59, 157.61, 157.66, 157.69, 169.39 |
| 28 | 125 MHz, CD₃OD | 14.29, 14.45, 20.33, 26.55, 26.58, 30.44, 30.60, 30.69, 34.01, 63.09, 63.19, 63.38, 70.30, 70.38, 70.48, 70.55, 70.61, 70.64, 70.69, 70.74, 70.88, 71.01, 71.04, 72.41, 75.20, 75.24, 75.32, 76.77, 76.79, 76.81, 77.08, 77.11, 122.77, 122.85, 122.88, 159.45, 159.47, 159.50, 159.52, 172.19 |

TABLE 8-continued

| Example No. | Condition | Chemical shift δ (ppm) |
|---|---|---|
| 29 | 175 MHz, $CD_3OD$ | 14.41, 23.71, 26.58, 30.39, 30.67, 30.75, 33.04, 34.30, 63.20, 63.57, 63.60, 70.56, 70.59, 71.17, 71.22, 71.68, 71.74, 74.23, 74.31, 74.41, 74.48, 77.74, 77.80, 77.87, 77.91, 76.80, 123.04, 159.27, 159.34, 172.22 |

EXAMPLES 30-98

Compounds of the formula (I) in which $R^1$ and $R^2$ represent groups shown in the following Tables 9-15 were produced by the same method as in the production method in Examples 1-29. The resultant products were subjected to high resolution mass analysis, infrared absorption spectrum, $^1$H-NMR and $^{13}$C-NMR measurements, and their structures were confirmed based on the measurement results.

TABLE 9

| Example No. | $R^1$ | $R^2$ |
|---|---|---|
| 30 | —$CH_2CH(OH)CH_2OCH_3$ | H |
| 31 | —$CH_2CH(OH)CH_2O(CH_2)_2CH_3$ | H |
| 32 | —$CH_2CH(OH)CH_2OCH_2CH=CH_2$ | H |
| 33 | —$CH_2CH(OH)CH_2OCH_2CH=CHCH_3$ | H |
| 34 | —$CH_2CH(OH)CH_2OCH_2CH_2CH=CH_2$ | H |
| 35 | —$CH_2CH(OH)CH_2O(CH_2)_4CH_3$ | H |
| 36 | —$CH_2CH(OH)CH_2O(CH_2)_5CH_3$ | H |
| 37 | —$CH_2CH(OH)CH_2O(CH_2)_6CH_3$ | H |
| 38 | —$CH_2CH(OH)CH_2O(CH_2)_{10}CH_3$ | H |

TABLE 10

| Example No. | $R^1$ | $R^2$ |
|---|---|---|
| 39 | —$CH_2CH(OH)CH_2O(CH_2)_{11}CH_3$ | H |
| 40 | —$CH_2CH(OH)CH_2O(CH_2)_{12}CH_3$ | H |
| 41 | —$CH_2CH(OH)CH_2O(CH_2)_{13}CH_3$ | H |
| 42 | —$CH_2CH(OH)CH_2O(CH_2)_{19}CH_3$ | H |
| 43 | —$CH_2CH(OH)CH_2OCH(CH_3)_2$ | H |
| 44 | —$CH_2CH(OH)CH_2O$-phenyl | H |
| 45 | —$CH_2CH(OH)CH_2OC(CH_3)_3$ | H |
| 46 | —$CH_2CH(OH)(CH_2)_7CH_3$ | H |
| 47 | —$CH_2CH(OH)(CH_2)_{13}CH_3$ | H |
| 48 | H | —$CH_2CH(OH)CH_2O(CH_2)_3CH_3$ |
| 49 | H | —$CH_2CH(OH)(CH_2)_3CH_3$ |

TABLE 11

| Example No. | $R^1$ | $R^2$ |
|---|---|---|
| 50 | H | —$CH_2CH(OH)(CH_2)_7CH_3$ |
| 51 | H | 2-methyl-3-hydroxycyclohexyl |

TABLE 11-continued

| Example No. | R¹ | R² |
|---|---|---|
| 52 | —CH₂CH(OH)CH₂OH | —CH₂CH=CHCH₃ |
| 53 | —CH₂CH(OH)CH₂O(CH₂)₃CH₃ | —CH₂CH=CHCH₃ |
| 54 | —CH₂CH(OH)CH₂O(CH₂)₃CH₃ | —CH₂-C₆H₅ |
| 55 | —CH₂CH(OH)CH₂O-C₆H₅ | —CH₂CH=CH₂ |
| 56 | —CH₂CH(OH)CH₂O-C₆H₅ | —CH₂-C₆H₅ |
| 57 | —CH₂CH(OH)CH₂OH | —(CH₂)₃CH₃ |
| 58 | —CH₂CH(OH)CH₂OH | —(CH₂)₅CH₃ |
| 59 | —CH₂CH(OH)CH₂OH | —(CH₂)₆CH₃ |
| 60 | —CH₂CH(OH)CH₂OH | —(CH₂)₈CH₃ |

TABLE 12

| Example No. | R¹ | R² |
|---|---|---|
| 61 | —CH₂CH(OH)CH₂OH | —(CH₂)₉CH₃ |
| 62 | —CH₂CH(OH)CH₂OH | —(CH₂)₁₀CH₃ |
| 63 | —CH₂CH(OH)CH₂OH | —(CH₂)₁₁CH₃ |
| 64 | —CH₂CH(OH)CH₂OH | —(CH₂)₁₂CH₃ |
| 65 | —CH₂CH(OH)CH₂OH | —(CH₂)₁₃CH₃ |
| 66 | —CH₂CH(OH)CH₂OCH₂CH₃ | —CH₂CH₃ |
| 67 | —CH₂CH(OH)CH₂OCH₂CH₃ | —(CH₂)₅CH₃ |
| 68 | —CH₂CH(OH)CH₂O(CH₂)₃CH₃ | —CH₂CH₃ |
| 69 | —CH₂CH(OH)CH₂O(CH₂)₃CH₃ | —(CH₂)₅CH₃ |
| 70 | —CH₂CH(OH)CH₂O(CH₂)₃CH₃ | —(CH₂)₇CH₃ |
| 71 | —CH₂CH(OH)CH₂O(CH₂)₃CH₃ | —(CH₂)₁₁CH₃ |

TABLE 13

| Example No. | R¹ | R² |
|---|---|---|
| 72 | —CH₂CH(OH)CH₂O(CH₂)₃CH₃ | —(CH₂)₁₅CH₃ |
| 73 | —CH₂CH(OH)CH₂O(CH₂)₇CH₃ | —(CH₂)₇CH₃ |
| 74 | —CH₂CH(OH)CH₂O(CH₂)₇CH₃ | —(CH₂)₁₅CH₃ |
| 75 | —CH₂CH(OH)CH₂O(CH₂)₁₁CH₃ | —(CH₂)₇CH₃ |
| 76 | —CH₂CH(OH)CH₂O(CH₂)₁₁CH₃ | —(CH₂)₁₅CH₃ |
| 77 | —CH₂CH(OH)CH₂O(CH₂)₁₅CH₃ | —(CH₂)₇CH₃ |
| 78 | —CH₂CH(OH)CH₂O(CH₂)₁₅CH₃ | —(CH₂)₁₅CH₃ |
| 79 | —CH₂CH(OH)(CH₂)₇CH₃ | —(CH₂)₃CH₃ |
| 80 | —CH₂CH(OH)CH₂O(CH₂)₇CH₃ | —CH₂CH(OH)CH₂OH |
| 81 | —CH₂CH(OH)CH₂O(CH₂)₁₁CH₃ | —CH₂CH(OH)CH₂OH |
| 82 | —CH₂CH(OH)CH₂O(CH₂)₁₅CH₃ | —CH₂CH(OH)CH₂OH |

TABLE 14

| Example No. | R¹ | R² |
|---|---|---|
| 83 | —CH₂CH(OH)(CH₂)₇CH₃ | —CH₂CH(OH)CH₂OH |
| 84 | —CH₂CH(OH)CH₂OH | —CH₂CH(OH)CH₂O(CH₂)₇CH₃ |
| 85 | —CH₂CH(OH)CH₂OH | —CH₂CH(OH)CH₂O(CH₂)₁₁CH₃ |
| 86 | —CH₂CH(OH)CH₂OH | —CH₂CH(OH)CH₂O(CH₂)₁₅CH₃ |
| 87 | —CH₂CH(OH)CH₂O(CH₂)₃CH₃ | —CH₂CH(OH)CH₂O(CH₂)₃CH₃ |
| 88 | —CH₂CH(OH)CH₂O—C₆H₅ | —CH₂CH(OH)CH₂O—C₆H₅ |
| 89 | —CH₂CH(OH)CH₂O(CH₂)₃CH₃ | —CH₂CH(OH)CH₂O(CH₂)₇CH₃ |
| 90 | —CH₂CH(OH)CH₂O(CH₂)₃CH₃ | —CH₂CH(OH)CH₂O(CH₂)₁₁CH₃ |
| 91 | —CH₂CH(OH)CH₂O(CH₂)₇CH₃ | —CH₂CH(OH)CH₂O(CH₂)₇CH₃ |
| 92 | —CH₂CH(OH)CH₂O(CH₂)₇CH₃ | —CH₂CH(OH)CH₂O(CH₂)₁₅CH₃ |

TABLE 15

| Example No. | R¹ | R² |
|---|---|---|
| 93 | —CH₂CH(OH)CH₂O(CH₂)₁₁CH₃ | —CH₂CH(OH)CH₂O(CH₂)₁₅CH₃ |
| 94 | —CH₂CH(OH)CH₂O(CH₂)₃CH₃ | —CH₂CH(CH₂)₃CH₃ (OH) |
| 95 | —CH₂CH(OH)(CH₂)₇CH₃ | —CH₂CH(OH)(CH₂)₃CH₃ |
| 96 | —CH₂CH₃ | —CH₂CH(OH)CH₂OH |
| 97 | —CH₂CH₃ | —CH₂CH(OH)CH₂O(CH₂)₃CH₃ |
| 98 | —CH₂CH₃ | —CH₂CH(OH)(CH₂)₇CH₃ |

The measurement results of high resolution mass analysis of the products obtained in Examples 30 to 98 are shown in Tables 16-18.

TABLE 16

| Example No. | Method | Measured value (Theoretical value) |
|---|---|---|
| 30 | F+ | 265.0939 (265.0924) |
| 31 | E+ | 292.1163 (292.1158) |
| 32 | E+ | 290.1006 (290.1001) |
| 33 | E+ | 304.1149 (304.1158) |
| 34 | E+ | 304.1160 (304.1158) |
| 35 | E+ | 320.1468 (320.1471) |
| 36 | E+ | 334.1633 (334.1627) |
| 37 | E+ | 348.1775 (348.1784) |
| 38 | E+ | 404.2405 (402.2410) |
| 39 | F+ | 419.2644 (419.2645) |
| 40 | E+ | 432.2725 (432.2723) |
| 41 | F+ | 447.2943 (447.2958) |
| 42 | F+ | 531.3901 (531.3897) |
| 43 | F+ | 293.1239 (293.1236) |
| 44 | F+ | 327.1064 (327.1079) |
| 45 | F+ | 307.1369 (307.1393) |
| 46 | F+ | 333.1926 (333.1913) |
| 47 | F+ | 417.2852 (417.2853) |
| 48 | E+ | 306.1319 (306.1314) |
| 49 | E+ | 276.1201 (276.1209) |
| 50 | E+ | 332.1826 (332.1835) |
| 51 | E+ | 274.1044 (274.1053) |
| 52 | E+ | 305.1242 (305.1236) |

TABLE 16-continued

| Example No. | Method | Measured value (Theoretical value) |
|---|---|---|
| 53 | E+ | 360.1791 (360.1784) |
| 54 | E+ | 396.1782 (396.1784) |

TABLE 17

| Example No. | Method | Measured value (Theoretical value) |
|---|---|---|
| 55 | E+ | 366.1309 (366.1314) |
| 56 | E+ | 416.1469 (416.1471) |
| 57 | E+ | 306.1320 (306.1314) |
| 58 | E+ | 334.1632 (334.1627) |
| 59 | E+ | 348.1789 (348.1784) |
| 60 | E+ | 376.2090 (376.2097) |
| 61 | E+ | 390.2259 (390.2253) |
| 62 | E+ | 404.2418 (404.2410) |
| 63 | E+ | 418.2563 (418.2566) |
| 64 | E+ | 432.2715 (432.2723) |
| 65 | E+ | 446.2881 (446.2879) |
| 66 | E+ | 306.1306 (306.1314) |
| 67 | E+ | 362.1936 (362.1940) |
| 68 | E+ | 334.1620 (334.1627) |
| 69 | E+ | 390.2248 (390.2253) |
| 70 | E+ | 418.2565 (418.2566) |
| 71 | E+ | 474.3201 (474.3192) |
| 72 | E+ | 530.3825 (530.3818) |
| 73 | E+ | 474.3189 (474.3192) |
| 74 | E+ | 586.4446 (586.4444) |
| 75 | E+ | 530.3816 (530.3818) |
| 76 | E+ | 642.5077 (642.5070) |
| 77 | E+ | 586.4438 (586.4444) |
| 78 | E+ | 698.5691 (698.5696) |
| 79 | E+ | 388.2458 (388.2461) |

TABLE 18

| Example No. | Method | Measured value (Theoretical value) |
|---|---|---|
| 80 | E+ | 436.2315 (436.2308) |
| 81 | E+ | 492.2928 (492.2934) |
| 82 | E+ | 548.3552 (548.3560) |
| 83 | E+ | 406.2210 (406.2202) |
| 84 | E+ | 436.2306 (436.2308) |
| 85 | E+ | 492.2933 (492.2934) |
| 86 | E+ | 548.3551 (548.3560) |
| 87 | E+ | 436.2310 (436.2308) |
| 88 | E+ | 476.1676 (476.1682) |
| 89 | E+ | 492.2935 (492.2934) |
| 90 | E+ | 548.3565 (548.3560) |
| 91 | E+ | 548.3552 (548.3560) |
| 92 | E+ | 660.4813 (660.4812) |
| 93 | F+ | 739.5329 (739.5336)[+Na] |
| 94 | E+ | 406.2198 (406.2202) |
| 95 | E+ | 432.2714 (432.2723) |
| 96 | E+ | 278.0993 (278.1001) |
| 97 | E+ | 334.1619 (334.1627) |
| 98 | E+ | 360.2155 (360.2148) |

The results of measurement of infrared absorption spectrum of the products obtained in Examples 30 to 98 are shown in Tables 19-21.

TABLE 19

| Example No. | Condition* | Measured value (Wavenumber cm$^{-1}$) |
|---|---|---|
| 30 | TlBr | 3416, 1761, 1695 |
| 31 | As$_2$Se$_3$ | 3268, 2964, 1761, 1695 |
| 32 | TlBr | 3383, 2943, 1759, 1693 |
| 33 | TlBr | 3393, 2920, 1761, 1695 |
| 34 | TlBr | 3630, 1749, 1684 |
| 35 | As$_2$Se$_3$ | 3369, 2961, 2932, 2872, 1749, 1697 |
| 36 | As$_2$Se$_3$ | 3393, 2932, 1746, 1695 |
| 37 | As$_2$Se$_3$ | 3393, 2930, 2858, 1747, 1697 |
| 38 | KBr | 3404, 2924, 2855, 1747, 1697 |
| 39 | KBr | 3402, 2922, 2853, 1747, 1697 |
| 40 | KBr | 3404, 2922, 2853, 1746, 1695 |
| 41 | KBr | 3458, 2920, 2851, 1746, 1697 |
| 42 | KBr | 3402, 2918, 2851, 1747, 1697 |
| 43 | TlBr | 3416, 2974, 1761, 1695 |
| 44 | KBr | 3668, 1761, 1697 |
| 45 | TlBr | 3225, 2974, 1761, 1695 |
| 46 | KBr | 3464, 2926, 2853, 1746, 1674 |
| 47 | KBr | 3464, 2920, 2851, 1746, 1676 |
| 48 | ATR | 3360, 2934, 2872, 1746, 1667, |
| 49 | ATR | 3379, 2955, 2932, 1746, 1663 |
| 50 | ATR | 3319, 2924, 2853, 1717, 1576, |
| 51 | ATR | 3374, 2938, 2864, 1746, 1663 |
| 52 | TlBr | 3310, 1749, 1670 |
| 53 | ATR | 3375, 2957, 2934, 2864, 1762, 1676 |
| 54 | ATR | 3393, 2934, 2872, 1759, 1674 |

TABLE 20

| Example No. | Condition* | Measured value (Wavenumber cm$^{-1}$) |
|---|---|---|
| 55 | ATR | 3383, 1734, 1667, 1599, 1497 |
| 56 | ATR | 3343, 1746, 1728, 1663, 1599, 1495, 1244 |
| 57 | TlBr | 3393, 1749, 1674 |
| 58 | TlBr | 3379, 2934, 1751, 1674 |
| 59 | TlBr | 3389, 2932, 1751, 1674 |
| 60 | KBr | 3327, 2924, 2853, 1761, 1684 |
| 61 | KBr | 3317, 2959, 2924, 1759, 1682 |
| 62 | KBr | 3300, 2916, 2851, 1761, 1684 |
| 63 | KBr | 3422, 2918, 2851, 1749, 1676 |
| 64 | KBr | 3289, 2916, 2849, 1761, 1684 |
| 65 | KBr | 3326, 2920, 2849, 1759, 1680 |
| 66 | ATR | 3379, 2976, 2878, 1749, 1670 |
| 67 | ATR | 3310, 2932, 2874, 1749, 1676 |
| 68 | ATR | 3339, 2959, 2936, 2874, 1759, 1674 |
| 69 | ATR | 3396, 2934, 2872, 1755, 1676 |
| 70 | TlBr | 3339, 2930, 2860, 1751, 1678 |
| 71 | TlBr | 3368, 2926, 2855, 1751, 1676 |
| 72 | TlBr | 3368, 2924, 2855, 1749, 1674 |
| 73 | TlBr | 3369, 2928, 2856, 1753, 1676 |
| 74 | TlBr | 3306, 2920, 2853, 1655 |
| 75 | TlBr | 3369, 2924, 2855, 1761, 1676 |
| 76 | TlBr | 3308, 2922, 2853, 1749, 1672 |
| 77 | TlBr | 3380, 2920, 2853, 1761, 1670 |
| 78 | TlBr | 3348, 2916, 2849, 1655 |
| 79 | TlBr | 3369, 2959, 2928, 2856, 1757, 1676 |

TABLE 21

| Example No. | Condition* | Measured value (Wavenumber cm$^{-1}$) |
|---|---|---|
| 80 | KBr | 3395, 2930, 2858, 1753, 1674 |
| 81 | KBr | 3368, 2926, 2855, 1751, 1676 |
| 82 | KBr | 3315, 2918, 2851, 1749, 1670 |
| 83 | ATR | 3352, 2924, 2855, 1748, 1668, |
| 84 | TlBr | 3368, 2928, 2858, 1749, 1674 |
| 85 | TlBr | 3368, 2924, 2855, 1752, 1676 |
| 86 | TlBr | 3369, 2922, 2853, 1751, 1674 |
| 87 | TlBr | 3393, 2936, 2874, 1751, 1676 |
| 89 | TlBr | 3393, 2930, 2860, 1755, 1678 |
| 90 | TlBr | 3400, 2926, 2856, 1755, 1678 |
| 91 | TlBr | 3400, 2928, 2856, 1757, 1676 |
| 92 | ATR | 3393, 2920, 2853, 1749, 1674 |
| 93 | TlBr | 3369, 2920, 2853, 1751, 1672 |
| 94 | TlBr | 3393, 2959, 2934, 2874, 1755, 1674 |
| 95 | TlBr | 3368, 2928, 2858, 1751, 1672 |
| 96 | TlBr | 3358, 2938, 2884, 1744, 1663 |
| 97 | TlBr | 3404, 2959, 2936, 2874, 1751, 1672 |
| 98 | TlBr | 3369, 2928, 2856, 1750, 1674 |

The results of measurement of ¹H-NMR of the products obtained in Examples 30 to 98 are shown in Tables 22-28.

TABLE 22

| Example No. | Condition | Chemical shift δ (ppm) |
|---|---|---|
| 30 | 500 MHz, CD₃OD | 3.37 (3H, d-like), 3.47 (2H, m), 3.65 (2H, m), 3.88 (1H, m), 4.03 (1H, m, H-8), 4.43/4.45 (dd, 1H), 4.56/4.60 (1H, dd), 4.81 (1H, d) |
| 31 | 600 MHz, CD₃OD | 0.92 (3H, m), 1.59 (2H, m,), 3.44 (2H, m), 3.50 (2H, m), 3.65 (2H, m), 3.88 (1H, m), 4.03 (1H, m), 4.44/4.46 (1H, dd), 4.59/4.62 (1H, dd), 4.81 (1H, d) |
| 32 | 500 MHz, CD₃OD | 3.52 (2H, m), 3.66 (2H, m), 3.88 (1H, m), 4.02 (2H, m), 4.05 (1H, m), 4.45/4.47 (1H, dd), 4.59/4.62 (1H, dd), 4.81 (1H, d), 5.16 (1H, m), 5.29 (1H, m), 5.91 (1H, m) |
| 33 | 500 MHz, CD₃OD | 1.70 (3H, m), 3.49 (2H, m), 3.65 (2H, m), 3.88 (1H, m), 3.95 (2H, m), 4.45/4.47 (1H, dd), 4.59/4.62 (1H, dd), 4.81 (1H, d), 5.57 (1H, m), 5.74 (1H, m) |
| 34 | 500 MHz, CD₃OD | 2.32 (2H, m), 3.51 (2H, m), 3.55 (2H, m), 3.66 (2H, m), 3.88 (1H, m), 4.03 (1H, m), 4.44/4.46 (1H, dd), 4.58/4.61 (1H, dd,), 4.81 (1H, d), 5.01 (1H, m), 5.08 (1H, m), 5.83 (1H, m) |
| 35 | 600 MHz, CD₃OD | 0.91 (3H, t), 1.34 (4H, m), 1.58 (2H, m), 3.47 (2H, m), 3.50 (2H, m), 3.65 (2H, m), 3.88 (1H, m), 4.03 (1H, m), 4.44/4.46 (1H, dd), 4.59/4.62 (1H, dd), 4.81 (1H, d) |
| 36 | 600 MHz, CD₃OD | 0.91 (3H, t), 1.33 (6H, m), 1.57 (2H, m), 3.47 (2H, m), 3.50 (2H, m), 3.65 (2H, m), 3.88 (1H, m), 4.03 (1H, m), 4.44/4.46 (1H, dd), 4.59/4.62 (1H, dd), 4.81 (1H, d) |
| 37 | 600 MHz, CD₃OD | 0.89 (3H, t), 1.29 (8H, brs), 1.57 (2H, m), 3.45 (2H, m), 3.50 (2H, m), 3.66 (2H, m), 3.88 (1H, m), 4.03 (1H, m), 4.44/4.46 (1H, dd), 4.59/4.62 (1H, dd), 4.81 (1H, d) |
| 38 | 500 MHz, CD₃OD | 0.89 (3H, t), 1.28 (18H, brs), 1.57 (2H, m), 3.46 (2H, m), 3.50 (2H, m), 3.65 (2H, m), 3.88 (1H, m), 4.03 (1H, m), 4.44/4.46 (1H, dd), 4.59/4.62 (1H, dd), 4.81 (1H, d) |
| 39 | 600 MHz, CD₃OD | 0.89 (3H, t), 1.28 (18H, brs), 1.57 (2H, m), 3.47 (2H, m), 3.51 (2H, m), 3.65 (2H, m), 3.88 (1H, m), 4.03 (1H, m), 4.44/4.47 (1H, dd), 4.59/4.62 (1H, dd), 4.81 (1H, d) |

TABLE 23

| Example No. | Condition | Chemical shift δ (ppm) |
|---|---|---|
| 40 | 600 MHz, CD₃OD | 0.89 (3H, t), 1.28 (22H, brs), 1.57 (2H, m), 3.47 (2H, m), 3.51 (2H, m), 3.65 (2H, m), 3.88 (1H, m), 4.03 (1H, m), 4.44/4.46 (1H, dd), 4.59/4.62 (1H, dd), 4.81 (1H, d) |
| 41 | 600 MHz, CD₃OD | 0.89 (3H, t), 1.28 (22H, brs), 1.57 (2H, m), 3.47 (2H, m), 3.51 (2H, m), 3.65 (2H, m), 3.88 (1H, m), 4.03 (1H, m), 4.44/4.46 (1H, dd), 4.59/4.62 (1H, dd), 4.81 (1H, d) |
| 42 | 600 MHz, CD₃OD | 0.89 (3H, t), 1.28 (34H, brs), 1.57 (2H, m), 3.47 (2H, m), 3.51 (2H, m), 3.65 (2H, m), 3.88 (1H, m), 4.03 (1H, m), 4.44/4.46 (1H, dd), 4.59/4.62 (1H, dd), 4.81 (1H, d) |
| 43 | 500 MHz, CD₃OD | 1.15 (6H, m), 3.51 (2H, m), 3.62 (1H, m), 3.65 (2H, m), 3.88 (1H, m), 3.99 (1H, m), 4.44/4.46 (1H, dd), 4.59/4.61 (1H, dd), 4.81 (1H, d) |
| 44 | 500 MHz, CD₃OD | 3.65 (2H, m), 3.89 (1H, m), 4.06 (1H, m), 4.26 (1H, m), 4.59/4.60 (1H, dd), 4.70/4.73 (1H, dd), 4.82 (1H, m), 6.93 (3H, m), 7.26 (2H, m) |
| 45 | 600 MHz, CD₃OD | 1.20 (9H, s), 3.45 (2H, m), 3.66 (2H, m), 3.88 (1H, m), 3.94 (1H, m), 4.45/4.46 (1H, dd), 4.60/4.63 (1H, dd), 4.810/4.812 (1H, d) |
| 46 | 600 MHz, CD₃OD | 0.89 (3H, t), 1.30 (10H, brs), 1.48 (4H, m), 3.66 (2H, m), 3.88 (4H, m), 4.28/4.31 (1H, dd), 4.50/4.53 (1H, dd), 4.81 (1H, d) |
| 47 | 500 MHz, CD₃OD | 0.89 (3H, t), 1.28 (22H, brs), 1.48 (4H, m), 3.66 (2H, m), 3.88 (4H, m), 4.27/4.31 (1H, dd), 4.50/4.53 (1H, dd), 4.81 (1H, d) |
| 48 | 400 MHz, CD₃OD | 0.92 (3H, t), 1.37 (2H, m), 1.55 (2H, m), 3.49 (4H, m), 3.67 (2H, brd), 3.92 (2H, m), 3.99 (1H, m), 4.06/4.07 (1H, dd), 4.81 (1H, brs) |
| 49 | 400 MHz, CD₃OD | 0.92 (3H, t), 1.33 (4H, m), 1.45 (2H, m), 3.66 (2H, brd), 3.77 (1H, m)3.82 (1H, m)3.91 (1H, m), 4.02 (1H, m), 4.84 (1H, d) |
| 50 | 700 MHz, CD3OD | 0.89 (3H, t), 1.30 (10H, brs), 1.46 (2H, m), 3.66 (2H, brd), 3.77 (1H, m)3.82 (1H, m), 3.91 (1H, m), 3.99 (1H, m), 4.81 (1H, d) |
| 51 | 400 MHz, CD3OD | 1.30 (4H, m), 1.70 (2H, m), 1.98 (1H, m), 2.11 (1H, m), 3.57 (1H, m), 3.67 (3H, m), 3.91 (1H, m), 4.86 (1H, m) |

TABLE 24

| Example No. | Condition | Chemical shift δ (ppm) |
|---|---|---|
| 52 | 700 MHz, CD$_3$OD | 1.71 (3H, m), 3.59 (2H, m), 3.65 (2H, m), 3.90 (2H, m), 4.46 (2H, m), 4.58 (1H, m), 4.86 (1H, m), 5.68 (1H, m), 5.80 (1H, m) |
| 53 | 500 MHz, CD$_3$OD | 0.93 (3H, t), 1.39 (2H, m), 1.56 (2H, m), 1.72 (3H, m), 3.48 (4H, m), 3.65 (2H, m), 3.89 (1H, m), 4.01 (1H, m), 4.46, (2H, m), 4.44/4.45 (1H, dd), 4.58/4.59 (1H, dd), 4.86 (1H, d) |
| 54 | 500 MHz, CD$_3$OD | 0.90 (3H, t), 1.35 (2H, m), 1.51 (2H, m), 3.38 (2H, m), 3.41 (2H, m), 3.66 (2H, brd), 3.88, (1H, dt-like), 3.91 (1H, m), 4.24,/4.26 (1H, dd), 4.37/4.38 (1H, dd), 4.852/4.857 (1H, d), 5.05 (2H, m), 7.42 (2H, m), 7.35 (3H, m) |
| 55 | 400 MHz, CD$_3$OD | 3.65 (2H, m), 3.91 (1H, m), 4.05 (2H, m), 4.24 (1H, m), 4.55 (2H, m), 4.59/4.61 (1H, dd), 4.69/4.70 (1H, dd), 4.88, (1H, brd), 5.23 (1H, m), 5.34 (1H, m), 6.03 (1H, m) 6.93 (3H, m), 7.26 (2H, m) |
| 56 | 400 MHz, CD$_3$OD | 3.66 (2H, brd), 3.88 (1H, m), 3.91 (2H, m), 4.12 (1H, m), 4.36/4.38 (1H, dd), 4.43/4.45 (1H, dd), 4.86, (1H, d), 5.06 (1H, brs), 6.91 (3H, m), 7.26 (5H, m), 7.39 (2H, m) |
| 57 | 500 MHz, CD$_3$OD | 0.96 (3H, t), 1.45 (2H, m), 1.68 (2H, m), 3.60 (2H, brd), 3.65 (2H, m), 3.90 (1H, m), 3.91 (1H, m), 4.03 (1H, m), 4.47/4.48 (1H, dd), 4.57/4.59 (1H, dd), 4.86 (1H, d) |
| 58 | 500 MHz, CD$_3$OD | 0.91 (3H, t-like), 1.32 (2H, m), 1.33 (2H, m), 1.42 (2H, m), 1.69 (2H, m), 3.60 (2H, brd), 3.65 (2H, m), 3.90 (1H, m), 3.91 (1H, m), 4.03 (1H, m, ), 4.47/4.48 (1H, dd), 4.57/4.59 (1H, dd), 4.86 (1H, m) |
| 59 | 600 MHz, CD$_3$OD | 0.90 (3H, t), 1.33 (4H, m), 1.41 (2H, m), 1.70 (2H, m), 3.60 (2H, m), 3.65 (2H, m), 3.90 (1H, m), 3.91 (1H, m), 4.02 (1H, m), 4.47/4.48 (1H, dd), 4.57/4.59 (1H, dd), 4.86 (1H, d) |
| 60 | 600 MHz, CD$_3$OD | 0.90 (3H, t), 1.31 (10H, m), 1.41 (2H, m), 1.70 (2H, m), 3.60 (2H, brd), 3.65 (2H, m), 3.90 (1H, m), 3.91 (1H, m), 4.03 (1H, m), 4.47/4.48 (1H, dd), 4.57/4.59 (1H, dd), 4.86 (1H, m) |
| 61 | 600 MHz, CD$_3$OD | 0.89 (3H, t), 1.30 (12H, brs), 1.41 (2H, m), 1.69 (2H, m), 3.60 (2H, brd), 3.65 (2H, m), 3.90 (1H, m), 3.91 (1H, m), .02 (1H, m), 4.47/4.48 (1H, dd), 4.57/4.59 (1H, dd), 4.86 (1H, m) |

TABLE 25

| Example No. | Condition | Chemical shift δ (ppm) |
|---|---|---|
| 62 | 600 MHz, CD$_3$OD | 0.89 (3H, t), 1.29 (14H, brs), 1.41 (2H, m), 1.70 (2H, m), 3.60 (2H, brd), 3.65 (2H, m), 3.90 (1H, m), 3.91 (1H, m), 4.02 (1H, m), 4.47/4.48 (1H, dd), 4.57/4.59 (1H, dd), 4.86 (1H, d) |
| 63 | 500 MHz, CD$_3$OD | 0.89 (3H, t), 1.29 (16H, brs), 1.41 (2H, m), 1.70 (2H, m), 3.60 (2H, brd), 3.65 (2H, m), 3.90 (1H, m), 3.91 (1H, m), 4.02 (1H, m), 4.47/4.48 (1H, dd), 4.57/4.59 (1H, dd), 4.86 (1H, m) |
| 64 | 500 MHz, CD$_3$OD | 0.89 (3H, t), 1.28 (18H, brs), 1.41 (2H, m), 1.70 (2H, m), 3.60 (2H, brd), 3.65 (2H, m), 3.90 (1H, m), 3.91 (1H, m), 4.02 (1H, m), 4.47/4.48 (1H, dd), 4.57/4.59 (1H, dd), 4.86 (1H, d) |
| 65 | 500 MHz, CD$_3$OD | 0.89 (3H, t), 1.28 (20H, brs), 1.41 (2H, m), 1.70 (2H, m), 3.60 (2H, brd), 3.65 (2H, m), 3.90 (1H, m), 3.91 (1H, m), 4.02 (1H, m), 4.47/4.48 (1H, dd), 4.57/4.59 (1H, dd), 4.86 (1H, m) |
| 66 | 700 MHz, CD$_3$OD | 1.19 (3H, m), 1.30 (3H, m), 3.51 (2H, m), 3.54 (2H, m), 3.66 (2H, m), 3.90 (1H, m), 4.02 (1H, m), 4.09 (2H, m), 4.46/4.47 (1H, dd), 4.58/4.59 (1H, dd), 4.87 (1H, d) |
| 67 | 500 MHz, CD$_3$OD | 0.91 (3H, m), 1.17 (3H, m), 1.34 (2H, m), 1.42 (4H, m), 1.69 (2H, m), 3.52 (4H, m), 3.65 (2H, m), 3.89 (1H, m), 4.03 (4H, m), 4.46 (1H, dd), 4.58/4.59 (1H, dd), 4.86 (1H, m) |
| 68 | 500 MHz, CD$_3$OD | 0.93 (3H, m), 1.30 (3H, t), 1.40 (2H, m), 1.56 (2H, m), 3.49 (4H, m), 3.66 (2H, m), 3.90 (1H, m), 4.02 (1H, m), 4.46/4.47 (1H, dd), 4.59/4.60 (1H, dd), 4.86 (1H, d) |
| 69 | 500 MHz, CD$_3$OD | 0.92 (6H, m), 1.34 (4H, m), 1.39 (4H, m), 1.55 (2H, m), 1.69 (2H, m), 3.48 (4H, m), 3.65 (2H, m), 3.90 (1H, m), 4.03 (3H, m), 4.46 (1H, dd), 4.58/4.59 (1H, dd), 4.86 (1H, d) |
| 70 | 600 MHz, CD$_3$OD | 0.90 (3H, t), 0.93 (3H, t), 1.32 (8H, m), 1.40 (4H, m), 1.54 (2H, m), 1.69 (2H, m), 3.48 (4H, m), 3.65 (2H, m), 3.90 (1H, m), 4.01 (3H, m), 4.45/4.46 (1H, dd), 4.58/4.59 (1H, dd), 4.86 (1H, d) |
| 71 | 700 MHz, CD$_3$OD | 0.89 (3H, t), 0.93 (3H, t), 1.29 (18H, brs), 1.40 (2H, m), 1.56 (2H, m), 1.69 (2H, m), 3.49 (4H, m), 3.65 (2H, m), 3.90 (1H, m), 4.02 (3H, m), 4.45/4.46 (1H, dd), 4.59 (1H, m), 4.87 (1H, brs) |

TABLE 26

| Example No. | Condition | Chemical shift δ (ppm) |
|---|---|---|
| 72 | 600 MHz, CD$_3$OD | 0.89 (3H, t), 0.93 (3H, t), 1.28 (24H, brs), 1.39 (4H, m), 1.56 (2H, m), 1.69 (2H, m), 3.49 (4H, m), 3.65 (2H, m), 3.90 (1H, m), 4.02 (3H, m), 4.45/4.46 (1H, dd), 4.59 (1H, dd), 4.85 (1H, brs) |
| 73 | 600 MHz, CD$_3$OD | 0.90 (6H, m), 1.30 (18H, brs), 1.42 (2H, m), 1.56 (2H, m), 1.69 (2H, m), 3.47 (4H, m), 3.65 (2H, m), 3.90 (1H, m), 4.01 (3H, m), 4.46 (1H, dd), 4.59/4.60 (1H, dd), 4.86 (1H, d) |
| 74 | 600 MHz, d$_6$-DMSO 40° C. | 0.90 (6H, m), 1.24 (34H, brs), 1.34 (2H, m), 1.48 (2H, m), 1.60 (2H, m), 3.38 (4H, m), 3.46 (2H, m), 3.72 (1H, m), 3.87 (1H, m), 3.94 (2H, m), 4.25/4.31 (1H, dd), 4.42/4.45 (1H, dd), 4.82 (1H, d) |
| 75 | 600 MHz, d$_6$-DMSO, 40° C. | 0.90 (6H, m), 1.24 (34H, brs), 1.34 (2H, m), 1.48 (2H, m), 1.60 (2H, m), 3.38 (4H, m), 3.54 (2H, m), 3.72 (1H, m), 3.87 (1H, m), 3.94 (1H, m), 4.25/4.31 (1H, dd), 4.42/4.45 (1H, dd), 4.82 (1H, d) |
| 76 | 500 MHz, d$_6$-DMSO, 40° C. | 0.85 (6H, m), 1.24 (46H, brs), 1.34 (2H, m), 1.48 (2H, m), 1.60 (2H, m), 3.37 (4H, m), 3.45 (2H, m), 3.72 (1H, m), 3.89 (1H, m), 3.93 (2H, m), 4.25/4.30 (1H, dd), 4.42/4.46 (1H, dd), 4.81, (1H, m) |
| 77 | 600 MHz, d$_6$-DMSO, 40° C. | 0.86 (6H, m), 1.24 (36H, brs), 1.34 (2H, m), 1.48 (2H, m), 1.61 (2H, m), 3.38 (4H, m), 3.45 (2H, m), 3.72 (1H, m), 3.88 (1H, m), 3.93 (2H, m), 4.25/4.31 (1H, dd), 4.42/4.45 (1H, dd), 4.81 (1H, m) |
| 78 | 500 MHz, d$_6$-DMSO, 40° C. | 0.85 (6H, m), 1.24 (54H, brs), 1.34 (2H, m), 1.47 (2H, m), 1.60 (2H, m), 3.38 (4H, m), 3.45 (2H, m), 3.71 (1H, m), 3.86 (1H, m), 3.93 (2H, m), 4.24, 4.30 (1H, dd), 4.43/4.46 (1H, dd), 4.81 (1H, m) |
| 79 | 600 MHz, CD$_3$OD | 0.89 (3H, t), 0.96 (3H, t), 1.32 (12H, m), 1.45 (2H, m), 1.49 (2H, m), 3.65 (2H, m), 3.87 (1H, m), 3.90 (1H, m), 4.03 (4H, m), 4.31/4.32 (1H, dd), 4.47/4.48 (1H, dd), 4.85/4.86 (1H, d) |
| 80 | 600 MHz, CD$_3$OD | 0.89 (3H, t), 1.32 (10H, m), 1.57 (2H, m), 3.49 (4H, m), 3.67 (2H, m), 3.59 (2H, m), 3.90 (2H, m), 4.01 (2H, m), 4.15 (1H, m), 4.53 (1H, m), 4.64 (1H, m), 4.88 (1H, m) |
| 81 | 600 MHz, CD$_3$OD | 0.89 (3H, t), 1.28 (18H, brs), 1.57 (2H, m), 3.49 (4H, m), 3.58 (2H, m), 3.67 (2H, m), 3.90 (2H, m), 4.01 (2H, m), 4.15 (1H, m), 4.53 (1H, m), 4.63 (1H, m), 4.84 (1H, brd) |

TABLE 27

| Example No. | Condition | Chemical shift δ (ppm) |
|---|---|---|
| 82 | 600 MHz, CD$_3$OD | 0.89 (3H, t), 1.28 (26H, brs), 1.58 (2H, m), 3.49 (4H, m), 3.59 (2H, m), 3.67 (2H, m), 3.89 (2H, m), 4.00 (2H, m), 4.15 (1H, m), 4.53 (1H, m), 4.63 (1H, m), 4.88 (1H, m) |
| 83 | 600 MHz, CD$_3$OD | 0.89 (3H, m), 1.31 (12H, m), 1.50 (2H, m), 3.58 (2H, m), 3.65 (2H, m), 3.87 (2H, m), 3.91 (1H, m), 4.00 (1H, m), 4.16 (1H, m), 4.41 (1H, m), 4.53 (1H, m), 4.87 (1H, d) |
| 84 | 700 MHz, CD$_3$OD | 0.89 (3H, m), 1.30 (10H, brs), 1.57 (2H, m), 3.48 (4H, m), 3.60 (2H, m), 3.66 (2H, m), 3.92 (3H, m), 3.99 (1H, m), 4.17 (1H, m), 4.53 (1H, m), 4.64 (1H, m), 4.87 (1H, m) |
| 85 | 600 MHz, CD$_3$OD | 0.88 (3H, m), 1.27 (18H, brs), 1.55 (2H, m), 3.45 (4H, m), 3.59 (2H, m), 3.65 (2H, m), 3.90 (2H, m), 3.99 (2H, m), 4.15 (1H, m), 4.51 (1H, m), 4.62 (1H, m), 4.86 (1H, m) |
| 86 | 700 MHz, CD$_3$OD | 0.89 (3H, t), 1.28 (26H, brs), 1.57 (2H, m), 3.48 (4H, m), 3.60 (2H, m), 3.66 (2H, m), 3.92 (2H, m), 3.99 (2H, m), 4.16 (1H, m), 4.51 (1H, m), 4.64 (1H, m), 4.87 (1H, brd) |
| 87 | 700 MHz, CD$_3$OD | 0.92 (3H, t), 0.93 (3H, t), 1.38 (4H, m), 1.56 (4H, m), 3.48 (8H, m), 3.66 (2H, m), 3.90 (1H, m), 4.01 (3H, m), 4.17 (1H, m), 4.52 (1H, m), 4.64 (1H, m), 4.87 (1H, brs) |
| 88 | 400 MHz, CD$_3$OD | 3.66 (2H, brd), 3.88 (1H, m), 3.91 (2H, m), 4.12 (1H, m), 4.36/4.38 (1H, dd), 4.43/4.45 (1H, dd), 4.86, (1H, d), 5.06 (1H, brs), 6.91 (3H, m), 7.26 (5H, m), 7.39 (2H, m) |
| 89 | 500 MHz, CD$_3$OD | 0.88 (3H, t), 0.93 (3H, t), 1.29 (8H, brs), 1.38 (4H, m), 1.56 (4H, m), 3.48 (8H, m), 3.66 (2H, m), 3.91 (1H, m), 4.01 (3H, m), 4.16 (1H, m), 4.51 (1H, m), 4.63 (1H, m), 4.87 (1H, brs) |
| 90 | 600 MHz, d$_6$-DMSO, 40° C. | 0.87 (3H, t), 0.88 (3H, t), 1.24 (18H, brs), 1.32 (2H, m), 1.47 (2H, m), 3.40 (8H, m), 3.56 (2H, m), 3.72 (1H, m), 3.86 (3H, m), 3.98 (1H, m), 4.34 (1H, m), 4.46 (1H, m), 4.82 (1H, brd) |

TABLE 28

| Example No. | Condition | Chemical shift δ (ppm) |
|---|---|---|
| 91 | 500 MHz, CD$_3$OD | 0.89 (6H, t), 1.30 (20H, brs), 1.57 (4H, m), 3.48 (8H, m), 3.66 (2H, m), 3.91 (1H, m), 4.01 (3H, m), 4.16 (1H, m), 4.52 (1H, m), 4.63 (1H, m), 4.87 (1H, m) |
| 92 | 600 MHz, d$_6$-DMSO, 40° C. | 0.85 (6H, t), 1.24 (36H, brs), 1.48 (4H, m), 3.37 (8H, m), 3.56 (2H, m), 3.72 (1H, m), 3.86 (3H, m), 3.97 (1H, m), 4.33 (1H, m), 4.46 (1H, m), 4.81 (1H, brd) |
| 93 | 700 MHz, d$_6$-DMSO, 40° C. | 0.85 (6H, t), 1.23 (44H, brs), 1.48 (4H, m), 3.37 (8H, m), 3.56 (2H, m), 3.72 (1H, m), 3.85 (3H, m), 3.95 (1H, m), 4.33 (1H, m), 4.46 (1H, m), 4.81 (1H, m) |
| 94 | 500 MHz, CD$_3$OD | 0.92 (3H, t), 0.93 (3H, t), 1.37 (4H, m), 1.46 (4H, m), 1.56 (2H, m), 3.49 (4H, m), 3.66 (2H, m), 3.81 (1H, m), 3.88 (2H, m), 4.03 (2H, m), 4.52 (1H, m), 4.63 (1H, m), 4.87 (1H, m) |
| 95 | 500 MHz, CD$_3$OD | 0.91 (6H, m), 1.31 (16H, m), 1.48 (4H, m), 3.65 (2H, m), 3.86 (1H, m), 3.91 (2H, m), 4.00 (1H, m), 4.16 (1H, m), 4.39 (1H, m), 4.57 (1H, m), 4.87 (1H, brs) |
| 96 | 700 MHz, CD$_3$OD | 1.38 (3H, m), 3.56 (1H, m), 3.61 (1H, m), 3.64 (2H, m), 3.86 (2H, m), 3.96 (1H, m), 4.11 (1H, m), 4.83 (1H, d) |
| 97 | 600 MHz, CD$_3$OD | 0.92 (3H, t), 1.38 (6H, m), 1.55 (2H, m), 3.48 (4H, m), 3.64 (2H, m), 3.86 (1H, m), 3.97 (2H, m), 4.11 (1H, m), 4.58 (2H, m), 4.82 (1H, d) |
| 98 | 500 MHz, CD$_3$OD | 0.90 (3H, m), 1.31 (12H, brs), 1.38 (3H, t), 1.45 (2H,, m) 3.64 (2H, m), 3.80 (1H, m), 3.85 (2H, m), 4.01 (1H, m), 4.59 (2H, m), 4.82 (1H, d) |

The results of measurement of $^{13}$C-NMR of the products obtained in Examples 30 to 98 are shown in Tables 29-37.

TABLE 29

| Example No. | Condition | Chemical shift δ (ppm) |
|---|---|---|
| 30 | 125 MHz, CD$_3$OD | 59.5, 63.36, 63.40, 70.1, 70.2, 70.5, 70.6, 73.7, 73.8, 74.46, 74.50, 76.8, 121.1, 121.2, 151.67, 151.72, 172.88, 172.9 |
| 31 | 150 MHz, CD$_3$OD | 10.8, 23.8, 63.38, 63.41, 70.2, 70.4, 70.57, 70.63, 72.5, 72.6, 73.8, 73.9, 74.3, 76.8, 121.1, 121.2, 151.76, 151.80, 172.9, 173.0 |
| 32 | 125 MHz, CD$_3$OD | 63.3, 63.4, 70.2, 70.4, 70.5, 70.6, 71.88, 71.94, 73.7, 73.8, 73.3, 117.3, 121.05, 121.15, 136.0, 151.68, 151.73, 172.89, 172.93 |
| 33 | 125 MHz, CD$_3$OD | 17.9, 63.36, 63.38, 70.2, 70.3, 70.5, 70.6, 71.4, 71.5, 73.0, 73.75, 73.84, 121.05, 121.14, 128.7, 130.5, 151.7, 151.8, 172.89, 172.93 |
| 34 | 125 MHz, CD$_3$OD | 35.1, 63.3, 63.4, 70.2, 70.3, 70.5, 70.6, 72.0, 72.47, 72.53, 73.7, 73.8, 116.8, 121.03, 121.12, 136.4, 151.7, 151.8, 172.88, 172.99 |
| 35 | 150 MHz, CD$_3$OD | 14.4, 23.6, 29.4, 30.3, 63.37, 63.40, 70.2, 70.4, 70.57, 70.62, 72.5, 72.6, 72.7, 73.8, 73.9, 76.8, 121.1, 121.2, 151.76, 151.79, 172.9, 173.0 |
| 36 | 150 MHz, CD$_3$OD | 14.4, 23.7, 26.9, 30.7, 32.9, 63.37, 63.40, 70.3, 70.4, 70.57, 70.63, 72.5, 72.6, 72.7, 73.8, 73.9, 76.8, 121.13, 121.21, 151.7, 151.8, 172.9, 173.0 |
| 37 | 150 MHz, CD$_3$OD | 14.4, 23.7, 27.1, 30.2, 30.7, 33.0, 63.3, 63.4, 70.2, 70.3, 70.5, 70.6, 72.4, 72.5, 72.7, 73.8, 73.9, 76.8, 121.05, 121.12, 151.7, 151.8, 172.88, 172.92 |
| 38 | 125 MHz, CD$_3$OD | 14.4, 23.7, 27.2, 30.74, 30.5, 30.60, 30.69, 30.74, 33.1, 63.36, 63.38, 70.2, 70.4, 70.5, 70.6, 72.5, 72.6, 72.7, 73.8, 73.9, 76.8, 121.1, 121.2, 151.7, 151.8, 172.89, 172.93 |
| 39 | 150 MHz, CD$_3$OD | 14.4, 23.7, 27.2, 30.8, 33.0, 30.5, 30.60, 30.69, 30.74, 30.8, 33.1, 63.37, 63.41, 70.2, 70.4, 70.58, 70.64, 72.5, 72.6, 72.7, 73.8, 73.9, 76.8, 121.10, 121.18, 151.7, 151.8, 172.91, 172.95 |

TABLE 30

| Example No. | Condition | Chemical shift δ (ppm) |
|---|---|---|
| 40 | 150 MHz, CD$_3$OD | 14.4, 23.7, 27.2, 30.5, 30.5, 30.6, 30.70, 30.75, 30.78, 33.1, 63.37, 63.40, 70.2, 70.4, 70.50, 70.63, 72.5, 72.6, 72.7, 73.8, 73.9, 76.8, 121.1, 121.2, 151.7, 151.8, 172.91, 172.95 |

TABLE 30-continued

| Example No. | Condition | Chemical shift δ (ppm) |
|---|---|---|
| 41 | 150 MHz, CD$_3$OD | 14.4, 23.7, 27.2, 33.1, 30.5, 30.6, 30.70, 30.75, 30.78, 63.37, 63.41, 70.2, 70.4, 70.58, 70.64, 72.5, 72.6, 72.7, 73.8, 73.9, 76.8, 121.10, 121.18, 151.7, 151.8, 172.91, 172.95 |
| 42 | 150 MHz, CD$_3$OD | 14.4, 23.7, 27.2, 30.7, 30.5, 30.6, 30.8, 33.1, 63.36, 63.40, 70.2, 70.4, 70.57, 70.62, 72.5, 72.6, 72.7, 73.8, 73.9, 76.8, 121.1, 121.2, 151.7, 151.8, 172.9, 173.0 |
| 43 | 125 MHz, CD$_3$OD | 22.1, 22.3, 63.36, 63.40, 69.9, 70.0, 70.5, 70.6, 70.61, 70.63, 73.59, 73.61, 73.8, 73.9, 76.8, 121.1, 121.2, 151.79, 151.84, 172.9, 173.0 |
| 44 | 125 MHz, CD$_3$OD | 63.37, 63.41, 69.76, 69.85, 69.84, 69.96, 70.56, 70.60, 73.46, 73.48, 76.79, 76.80, 115.6, 121.18, 121.27, 122.0, 130.5, 151.58, 151.63, 160.2, 172.85, 172.88 |
| 45 | 150 MHz, CD$_3$OD | 27.7, 63.37, 63.40, 63.6, 63.7, 70.58, 70.63, 70.8, 71.0, 73.9, 74.0, 74.4, 76.8, 121.05, 121.12, 151.9, 152.0, 172.98, 173.02 |
| 46 | 150 MHz, CD$_3$OD | 14.4, 23.7, 26.49, 26.55, 30.4, 30.7, 30.8, 33.0, 34.0, 34.1, 63.37, 63.41, 70.6, 70.7, 71.0, 71.2, 76.3, 76.4, 76.9, 120.9, 121.1, 151.8, 151.9, 172.98, 173.04 |
| 47 | 125 MHz, CD$_3$OD | 14.4, 23.7, 26.49, 26.55, 30.5, 30.6, 30.8, 33.1, 34.0, 34.1, 63.36, 63.39, 70.6, 70.7, 71.0, 71.2, 76.3, 76.4, 76.8, 120.9, 121.1, 151.8, 151.9, 172.98, 173.04 |
| 48 | 100 MHz, CD$_3$OD | 14.24, 20.25, 32.77, 63.29, 70.55, 70.61, 72.34, 72.64, 72.66, 75.01, 75.09, 77.10, 121.78, 121.82, 163.76, 163.84, 173.32, 173.34 |
| 49 | 100 MHz, CD$_3$OD | 14.32, 23.57, 28.72, 33.76, 63.38, 70.55, 71.43, 71.46, 76.92, 77.46, 77.58, 122.17, 122.24, 162.08, 162.14, 173.07, 173.13 |

TABLE 31

| Example No. | Condition | Chemical shift δ (ppm) |
|---|---|---|
| 50 | 175 MHz, CD$_3$OD | 14.40, 23.68, 26.54, 30.35, 30.62, 30.74, 33.01, 34.06, 63.46, 70.66, 71.45, 77.18, 77.56, 77.68, 121.95, 122.03, 163.26, 163.33, 173.42, 173.48 |
| 51 | 100 MHz, CD$_3$OD | 24.92, 25.12, 32.06, 32.10, 34.33, 34.38, 63.34, 63.40, 70.53, 70.57, 74.42, 74.47, 76.70, 76.77, 87.55, 87.82, 122.08, 161.97, 162.33, 173.40, 173.53 |
| 52 | 175 MHz, CD$_3$OD | 13.27, 17.91, 63.23, 63.55, 63.58, 70.55, 71.50, 71.58, 73.89, 74.09, 74.19, 76.81, 122.36, 122.40, 126.17, 127.27, 131.18, 133.28, 159.82, 159.85, 172.28 |
| 53 | 125 MHz, CD$_3$OD | 14.25, 17.96, 20.33, 32.84, 63.22, 69.99, 70.09, 70.50, 70.55, 72.42, 72.47, 72.53, 73.87, 74.58, 76.78, 76.79, 122.32, 122.36, 127.30, 133.18, 159.82, 159.86, 172.27 |
| 54 | 125 MHz, CD$_3$OD | 14.25, 20.29, 32.78, 33.08, 63.21, 69.92, 70.01, 70.53, 70.57, 72.40, 72.46, 74.64, 74.66, 75.25, 75.27, 76.79, 76.81, 122.26, 122.29, 129.59, 130.04, 137.63, 159.87, 159.93, 172.14 |
| 55 | 100 MHz, CD$_3$OD | 63.22, 69.57, 69.68, 69.67, 69.75, 70.52, 70.55, 74.12, 74.16, 74.23, 76.76, 115.64, 119.39, 122.12, 122.61, 122.65, 130.51, 134.45, 159.52, 160.13, 160.15, 171.98 |
| 56 | 100 MHz, CD$_3$OD | 63.24, 69.49, 69.56, 69.70, 69.77, 70.56, 70.59, 74.30, 74.37, 75.29, 76.81, 115.64, 112.10, 122.35, 122.38, 129.61, 129.99, 137.54, 159.73, 160.08, 160.10, 172.06 |
| 57 | 125 MHz, CD$_3$OD | 14.1, 20.1, 32.9, 63.2, 63.56, 63.59, 70.5, 70.6, 71.5, 71.6, 73.69, 73.72, 74.0, 74.1, 76.7, 123.28, 123.30, 159.23, 159.25, 172.2 |
| 58 | 125 MHz, CD$_3$OD | 14.4, 23.6, 26.6, 30.7, 63.2, 63.49, 63.51, 70.46, 70.49, 71.45, 71.54, 73.95, 73.97, 74.00, 74.06, 76.7, 123.00, 123.22, 159.19, 159.21, 172.2 |
| 59 | 150 MHz, CD$_3$OD | 14.4, 23.6, 26.9, 30.1, 30.8, 32.9, 63.2, 63.5, 63.6, 70.50, 70.54, 71.5, 71.6, 74.00, 74.03, 74.10, 76.7, 123.2, 123.3, 159.22, 159.24, 172.2 |

TABLE 32

| Example No. | Condition | Chemical shift δ (ppm) |
|---|---|---|
| 60 | 150 MHz, CD$_3$OD | 14.4, 23.7, 27.0, 30.5, 30.7, 30.4, 30.8, 33.0, 63.2, 63.56, 63.60, 70.5, 70.6, 71.56, 71.63, 74.03, 74.05, 74.13, 76.7, 123.28, 123.31, 159.25, 159.28, 172.3 |

TABLE 32-continued

| Example No. | Condition | Chemical shift δ (ppm) |
|---|---|---|
| 61 | 150 MHz, CD$_3$OD | 14.4, 23.7, 26.9, 30.48, 30.44, 30.48, 30.7, 30.8, 33.1, 63.2, 63.5, 63.6, 70.5, 70.6, 71.5, 71.6, 74.02, 74.05, 74.11, 76.7, 123.26, 123.29, 159.24, 159.27, 172.2 |
| 62 | 150 MHz, CD$_3$OD | 14.4, 23.7, 26.9, 30.70, 30.47, 30.49, 30.70, 30.74, 30.8, 33.1, 63.2, 63.5, 63.6, 70.5, 70.6, 71.5, 71.6, 74.02, 74.05, 74.11, 76.7, 123.27, 123.29, 159.2, 159.3, 172.4 |
| 63 | 125 MHz, CD$_3$OD | 14.4, 23.7, 27.0, 30.5, 30.76, 30.72, 30.76, 30.79, 30.81, 33.1, 63.2, 63.56, 63.58, 70.5, 70.6, 71.5, 71.6, 74.0, 74.1, 76.7, 123.27, 123.29, 159.2, 159.3, 172.2 |
| 64 | 125 MHz, CD$_3$OD | 14.4, 23.7, 27.0, 30.81, 30.48, 30.50, 30.71, 30.78, 30.81, 33.1, 63.2, 63.56, 63.58, 70.5, 70.6, 71.5, 71.6, 74.0, 74.1, 76.7, 123.27, 123.29, 159.2, 159.3, 172.2 |
| 65 | 125 MHz, CD$_3$OD | 14.4, 23.7, 27.0, 30.80, 30.48, 30.51, 30.72, 30.76, 30.80, 33.1, 63.2, 63.56, 63.59, 70.5, 70.6, 71.5, 71.6, 74.0, 74.1, 76.7, 123.27, 123.30, 159.23, 159.25, 172.2 |
| 66 | 175 MHz, CD$_3$OD | 14.39, 15.48, 15.54, 63.16, 63.24, 67.95, 68.02, 69.56, 70.00, 70.08, 70.52, 70.56, 72.26, 74.38, 76.74, 122.91, 122.95, 159.51, 159.54, 172.27 |
| 67 | 125 MHz, CD$_3$OD | 14.38, 15.34, 15.43, 23.64, 26.63, 30.75, 32.71, 63.21, 67.95, 70.00, 70.09, 70.50, 70.56, 72.29, 73.98, 74.00, 74.50, 76.66, 76.69, 123.23, 123.26, 159.22, 159.25, 172.21 |
| 68 | 125 MHz, CD$_3$OD | 14.23, 15.51, 20.32, 32.82, 63.21, 69.55, 70.00, 70.10, 70.50, 70.55, 72.40, 72.47, 72.52, 74.45, 74.47, 76.72, 122.88, 122.92, 159.52, 159.57, 172.27 |

TABLE 33

| Example No. | Condition | Chemical shift δ (ppm) |
|---|---|---|
| 69 | 125 MHz, CD$_3$OD | 14.26, 14.38, 20.27, 20.34, 23.65, 26.63, 30.77, 32.73, 32.86, 63.22, 70.01, 70.12, 70.51, 70.56, 72.45, 72.50, 72.55, 73.98, 74.01, 74.57, 74.59, 76.67, 76.70, 123.23, 123.26, 159.23, 159.28, 172.21 |
| 70 | 150 MHz, CD$_3$OD | 14.27, 14.44, 20.35, 23.72, 26.99, 30.40, 30.48, 30.83, 32.88, 33.01, 63.23, 70.04, 70.14, 70.52, 70.58, 72.46, 72.53, 72.55, 72.57, 73.99, 74.01, 74.59, 74.62, 76.68, 76.71, 123.24, 123.27, 159.23, 159.28, 172.22 |
| 71 | 175 MHz, CD$_3$OD | 14.28, 14.42, 20.35, 23.73, 27.00, 30.47, 30.51, 30.74, 30.78, 30.83, 32.88, 33.06, 63.24, 70.05, 70.15, 70.53, 70.59, 72.48, 72.54, 72.60, 74.01, 74.02, 74.62, 74.64, 76.70, 76.73, 123.26, 123.29, 159.25, 159.30, 172.23 |
| 72 | 150 MHz, CD$_3$OD | 14.30, 14.44, 20.37, 23.73, 27.01, 30.47, 30.53, 30.73, 30.76, 30.79, 30.84, 32.90, 33.08, 63.21, 70.05, 70.15, 70.53, 70.59, 72.48, 72.54, 72.59, 74.00, 74.02, 74.62, 74.65, 76.69, 76.73, 123.25, 123.28, 159.24, 159.30, 172.24 |
| 73 | 150 MHz, CD$_3$OD | 14.44, 23.69, 23.72, 27.00, 27.16, 27.27, 30.41, 30.44, 30.50, 30.61, 30.76, 30.84, 33.02, 63.21, 69.99, 70.10, 70.56, 70.64, 72.48, 72.76, 73.97, 74.00, 74.56, 74.60, 76.67, 76.70, 123.25, 123.23, 159.21, 159.25, 172.17 |
| 74 | 150 MHz, d$_6$-DMSO, 40° C. | 13.95, 22.13, 25.40, 25.42, 25.63, 25.71, 28.74, 28.78, 28.87, 28.97, 29.09, 29.20, 29.28, 29.30, 31.34, 61.72, 68.04, 68.09, 68.81, 70.88, 71.48, 71.52, 72.14, 73.24, 73.43, 74.55, 121.29, 157.71, 157.85, 169.42 |
| 75 | 150 MHz, d$_6$-DMSO, 40° C. | 13.94, 22.13, 25.40, 25.41, 25.70, 28.72, 28.75, 28.83, 28.99, 29.06, 29.08, 29.10, 29.21, 29.26, 29.28, 31.32, 31.35, 61.72, 68.03, 68.08, 68.81, 70.86, 72.14, 73.21, 73.39, 74.55, 74.57, 121.29, 157.74, 157.86, 169.42 |

TABLE 34

| Example No. | Condition | Chemical shift δ (ppm) |
|---|---|---|
| 76 | 125 MHz, d$_6$-DMSO, 40° C. | 13.95, 13.98, 22.14, 25.42, 25.45, 25.63, 25.73, 28.75, 28.78, 28.90, 29.03, 29.06, 29.11, 29.22, 29.29, 29.29, 29.31, 31.35, 61.72, 68.03, 68.09, 68.80, 70.92, 71.48, 71.52, 73.29, 73.48, 74.56, 74.58, 121.28, 157.72, 157.86, 169.41 |
| 77 | 150 MHz, d$_6$-DMSO, 40° C. | 13.95, 22.15, 25.43, 28.75, 28.86, 28.93, 29.01, 29.09, 29.23, 29.28, 31.36, 61.73, 68.05, 68.09, 68.82, 70.89, 71.47, 71.50, 73.25, 73.42, 74.57, 121.31, 157.75, 157.87, 169.44 |

TABLE 34-continued

| Example No. | Condition | Chemical shift δ (ppm) |
| --- | --- | --- |
| 78 | 125 MHz, d₆-DMSO, 40° C. | 13.95, 13.97, 22.15, 25.45, 25.47, 25.64, 25.74, 28.77, 28.92, 29.09, 29.12, 29.24, 29.30, 31.37, 61.72, 68.05, 68.79, 68.81, 70.91, 71.49, 71.52, 72.15, 73.48, 73.51, 74.57, 121.29, 157.71, 157.86, 169.42 |
| 79 | 150 MHz, CD₃OD | 14.15, 14.42, 20.13, 23.70, 26.43, 26.50, 30.38, 30.72, 30.74, 32.95, 33.03, 34.06, 34.10, 63.21, 63.23, 70.53, 70.62, 73.59, 76.70, 76.72, 76.90, 123.12, 123.18, 159.22, 172.22, 172.26 |
| 80 | 150 MHz, CD₃OD | 14.43, 23.69, 27.20, 30.42, 30.59, 30.67, 30.00, 63.17, 63.20, 63.95, 63.98, 70.01, 70.11, 70.20, 70.53, 70.56, 71.88, 71.93, 72.38, 72.43, 72.76, 72.43, 74.51, 74.57, 75.01, 75.07, 76.79, 76.81, 122.92, 122.98, 123.08, 159.45, 159.47, 172.26 |
| 81 | 150 MHz, CD₃OD | 14.43, 23.72, 27.21, 30.46, 30.58, 30.62, 30.69, 30.75, 30.78, 33.07, 63.19, 63.22, 63.97, 63.99, 70.04, 70.13, 70.21, 70.56, 71.91, 71.95, 72.40, 72.46, 72.77, 74.46, 74.53, 74.59, 75.03, 75.09, 76.81, 123.00, 159.46, 159.48, 172.27 |
| 82 | 150 MHz, CD₃OD | 14.44, 23.72, 27.22, 30.46, 30.63, 30.70, 30.75, 30.78, 33.07, 63.19, 63.22, 63.97, 63.99, 70.04, 70.13, 70.21, 70.23, 70.56, 70.59, 71.91, 71.95, 72.41, 72.46, 72.78, 74.46, 74.53, 74.60, 75.03, 75.09, 76.81, 122.95, 123.01, 123.10, 159.45, 172.27 |

TABLE 35

| Example No. | Condition | Chemical shift δ (ppm) |
| --- | --- | --- |
| 83 | 150 MHz, CD₃OD | 14.43, 23.71, 26.54, 30.35, 30.41, 30.55, 30.65, 30.73, 32.13, 32.22, 33.01, 33.97, 63.10, 63.20, 63.39, 63.97, 70.57, 70.61, 70.67, 70.69, 71.88, 71.96, 72.03, 75.02, 75.09, 77.04, 77.07, 76.83, 76.81, 122.78, 122.86, 122.90, 122.97, 159.61, 159.63, 159.65, 172.16, 172.36, 172.39 |
| 84 | 175 MHz, CD₃OD | 14.42, 23.71, 27.21, 30.41, 30.57, 30.73, 33.01, 63.22, 63.58, 63.62, 70.41, 70.45, 70.57, 70.60, 71.70, 72.72, 72.91, 74.25, 74.32, 75.33, 76.80, 122.96, 123.01, 123.04, 159.32, 159.37, 172.11 |
| 85 | 150 MHz, CD₃OD | 14.44, 23.73, 27.20, 30.47, 30.63, 30.74, 30.79, 33.07, 63.19, 63.21, 63.57, 63.60, 70.40, 70.44, 70.55, 70.59, 71.65, 71.69, 71.73, 72.72, 72.90, 74.23, 74.31, 75.29, 75.31, 75.38, 76.78, 76.80, 122.95, 122.99, 123.02, 159.31, 159.37, 172.10 |
| 86 | 125 MHz, CD₃OD | 14.44, 23.73, 27.20, 30.48, 30.64, 30.75, 30.78, 33.07, 63.17, 63.55, 63.58, 70.38, 70.41, 70.53, 70.57, 71.55, 71.64, 71.67, 71.71, 72.71, 72.89, 74.22, 74.30, 75.26, 75.31, 75.37, 76.77, 122.92, 122.97, 123.00, 159.32, 159.38, 172.12 |
| 87 | 175 MHz, CD₃OD | 14.25, 20.31, 32.82, 32.86, 63.20, 63.23, 70.13, 70.21, 70.24, 70.37, 70.41, 70.57, 70.59, 70.87, 72.39, 72.45, 72.47, 72.90, 74.57, 74.65, 74.77, 74.86, 75.25, 75.29, 75.36, 76.78, 76.86, 76.98, 122.93, 123.01, 123.04, 123.11, 159.33, 159.37, 159.56, 172.11 |
| 88 | 100 MHz, CD₃OD | 63.22, 63.23, 69.57, 69.67, 69.75, 69.89, 70.59, 74.28, 74.65, 76.80, 115.63, 115.70, 122.00, 122.08, 130.50, 159.39, 159.93, 159.97, 160.20 |

TABLE 36

| Example No. | Condition | Chemical shift δ (ppm) |
| --- | --- | --- |
| 89 | 125 MHz, CD₃OD | 14.28, 14.44, 20.33, 23.72, 27.22, 30.43, 30.60, 30.74, 32.83, 33.02, 63.17, 63.19, 70.01, 70.12, 70.19, 70.35, 70.38, 70.54, 70.57, 70.85, 72.45, 72.62, 72.70, 72.80, 74.57, 74.64, 74.69, 74.83, 75.26, 75.32, 76.78, 76.86, 76.98, 122.92, 122.98, 123.02, 123.08, 159.32, 159.37, 159.49, 159.54, 172.10 |
| 90 | 150 MHz, d₆-DMSO, 40° C. | 13.82, 13.99, 18.88, 22.16, 25.69, 28.77, 28.98, 29.08, 29.10, 29.28, 31.37, 61.69, 61.73, 68.14, 68.18, 68.22, 68.27, 68.32, 68.35, 68.86, 68.87, 73.21, 73.38, 73.91, 73.97, 74.65, 74.79, 121.42, 121.35, 121.29, 157.65, 157.70, 157.73, 157.91, 169.26, 169.33, 169.38, 169.43 |
| 91 | 125 MHz, CD₃OD | 14.46, 23.72, 27.22, 30.44, 30.46, 30.67, 30.72, 30.74, 33.02, 63.16, 63.18, 69.97, 70.08, 70.18, 70.19, 70.25, 70.33, 70.37, 70.53, 72.39, 72.45, 72.61, 72.70, 72.77, 72.87, 72.92, 74.56, 75.20, 75.24, 76.75, 122.91, 122.97, 123.07, 159.30, 159.34, 172.08 |
| 92 | 150 MHz, d₆-DMSO, 40° C. | 13.95, 22.16, 25.70, 25.72, 28.77, 28.94, 28.99, 29.01, 29.11, 29.27, 29.30, 31.37, 61.72, 68.11, 68.19, 68.27, 68.31, 68.86, 68.87, 70.81, 70.89, 71.38, 71.44, 71.84, 71.88, 73.23, 73.37, |

TABLE 36-continued

| Example No. | Condition | Chemical shift δ (ppm) |
|---|---|---|
| | | 73.40, 73.87, 73.94, 74.64, 121.29, 121.34, 121.43, 157.59, 157.67, 157.69, 169.40 |
| 93 | 175 MHz, $d_6$-DMSO, 40° C. | 13.94, 22.14, 28.76, 28.79, 29.00, 29.03, 29.07, 29.11, 29.13, 29.27, 29.30, 31.36, 31.36, 31.38, 61.69, 61.72, 68.11, 68.19, 68.31, 68.33, 68.86, 68.91, 70.81, 70.89, 71.37, 71.44, 71.84, 71.88, 73.25, 73.29, 73.39, 73.42, 73.85, 73.89, 73.92, 74.64, 121.30, 121.35, 121.44, 157.56, 157.60, 157.65, 157.67, 169.39 |
| 94 | 125 MHz, $CD_3OD$ | 14.27, 14.39, 20.28, 20.32, 23.77, 28.82, 32.82, 34.02, 34.05, 63.18, 70.13, 70.18, 70.23, 70.54, 70.57, 71.08, 71.14, 72.45, 74.55, 76.76, 77.68, 77.73, 77.86, 77.90, 122.99, 123.02, 122.92, 159.27, 159.33, 159.50, 172.21 |

TABLE 37

| Example No. | Condition | Chemical shift δ (ppm) |
|---|---|---|
| 95 | 125 MHz, $CD_3OD$ | 14.40, 14.44, 23.73, 23.79, 26.58, 28.84, 28.93, 30.38, 30.44, 30.68, 30.77, 33.06, 34.02, 34.14, 63.09, 63.18, 63.38, 70.11, 70.56, 70.61, 70.64, 70.90, 71.03, 71.07, 71.14, 71.23, 75.02, 75.09, 76.77, 76.81, 77.00, 77.06, 77.15, 77.24, 122.75, 122.85, 122.90, 122.89, 159.38, 159.40, 159.45, 172.27, 172.32, 172.55 |
| 96 | 175 MHz, $CD_3OD$ | 15.50, 63.28, 63.97, 64.00, 69.56, 69.63, 70.54, 71.93, 75.18, 75.22, 76.74, 122.59, 122.61, 159.71, 159.82, 172.40, 172.58 |
| 97 | 150 MHz, $CD_3OD$ | 14.25, 15.53, 20.29, 63.26, 63.23, 69.51, 69.59, 70.34, 70.53, 72.34, 72.79, 75.33, 75.40, 76.67, 76.69, 122.55, 122.58, 159.63, 169.65, 172.42 |
| 98 | 125 MHz, $CD_3OD$ | 14.47, 15.57, 23.69, 26.55, 30.38, 30.65, 30.75, 33.01, 34.34, 63.25, 69.47, 69.54, 70.51, 71.07, 77.78, 77.84, 77.95, 122.57, 122.61, 159.45, 159.48, 172.39 |

TEST EXAMPLE 1

As a test for a whitening effect, evaluation of the action of B16 melanoma 4A5 cell on theophylline-induced melanine production was carried out on an ascorbic acid derivative of the present invention, according to the following procedure. The same evaluation was carried out also on ascorbic acid, known compounds: ascorbic acid salts, and ascorbic acid derivatives, as comparison. The results are shown in Tables 38 to 40.

(1) B16 mouse melanoma 4A5 strain was sowed onto a 48-well plate at a cell density of $2.0 \times 10^4$ cells/well.
(2) Culturing was performed for 24 hours with Dulbecco's Modified Eagle's medium (manufactured by SIGMA. Hereinafter, abbreviated as D-MEM) containing 10% fetal bovine serum (manufactured by Roshe Diagnostics). Then, it was changed to 0.2 mM theophylline and a 10% fetal bovine serum-containing D-MEM which contains a sample of given concentration.
(3) After culturing for 3 days in the co-existence of a sample, the medium was removed using an aspirator. Then, after distilled water was added, cells were broken by an ultrasonic wave.
(4) Thereafter, the amount of protein was determined using BCA protein assay kit (manufactured by PIERCE), and the produced amount of melanine was measured by an alkali solubilizing method. To the cell-destructed solution was added sodium hydroxide so as to give a final concentration of 2N and the mixture was dissolved by heating (60° C., 15 minutes), then, the absorbance at 450 nm was measured using a micro plate reader. The melanine amount was calculated from a calibration curve made using synthetic melanine (SIGMA) as a standard. The melanine amount per unit protein was calculated by dividing the melanine amount by the protein amount.
(5) The melanine production suppressing rate was calculated according to the following formula.

Melanine production suppressing rate (%)=[1−(A−B)/(C−B)]×100

[wherein, A represents the melanine amount per unit protein (g/g) in adding a sample, B represents the melanine amount per unit protein (g/g) in the normal group, and C represents the melanine amount per unit protein (g/g) in the control group.]

In the following Tables, the melanine production suppressing rate in measuring a sample at a concentration of 100 μM or less is expressed as described below. The measurement was carried out at N=4.
<20%:±
20 to 40%:+
40 to 70%:++
70 to 100%:+++

TABLE 38

| Example No. | Ascorbic acid derivative or salt thereof | Whitening effect |
|---|---|---|
| Comparison | arbutin | ++ |
| Comparison | Ascorbic acid | ± |
| Comparison | Sodium ascorbate | ± |
| Comparison | Magnesium ascorbyl phosphate | ± |
| Comparison | Ascorbic acid glucoside | + |
| Comparison | 3-O-ethylascorbic acid | + |
| 1 | 3-O-glyceryl ascorbic acid | + |
| 3 | 2-O-glyceryl ascorbic acid | + |
| 4 | 2,3-di-O-glyceryl ascorbic acid | + |
| 30 | 3-O-methylglyceryl ascorbic acid | ++ |

TABLE 38-continued

| Example No. | Ascorbic acid derivative or salt thereof | Whitening effect |
|---|---|---|
| 7 | 3-O-ethylglyceryl ascorbic acid | + |
| 31 | 3-O-butylglyceryl ascorbic acid | + |
| 34 | 3-O-homoallylglyceryl ascorbic acid | + |
| 8 | 3-O-octylglyceryl ascorbic acid | + |
| 38 | 3-O-undecylglyceryl ascorbic acid | ++ |
| 39 | 3-O-dodecylglyceryl ascorbic acid | ++ |
| 41 | 3-O-tetradecylglyceryl ascorbic acid | + |
| 9 | 3-O-hexadecylglyceryl ascorbic acid | + |
| 46 | 3-O-(2-hydroxydecyl) ascorbic acid | ++ |
| 47 | 3-O-(2-hydroxyhexadecyl) ascorbic acid | + |
| 11 | 3-O-(2-hydroxycyclohexyl) ascorbic acid | + |
| 12 | 3-O-(2-hydroxy-2-phenylethyl) ascorbic acid | ++ |
| 57 | 3-O-glyceryl-2-O-butylascorbic acid | + |
| 58 | 3-O-glyceryl-2-O-hexylascorbic acid | ++ |
| 59 | 3-O-glyceryl-2-O-heptylascorbic acid | ++ |
| 14 | 3-O-glyceryl-2-O-octylascorbic acid | +++ |
| 60 | 3-O-glyceryl-2-O-nonylascorbic acid | +++ |

TABLE 39

| Example No. | Ascorbic acid derivative or salt thereof | Whitening effect |
|---|---|---|
| 61 | 3-O-glyceryl-2-O-decylascorbic acid | +++ |
| 62 | 3-O-glyceryl-2-O-undecylascorbic acid | ++ |
| 63 | 3-O-glyceryl-2-O-dodecylascorbic acid | ++ |
| 64 | 3-O-glyceryl-2-O-tridecylascorbic acid | ++ |
| 65 | 3-O-glyceryl-2-O-tetradecylascorbic acid | ++ |
| 15 | 3-O-glyceryl-2-O-hexadecylascorbic acid | ++ |
| 22 | 3-O-glyceryl-2-O-butylglyceryl ascorbic acid | + |
| 84 | 3-O-glyceryl-2-O-octylglyceryl ascorbic acid | + |
| 85 | 3-O-glyceryl-2-O-dodecylglyceryl ascorbic acid | ++ |
| 86 | 3-O-glyceryl-2-O-hexadecylglyceryl ascorbic acid | ++ |
| 29 | 3-O-glyceryl-2-O-(2-hydroxydecyl) ascorbic acid | + |
| 17 | 3-O-glyceryl-2-O-benzylascorbic acid | + |
| 66 | 3-O-ethylglyceryl-2-O-ethylascorbic acid | + |
| 68 | 3-O-butylglyceryl-2-O-ethylascorbic acid | + |
| 19 | 3-O-butylglyceryl-2-O-butylascorbic acid | +++ |
| 69 | 3-O-butylglyceryl-2-O-hexylascorbic acid | +++ |
| 70 | 3-O-butylglyceryl-2-O-octylascorbic acid | ++ |
| 71 | 3-O-butylglyceryl-2-O-dodecylascorbic acid | + |
| 72 | 3-O-butylglyceryl-2-O-hexadecylascorbic acid | ++ |
| 90 | 3-O-butylglyceryl-2-O-dodecylglyceryl ascorbic acid | + |
| 24 | 3-O-butylglyceryl-2-O-hexadecylglyceryl ascorbic acid | + |
| 53 | 3-O-butylglyceryl-2-O-crotylascorbic acid | + |
| 54 | 3-O-butylglyceryl-2-O-benzylascorbic acid | + |
| 73 | 3-O-octylglyceryl-2-O-octylascorbic acid | + |
| 20 | 3-O-octylglyceryl-2-O-hexadecylascorbic acid | ++ |
| 80 | 3-O-octylglyceryl-2-O-glycerylascorbic acid | + |
| 91 | 3-O-octylglyceryl-2-O-octylglycerylascorbic acid | + |

TABLE 40

| Example No. | Ascorbic acid derivative or salt thereof | Whitening effect |
|---|---|---|
| 92 | 3-O-octylglyceryl-2-O-hexadecylglycerylascorbic acid | ++ |
| 75 | 3-O-dodecylglyceryl-2-O-octylascorbic acid | ++ |
| 76 | 3-O-dodecylglyceryl-2-O-hexa decylascorbic acid | + |
| 81 | 3-O-dodecylglyceryl-2-O-glycerylascorbic acid | ++ |
| 26 | 3-O-dodecylglyceryl-2-O-octylglycerylascorbic acid | ++ |
| 82 | 3-O-hexa decylglyceryl-2-O-glycerylascorbic acid | ++ |
| 77 | 3-O-hexa decylglyceryl-2-O-octylascorbic acid | + |
| 55 | 3-O-phenylglyceryl-2-O-allylglycerylascorbic acid | + |
| 56 | 3-O-phenylglyceryl-2-O-benzylascorbic acid | +++ |
| 88 | 3-O-phenylglyceryl-2-O-phenylglycerylascorbic acid | ++ |
| 83 | 3-O-(2-hydroxydecyl)-2-O-glycerylascorbic acid | + |
| 79 | 3-O-(2-hydroxydecyl)-2-O-butylascorbic acid | +++ |
| 28 | 3-O-(2-hydroxydecyl)-2-O-butylglycerylascorbic acid | ++ |
| 95 | 3-O-(2-hydroxydecyl)-2-O-(2-hydroxyhexyl)ascorbic acid | +++ |
| 96 | 3-O-ethyl-2-O-glycerylascorbic acid | + |
| 97 | 3-O-ethyl2-O-butylglycerylascorbic acid | + |
| 98 | 3-O-ethyl-2-O-(2-hydroxydecyl) ascorbic acid | ++ |
| 13 | 2-O-ethylglycerylascorbic acid | + |
| 48 | 2-O-butylglycerylascorbic acid | +++ |
| 49 | 2-O-(2-hydroxyhexyl) ascorbic acid | + |

The results in Tables 38-40 show that the ascorbic acid derivative of the present invention has a whitening effect equivalent to or higher than the effect of known ascorbic acid derivatives or salts thereof, namely, sodium ascorbate, magnesium ascorbyl phosphate and 3-O-ethylascorbic acid. Among them, certain compounds show a whitening effect of ++ or +++, and these results indicate that the ascorbic acid derivatives or salts thereof represented by (A), (B), (C), (D) and (E) described above have a more excellent whitening effect.

TEST EXAMPLE 2

Stability Test 1

Aqueous solutions (2%) of various test samples were adjusted to pH7 with a dilute sodium hydroxide aqueous solution, and charged into 50 mL screw tubes, and the tubes were sealed and stored at room temperature for 4 weeks. Thereafter, HPLC measurement were performed (using liquid chromatography manufactured by Tosoh Corp.) and the residual rate was obtained based on the peak area. The residual rate, odor(odor change) and degree of coloration were evaluated based on the following methods and standards, and the results are shown in Table 41.
Residual Rate:
  ⊚: 90% or more
  ○: 80% or more and less than 90%
  Δ: 60% or more and less than 80%
  X: 20% or more and less than 60%
  XX: less than 20%
Odor(Odor Change):
  It was evaluated according to the following criterion by 10 panelists.
  3: almost no odor
  2: slight abnormal odor
  1: intense abnormal odor
  Based on the evaluation results, classification was conducted as shown below.
  ○: total point of 10 panelists is 25 or more
  Δ: total point of 10 panelists is 16 to 24
  X: total point of 10 panelists is 15 or less
Coloration
  It was evaluated according to the following criterion by 10 panelists.
  3: almost no change as compared with that immediately after preparation
  2: coloration is observed as compared with that immediately after preparation
  1: intense coloration is observed as compared with that immediately after preparation Based on the evaluation results, classification was conducted as shown below.

○: total point of 10 panelists is 25 or more
Δ: total point of 10 panelists is 16 to 24
X: total point of 10 panelists is 15 or less

TABLE 41

| | | Storage period | | |
|---|---|---|---|---|
| | | 0 | 2 weeks | 4 weeks |
| 3-O-glyceryl-2-O-octyl ascorbic acid (Example 14) | Residual rate | ⊚ | ⊚ | ⊚ |
| | Odor | ○ | ○ | ○ |
| | Coloration | ○ | ○ | ○ |
| 3-O-ethylglyceryl ascorbic acid (Example 7) | Residual rate | ⊚ | ⊚ | ○ |
| | Odor | ○ | ○ | ○ |
| | Coloration | ○ | ○ | ○ |
| 2-O-glyceryl ascorbic acid (Example 3) | Residual rate | ⊚ | ⊚ | ⊚ |
| | Odor | ○ | ○ | ○ |
| | Coloration | ○ | ○ | ○ |
| 3-O-glyceryl ascorbic acid (Example 1) | Residual rate | ⊚ | ○ | ○ |
| | Odor | ○ | ○ | ○ |
| | Coloration | ○ | ○ | ○ |
| 2,3-di-O-glyceryl ascorbic acid (Example 4) | Residual rate | ⊚ | ⊚ | ⊚ |
| | Odor | ○ | ○ | ○ |
| | Coloration | ○ | ○ | ○ |
| Ascorbic acid (Comparison) | Residual rate | ⊚ | ○ | X |
| | Odor | ○ | Δ | X |
| | Coloration | ○ | Δ | X |
| 3-O-ethylascorbic acid (Comparison) | Residual rate | ⊚ | ○ | ○ |
| | Odor | ○ | ○ | ○ |
| | Coloration | ○ | ○ | Δ |

TEST EXAMPLE 3

Stability Test 2

The same test as in Test Example 2 was carried out excepting that the sample was stored at 50° C. for 4 weeks instead of storing at room temperature for 4 weeks. The results are shown in Table 42.

TABLE 42

| | | Storage period | | |
|---|---|---|---|---|
| | | 0 | 2 weeks | 4 weeks |
| 3-O-glyceryl-2-O-octylascorbic acid (Example 14) | Residual rate | ⊚ | ⊚ | ⊚ |
| | Odor | ○ | ○ | ○ |
| | Coloration | ○ | ○ | ○ |
| 2-O-glyceryl ascorbic acid (Example 3) | Residual rate | ⊚ | ⊚ | ⊚ |
| | Odor | ○ | ○ | ○ |
| | Coloration | ○ | ○ | ○ |
| 2,3-di-O-glyceryl ascorbic acid (Example 4) | Residual rate | ⊚ | ⊚ | ⊚ |
| | Odor | ○ | ○ | ○ |
| | Coloration | ○ | ○ | ○ |
| Ascorbic acid (Comparison) | Residual rate | ○ | X | X |
| | Odor | ○ | Δ | X |
| | Coloration | ○ | Δ | X |
| 3-O-ethylascorbic acid (Comparison) | Residual rate | ○ | X | X |
| | Odor | ○ | Δ | Δ |
| | Coloration | ○ | Δ | Δ |

The results in Table 42 show that the ascorbic acid derivative of the present invention is more excellent in stability over time when stored at room temperature to 50° C. than known ascorbic acid derivatives or salts thereof, namely, ascorbic acid and 3-O-ethylascorbic acid, and scarcely manifests generation of odor, coloration and the like. That is, the results shown in Tables 38 to 42 indicate that the ascorbic acid derivative of the present invention has an excellent whitening effect originally owned by ascorbic acid, and additionally, manifests an improvement in stability over time which was a problem of conventional ascorbic acid derivatives, and is more suitable as a compounding material of a cosmetic.

TEST EXAMPLE 4

Moisturizing Test: Measurement of Moisturizing Effect by Water Retention Force

A sample shown later was dried, and the dried sample was spread in an amount of about 0.4 g (this weight is represented by $W_0$) on the bottom of a weighing bottle (diameter: 3.6 cm, height excluding lid: 1.8 cm) so as to give uniform thickness. The sample contained in the weighing bottle was allowed to stand still in a constant humidity and constant temperature vessel (ENVIROS KCL-1000, TOKYO RIKAKIKAI CO, LTD) under environments of 25° C. and 65% RH. The weight was measured periodically, waiting until sufficient moisture absorption to attain equilibrium of weight increase (about 48 hours). Thereafter, the sample was transferred to under environments of 25° C. and 20% RH (in sealed vessel containing a saturated $CH_3COOK$ aqueous solution filled in the bottom part). From the weight after 24 hours (this weight is represented by $W_1$), the amount of retained water per 1 g of the dried sample was calculated according to the following formula.

$$(W_1-W_0)/W_0$$

From the water amount thus calculated, the moisturizing effect was judged based on the following judging criterion, and the results are shown in Table 43.

(Sample)
Three compounds: 2,3-di-O-glyceryl ascorbic acid, 2,3-di-O-phenylglyceryl ascorbic acid, and glycerin, and
Six compounds: ascorbic acid, ascorbic acid glucoside, 2-O-glyceryl ascorbic acid, 3-O-glyceryl ascorbic acid, 3-O-butylglyceryl ascorbic acid and 3-O-octylglyceryl ascorbic acid, which were adjusted to pH7 with a dilute sodium hydroxide aqueous solution and concentrated.

(Judging Criterion)
⊚: 40 mg or more
○: 25 mg or more and less than 40 mg
Δ: 10 mg or more and less than 25 mg
X: less than 10 mg

TABLE 43

| | Judgement |
|---|---|
| 2,3-di-O-glycerylascorbic acid | ⊚ |
| Ascorbic acid | X |
| 2-O-glycerylascorbic acid | ⊚ |
| ascorbic acid glucoside | ⊚ |
| Glycerin | ⊚ |
| 3-O-glycerylascorbic acid | ○ |
| 2,3-di-O-phenylglycerylascorbic acid | Δ |
| 3-O-butylglycerylascorbic acid | ○ |
| 3-O-octylglycerylascorbic acid | Δ |

It is apparent from the results in Table 43 that 2-O-glyceryl ascorbic acid and 2,3-di-O-glyceryl ascorbic acid have excellent moisturizing effect by far than ascorbic acid, and have a moisturizing effect approximately equivalent to glycerin and the like which are widely known as materials showing a high moisturizing property. It is also indicated from the results in Table 43 that also 3-O-glyceryl ascorbic acid and 3-O-butylglyceryl ascorbic acid show a more excellent moisturizing effect than ascorbic acid. Based on the results in Table 43, it is believed that ascorbic acid derivatives or salts thereof of the present invention in which $R^1$ represents $R^3$—O—$CH_2$—CH(OH)—$CH_2$— or $R^4$—O—$CH_2$—CH($CH_2OH$)—, and $R^2$, $R^3$ and $R^4$ represent H or alkyl, and the total carbon number of $R^2$, $R^3$ and $R^4$ is 4 or less in the formula (I), those in which $R^2$ represents $R^7$—O—$CH_2$—CH(OH)—$CH_2$— or $R^8$—O—$CH_2$—CH($CH_2OH$)—, and $R^1$, $R^7$ and $R^8$ represent H or alkyl, and the total carbon number of $R^1$, $R^7$ and $R^8$ is 4 or less in the formula (I), and those in which $R^1$ represents $R^3$—O—$CH_2$—CH(OH)—$CH_2$— or $R^4$—O—$CH_2$—CH($CH_2OH$)—, $R^2$ represents $R^7$—O—$CH_2$—CH(OH)—$CH_2$— or $R^8$—O—$CH_2$—CH($CH_2OH$)—, and $R^3$, $R^4$, $R^7$ and $R^8$ represent H or alkyl, and the total carbon number of $R^3$, $R^4$, $R^7$ and $R^8$ is 4 or less in the formula (I), are preferable from the standpoint of a moisturizing effect.

Further, it is predicted that also ascorbic acid derivatives obtained by substituting alkyl in $R^1$, $R^2$, $R^3$, $R^4$, $R^7$ or $R^8$ in these ascorbic acid derivatives by alkenyl, those obtained by substituting $R^3$—O—$CH_2$—CH(OH)—$CH_2$— or $R^4$—O—$CH_2$—CH($CH_2OH$)— by $R^5$—CH($CH_2OH$)— or $R^6$—CH(OH)—$CH_2$—, and/or, those obtained by substituting $R^7$—O—$CH_2$—CH(OH)—$CH_2$— or $R^8$—O—$CH_2$—CH($CH_2OH$)— by $R^9$—CH($CH_2OH$)— or $R^{10}$—CH(OH)—$CH_2$—, have a preferable moisturizing effect.

TEST EXAMPLE 5

Effect on Collagen Production of Human Fibroblast Exerted by Ascorbic Acid Derivative Normal human dermal fibroblasts were regulated with a 10% (v/v) fetal bovine serum (manufactured by Roshe Diagnostics)-containing D-MEM so as to give a cell density of $2.5 \times 10^4$ cells/well, then, pre-incubation for 24 hours was performed on a 96-well plate. After the medium was removed, a sample regulated with a 5% (v/v) fetal bovine serum-containing D-MEM to a concentration of 100 μM was added to each well, then, cultured for 48 hours under 37° C. and 5% $CO_2$. After completion of culturing, the amount of free collagen was measured using Sircol collagen assay kit (manufactured by Biocolor). The measurement was carried out at N=4.

The collagen production amount in measuring a sample at a concentration of 100 μM was compared with the control group, and the results thereof (% value when the control group is 100%) are shown in Tables 44 and 45 based on the following standard.

<100%:±
100 to 200%:+
200%<:++

TABLE 44

| Example No. | Ascorbic acid derivative or salt thereof | Collagen production promoting effect |
|---|---|---|
| Comparison | Ascorbic acid | + |
| Comparison | Magnesium ascorbyl phosphate | + |
| Comparison | Ascorbic acid glucoside | + |
| Comparison | 3-O-ethylascorbic acid | + |
| 1 | 3-O-glycerylascorbic acid | + |
| 3 | 2-O-glycerylascorbic acid | + |
| 4 | 2,3-di-O-glycerylascorbic acid | + |

TABLE 44-continued

| Example No. | Ascorbic acid derivative or salt thereof | Collagen production promoting effect |
|---|---|---|
| 6 | 3-O-butylglycerylascorbic acid | + |
| 33 | 3-O-crotylglycerylascorbic acid | + |
| 8 | 3-O-octylglycerylascorbic acid | + |
| 39 | 3-O-dodecylglycerylascorbic acid | + |
| 9 | 3-O-hexadecylglycerylascorbic acid | + |
| 45 | 3-O-tertiarybutylglycerylascorbic acid | + |
| 44 | 3-O-phenylglycerylascorbic acid | + |
| 46 | 3-O-(2-hydroxydecyl) ascorbic acid | + |
| 11 | 3-O-(2-hydroxycyclohexyl) ascorbic acid | + |
| 57 | 3-O-glyceryl-2-O-butylascorbic acid | + |
| 14 | 3-O-glyceryl-2-O-octylascorbic acid | + |
| 29 | 3-O-glyceryl-2-O-(2-hydroxydecyl) ascorbic acid | + |

TABLE 45

| Example No. | Ascorbic acid derivative or salt thereof | Collagen production promoting effect |
|---|---|---|
| 84 | 3-O-glyceryl-2-O-octylglycerylascorbic acid | + |
| 17 | 3-O-glyceryl-2-O-benzylascorbic acid | + |
| 66 | 3-O-ethylglyceryl-2-O-ethylascorbic acid | + |
| 18 | 3-O-ethylglyceryl-2-O-butylascorbic acid | + |
| 90 | 3-O-butylglyceryl-2-O-dodecylglyceryl ascorbic acid | + |
| 94 | 3-O-butylglyceryl-2-O-(2-hydroxyhexyl) ascorbic acid | + |
| 92 | 3-O-octylglyceryl-2-O-hexadecylglyceryl ascorbic acid | + |
| 88 | 3-O-phenylglyceryl-2-O-phenylglyceryl ascorbic acid | + |
| 83 | 3-O-(2-hydroxydecyl)-2-O-glyceryl ascorbic acid | + |
| 28 | 3-O-(2-hydroxydecyl)-2-O-butylglyceryl ascorbic acid | + |
| 97 | 3-O-ethyl-2-O-butylglycerylascorbic acid | + |
| 48 | 2-O-butylglycerylascorbic acid | + |
| 49 | 2-O-(2-hydroxyhexyl)ascorbic acid | + |

It is apparent from the results in Tables 44 and 45 that the ascorbic acid derivative of the present invention has a collagen production promoting effect which is approximately equivalent to free ascorbic acid and known ascorbic acid derivatives such as magnesium ascorbyl phosphate, ascorbic acid glucoside and 3-O-ethylascorbic acid.

TEST EXAMPLE 6

Effect on Collagen Production of Human Fibroblast Exerted by Ascorbic Acid Derivative 2

Free collagen was measured under the same conditions as in Test Example 5 excepting that the concentration of each sample was 100 μM or 500 μM and culturing was carried out for 2 days, 4 days and 7 days. The measurement was carried out at N=4, and the average and standard error, in four test examples, of values of the collagen production amount in comparison with the control group (% value when the control group is 100%) are shown in Tables 46 and 47.

TABLE 46

| Example No. | Ascorbic acid derivative | Culturing period | | |
|---|---|---|---|---|
| | | 2 days | 4 days | 7 days |
| 1 | 3-O-glycerylascorbic acid | 182 ± 7 | 209 ± 8 | 219 ± 29 |
| 3 | 2-O-glycerylascorbic acid | 226 ± 10 | 193 ± 6 | 258 ± 22 |
| 4 | 2,3-di-O-glycerylascorbic acid | 161 ± 8 | 171 ± 7 | 209 ± 27 |
| Comparison | Ascorbic acid | 252 ± 12 | 182 ± 9 | 139 ± 14 |
| Comparison | Magnesium ascorbyl phosphate | 276 ± 9 | 207 ± 24 | 191 ± 2 |
| Comparison | Ascorbic acid glucoside | 193 ± 4 | 239 ± 2 | 179 ± 14 |
| Comparison | 3-O-ethylascorbic acid | 140 ± 4 | 138 ± 2 | 106 ± 14 |

TABLE 47

| Example No. | Ascorbic acid derivative | Culturing period | | |
|---|---|---|---|---|
| | | 2 days | 4 days | 7 days |
| 39 | 3-O-dodecylglycerylascorbic acid | 82 ± 2 | 115 ± 5 | 186 ± 17 |
| 33 | 3-O-crotylglycerylascorbic acid | 79 ± 3 | 107 ± 8 | 160 ± 20 |
| 46 | 3-O-(2-hydroxydecyl) ascorbic acid | 152 ± 6 | 123 ± 11 | 254 ± 10 |
| 14 | 3-O-glyceryl-2-O-octylascorbic acid | 132 ± 22 | 144 ± 9 | 238 ± 17 |
| 84 | 3-O-glyceryl-2-O-octylglyceryl ascorbic acid | 135 ± 11 | 154 ± 8 | 201 ± 16 |
| 29 | 3-O-glyceryl-2-O-(2-hydroxydecyl)ascorbic acid | 97 ± 19 | 116 ± 7 | 138 ± 3 |
| 94 | 3-O-butylglyceryl-2-O-(2-O-hydroxyhexyl) ascorbic acid | 139 ± 19 | 152 ± 7 | 205 ± 36 |
| 81 | 3-O-dodecylglyceryl-2-O-glyceryl ascorbic acid | 115 ± 28 | 122 ± 18 | 149 ± 19 |
| 97 | 3-O-etyl-2-O-butylglyceryl ascorbic acid | 93 ± 4 | 111 ± 4 | 139 ± 15 |

As shown in Tables 46 and 47, the collagen production promoting effect of ascorbic acid and known compounds such as magnesium ascorbyl phosphate, ascorbic acid glucoside and 3-O-ethylascorbic acid lowers over time (7 days), while the collagen production promoting effect of the ascorbic acid derivative of the present invention increases over time, as shown in Tables 46 and 47. Therefore, it is apparent from the results in Tables 44 to 47 that the ascorbic acid derivative of the present invention has a collagen production promoting effect which is equivalent to or more excellent as compared with ascorbic acid and known ascorbic acid derivatives or salts thereof, that is, magnesium ascorbyl phosphate, 3-O-ethylascorbic acid and ascorbic acid glucoside, and additionally, is more excellent than these known ascorbic acids from the standpoint of durability of the collagen production promoting effect.

EXAMPLE 99

Cream

Oil phase part raw materials (1) to (5) and aqueous phase part raw materials (6) to (10) having compositions shown in Table 48 were heated up to 70° C. and dissolved, to prepare an oil phase and an aqueous phase, respectively. Thereafter, the oil phase was added to the aqueous phase. The mixture is pre-emulsified, and emulsified uniformly by a homo-mixer, then, cooled down to room temperature while stirring thoroughly, to prepare a cream excellent in whitening effect. In tables of Table 48 or later, the compounding amount shows part by weight.

TABLE 48

| No | Name of component | Compounding amount |
|---|---|---|
| 1 | Squalane | 9.0 |
| 2 | Vaseline | 6.0 |
| 3 | Steary alcohol | 5.0 |
| 4 | Polyoxyethylene(25) cetyl ether | 2.5 |
| 5 | Glyceryl monostearate | 1.5 |
| 6 | 3-O-butylglyceryl ascorbic acid (obtained in Example 6) | 2.0 |
| 7 | Glycerin | 6.0 |
| 8 | Antiseptic | proper amount |
| 9 | pH regulator | proper amount |
| 10 | Purified water | Residual amount* |

*Indicates an amount necessary for rendering the compounding amount to 100 parts by weight

EXAMPLE 100

Milky Lotion

Oil phase part raw materials (1) to (9) and aqueous phase part raw materials (10) to (13) having compositions shown in Table 49 were heated up to 70° C. and dissolved, to prepare an oil phase and an aqueous phase, respectively. Thereafter, the oil phase was added to the aqueous phase. The mixture is pre-emulsified, and emulsified uniformly by a homo-mixer, then, cooled down to room temperature while stirring thoroughly, to prepare a milky lotion excellent in whitening effect.

TABLE 49

| No | Name of component | Compounding amount |
|---|---|---|
| 1 | Isosteary palmitate | 5.0 |
| 2 | Jojoba oil | 2.0 |
| 3 | Dimethylpolysiloxane | 2.0 |
| 4 | Cetanol | 1.0 |
| 5 | Stearic acid | 1.5 |
| 6 | Bees wax | 2.5 |
| 7 | Paraffin wax | 2.5 |
| 8 | Polyoxyethylene(20) sorbitan monostearate | 1.2 |
| 9 | Polyoxyethylene(40) sorbitol tetraoleate | 1.5 |
| 10 | Propylene glycol | 10.0 |
| 11 | 3-O-glyceryl-2-O-hexylascorbic acid (Example 33) | 3.0 |
| 12 | Antiseptic | proper amount |
| 13 | Purified water | Residual amount* |

EXAMPLE 101

Milky Lotion

Oil phase part raw materials (5) to (10) and aqueous phase part raw materials (1) to (4) and (11) to (12) having compositions shown in Table 50 were heated up to 70° C. and dissolved, to prepare an oil phase and an aqueous phase, respectively. Thereafter, the oil phase was added to the aqueous phase. The mixture is pre-emulsified, and emulsified uniformly by a homo-mixer, then, cooled down to room temperature while stirring thoroughly, to prepare a milky lotion excellent in whitening effect.

TABLE 50

| No | Name of component | Compounding amount |
|---|---|---|
| 1 | Dipropylene glycol | 5.0 |
| 2 | 3-O-glyceryl-2-O-octylascorbic acid (Example 8) | 1.0 |
| 3 | Sorbitansesqui oleate | 4.0 |
| 4 | Polyoxyethylene(20) sorbitan monooleate | 1.0 |
| 5 | Micro crystalline wax | 1.0 |
| 6 | Bees wax | 2.0 |
| 7 | Lanolin | 2.0 |
| 8 | Liquid paraffin | 18.0 |
| 9 | Squalane | 12.0 |
| 10 | Perfume | proper amount |
| 11 | Antiseptic | proper amount |
| 12 | Purified water | Residual amount* |

EXAMPLE 102

Cream

Oil phase part raw materials (1) to (2) and aqueous phase part raw materials (3) to (10) having compositions shown in Table 51 were heated up to 70° C. and dissolved, to prepare an oil phase and an aqueous phase, respectively. Thereafter, the oil phase was added to the aqueous phase. The mixture is pre-emulsified, and emulsified uniformly by a homo-mixer, then, cooled down to room temperature while stirring thoroughly, to prepare a cream. This cream can be used as a cosmetic for skin having excellent whitening effect.

TABLE 51

| No | Name of component | Compounding amount |
|---|---|---|
| 1 | Liquid paraffin | 15.0 |
| 2 | Vaseline | 15.0 |
| 3 | Carboxyvinylpolymer | 0.1 |
| 4 | Xanthan gum | 0.1 |
| 5 | Hardened castor oil polyoxyethylene(40) derivative | 3.0 |
| 6 | 3-O-glyceryl-2-O-decyl ascorbic acid (Example 36) | 5.0 |
| 7 | Sodium hydroxide | 0.05 |
| 8 | Perfume | proper amount |
| 9 | Antiseptic | proper amount |
| 10 | Purified water | Residual amount* |

EXAMPLE 103

Lotion

A lotion can be prepared by mixing raw materials (1) to (6) having compositions shown in Table 52 while stirring thoroughly. Since this lotion contains 7% by weight of 2,3-di-O-glyceryl ascorbic acid, it has excellent moisturizing effect.

TABLE 52

| No | Name of component | Compounding amount |
|---|---|---|
| 1 | 2,3-Di-O-glyceryl ascorbic acid | 7.0 |
| 2 | Alcohol | 8.0 |
| 3 | Citric acid | 0.01 |
| 4 | Sodium citrate | 0.015 |
| 5 | Potassium glycyrrhizinate | 0.03 |
| 6 | Purified water | Residual amount* |

EXAMPLE 104

Cream

Oil phase part raw materials (1) to (6) and aqueous phase part raw materials (7) to (10) having compositions shown in Table 53 are heated up to 70° C. and dissolved, to prepare an oil phase and an aqueous phase, respectively. Thereafter, the oil phase is added to the aqueous phase. The mixture is pre-emulsified, and emulsified uniformly by a homo-mixer, then, cooled down to room temperature while stirring thoroughly, to prepare a cream. Since this cream contains 3% by weight of 3-O-glyceryl-2-O-tetradecyl ascorbic acid, it has excellent collagen production promoting effect, and is particularly excellent in durability of the effect. Since 3-O-glyceryl-2-O-tetradecyl ascorbic acid gives excellent whitening effect, this cream can be used as a cosmetic for skin excellent in whitening effect.

TABLE 53

| No | Name of component | Compounding amount |
|---|---|---|
| 1 | Cetylalcohol | 2.0 |
| 2 | Steary alcohol | 3.0 |
| 3 | Squalane | 7.5 |
| 4 | Glyceryl tri-2-ethylhexanate | 7.5 |
| 5 | Methyl Polysiloxane | 5.5 |
| 6 | 3-O-glyceryl-2-O-tetradecyl ascorbic acid | 3.0 |

TABLE 53-continued

| No | Name of component | Compounding amount |
|---|---|---|
| 7 | 1,3-Butylene glycol | 5.0 |
| 8 | Hydroxyethyl cellulose | 0.2 |
| 9 | Antiseptic | proper amount |
| 10 | Purified water | Residual amount* |

What is claimed is:

1. An ascorbic acid derivative represented by the following general formula (I):

(Chemical formula 1)

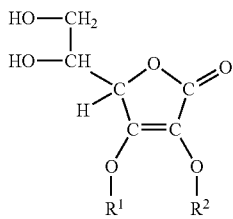

wherein,
R$^1$ represents H, alkyl group having 1 to 22 carbon atoms, alkenyl group having 2 to 22 carbon atoms, benzyl group, R$^3$—O—CH$_2$—CH(OH)—CH$_2$—, R$^4$—O—CH$_2$—CH(CH$_2$OH)—, R$^5$—CH(CH$_2$OH)—, R$^6$—CH(OH)—CH$_2$— or hydroxycyclohexyl group,
R$^2$ represents H, alkyl group having 1 to 22 carbon atoms, alkenyl group having 2 to 22 carbon atoms, benzyl group, R$^7$—O—CH$_2$—CH(OH)—CH$_2$—, R$^8$—O—CH$_2$—CH(CH$_2$OH)—, R$^9$—CH(CH$_2$OH)—, R$^{10}$—CH(OH)—CH$_2$— or hydroxycyclohexyl group,
R$^3$ and R$^4$ represent H, alkyl group having 1 to 22 carbon atoms, alkenyl group having 2 to 22 carbon atoms or phenyl group,
R$^5$ and R$^6$ represent H, alkyl group having 1 to 20 carbon atoms, alkenyl group having 2 to 20 carbon atoms or phenyl group,
R$^7$ and R$^8$ represent H, alkyl group having 1 to 22 carbon atoms, alkenyl group having 2 to 22 carbon atoms or phenyl group,
R$^9$ and R$^{10}$ represent H, alkyl group having 1 to 20 carbon atoms, alkenyl group having 2 to 20 carbon atoms or phenyl group,
provided that when R$^1$ represents H, alkyl group having 1 to 22 carbon atoms, alkenyl group having 2 to 22 carbon atoms or benzyl group, R$^2$ does not represents any of H, alkyl group having 1 to 22 carbon atoms, alkenyl group having 2 to 22 carbon atoms and benzyl group,
or salt thereof.

2. The ascorbic acid derivative or salt thereof according to claim 1 which is characterized by that R$^1$ is an alkyl group having 1 to 22 carbon atoms, alkenyl group having 2 to 22 carbon atoms, benzyl group, R$^3$—O—CH$_2$—CH(OH)—CH$_2$—, R$^4$—O—CH$_2$—CH(CH$_2$OH)—, R$^5$—CH(CH$_2$OH)—, R$^6$—CH(OH)—CH$_2$— or hydroxycyclohexyl group, and R$^2$ is an alkyl group having 1 to 22 carbon atoms, alkenyl group having 2 to 22 carbon atoms, benzyl group, R$^7$—O—CH$_2$—CH(OH)—CH$_2$—, R$^8$—O—CH$_2$—CH(CH$_2$OH)—, R$^9$—CH(CH$_2$OH)—, R$^{10}$—CH(OH)—CH$_2$— or hydroxycyclohexyl group, in the above-described general formula (I).

3. The ascorbic acid derivative or salt thereof according to claim 1 which is characterized by that R$^1$ is H, R$^3$—O—CH$_2$—CH(OH)—CH$_2$—, R$^4$—O—CH$_2$—CH(CH$_2$OH)—, R$^5$—CH(CH$_2$OH)—, R$^6$—CH(OH)—CH$_2$— or hydroxycyclohexyl group, and R$^2$ is H, R$^7$—O—CH$_2$—CH(OH)—CH$_2$—, R$^8$—O—CH$_2$—CH(CH$_2$OH)—, R$^9$—CH(CH$_2$OH)—, R$^{10}$—CH(OH)—CH$_2$— or hydroxycyclohexyl group in the above-described general formula (I).

4. The ascorbic acid derivative or salt thereof according to claim 1 in which one of R$^1$ or R$^2$ is HO—CH$_2$—CH(OH)—CH$_2$— and the other of R$^1$ or R$^2$ is an alkyl group having 4 to 16 carbon atoms, in the above-described general formula (I).

5. The ascorbic acid derivative or salt thereof according to claim 1, in which one of R$^1$ or R$^2$ is R$^a$—O—CH$_2$—CH(OH)—CH$_2$—, wherein R$^a$ represents an alkyl group having 2 to 20 carbon atoms, and the other of R$^1$ or R$^2$ is an alkyl group having 2 to 20 carbon atoms, in the above-described general formula (I).

6. The ascorbic acid derivative or salt thereof according to claim 1, in which one of R$^1$ or R$^2$ is R$^b$—CH(CH$_2$OH)—, wherein R$^b$ represents an alkyl group having 6 to 20 carbon atoms, and the other of R$^1$ or R$^2$ is an alkyl group having 4 to 6 carbon atoms or R$^c$—CH(CH$_2$OH)—, wherein R$^c$ represents an alkyl group having 4 to 6 carbon atoms, in the above-described general formula (I).

7. The ascorbic acid derivative or salt thereof according to claim 1, in which one of R$^1$ or R$^2$ is R$^e$—O—CH$_2$—CH(OH)—CH$_2$—, wherein R$^e$ represents a phenyl group, in the above-described general formula (I).

8. The ascorbic acid derivative or salt thereof according to claim 1, in which one of R$^1$ or R$^2$ is HO—CH$_2$—CH(OH)—CH$_2$— and the other of R$^1$ or R$^2$ is R$^d$—O—CH$_2$—CH(OH)—CH$_2$—, wherein R$^d$ represents an alkyl group having 10 to 16 carbon atoms, in the above-described general formula (I).

9. The ascorbic acid derivative or salt thereof according to claim 1, in which R$^1$ is R$^3$—O—CH$_2$—CH(OH)—CH$_2$—, R$^4$—O—CH$_2$—CH(CH$_2$OH)—, R$^5$—CH(CH$_2$OH)— or R$^6$—CH(OH)—CH$_2$—, and R$^3$, R$^4$, R$^5$, R$^6$ and R$^2$ represent H, alkyl or alkenyl, and the total number of carbon atoms of R$^3$, R$^4$, R$^5$, R$^6$ and R$^2$ is 4 or less,
in which R$^2$ is R$^7$—O—CH$_2$—CH(OH)—CH$_2$—, R$^8$—O—CH$_2$—CH(CH$_2$OH)—, R$^9$—CH(CH$_2$OH)— or R$^{10}$—O—CH(OH)—CH$_2$—, and R$^7$, R$^8$, R$^9$, R$^{10}$ and R$^1$ represent H, alkyl or alkenyl, and the total number of carbon atoms of R$^7$, R$^8$, R$^9$, R$^{10}$ and R$^1$ is 4 or less, or
in which R$^1$ is R$^3$—O—CH$_2$—CH(OH)—CH$_2$—, R$^4$—O—CH$_2$—CH(CH$_2$OH)—, R$^5$—CH(CH$_2$OH)— or R$^6$—CH(OH)—CH$_2$—, and R$^2$ is R$^7$—O—CH$_2$—CH(OH)—CH$_2$—, R$^8$—O—CH$_2$—CH(CH$_2$OH)—, R$^9$—CH(CH$_2$OH)— or R$^{10}$—CH(OH)—CH$_2$—, R$^3$, R$^4$, R$^5$, R$^6$, R$^{7, 8}$, R$^9$ and R$^{10}$ represent H, alkyl or alkenyl and the total number of carbon atoms of R$^3$, R$^4$, R$^5$, R$^6$, R$^7$, R$^8$, R$^9$ and R$^{10}$ is 4 or less.

10. A cosmetic obtained by compounding an ascorbic acid derivative or salt thereof according to any one of claims 1 to 9.

11. A cosmetic obtained by compounding an ascorbic acid derivative or salt thereof according to claim 9 in an amount of 5 to 20% by weight.

12. The ascorbic acid derivative or salt thereof according to claim 1 wherein the ascorbic acid derivative is 2-O-glyceryl ascorbic acid.

13. The ascorbic acid derivative or salt thereof according to claim 1 wherein the ascorbic acid derivative is 2,3-di-O-glyceryl ascorbic acid.

14. The ascorbic acid derivative or salt thereof according to claim 1 wherein the ascorbic acid derivative is 3-O-glyceryl-2-O-octyl ascorbic acid.

15. The ascorbic acid derivative or salt thereof according to claim 1 wherein the ascorbic acid derivative is 2-O-butylglyceryl ascorbic acid.

16. A cream obtained by compounding an ascorbic acid derivative or salt thereof according to any one of claims 1 to 9 with carboxyvinyl polymer.

17. A lotion obtained by compounding an ascorbic acid derivative or salt thereof according to any one of claims 1 to 9 with alcohol and a buffer.

* * * * *

UNITED STATES PATENT AND TRADEMARK OFFICE
CERTIFICATE OF CORRECTION

PATENT NO. : 8,163,939 B2
APPLICATION NO. : 12/673952
DATED : April 24, 2012
INVENTOR(S) : Masato Yoshioka et al.

It is certified that error appears in the above-identified patent and that said Letters Patent is hereby corrected as shown below:

ON THE TITLE PAGE:

At item (73), Assignee, change "Seikwa Kasei Company, Limited, Osaka (JP)" to --Seiwa Kasei Company, Limited, Osaka (JP)--.

Signed and Sealed this
Tenth Day of July, 2012

David J. Kappos
*Director of the United States Patent and Trademark Office*